US009109264B2

(12) United States Patent
Linnen et al.

(10) Patent No.: US 9,109,264 B2
(45) Date of Patent: *Aug. 18, 2015

(54) COMPOSITIONS AND METHODS FOR DETECTING HEPATITIS B VIRUS

(75) Inventors: Jeffrey M. Linnen, Poway, CA (US); Daniel P. Kolk, Ramona, CA (US); Janel M. Dockter, Oceanside, CA (US); Damon K. Getman, Poway, CA (US); Tadashi Yoshimura, Chiba (JP); Martha K. Ho-Sing-Loy, San Diego, CA (US); Reinhold B. Pollner, San Diego, CA (US); Leslie A. Stringfellow, San Diego, CA (US)

(73) Assignee: Gen-Probe Incorporated, San Diego, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 12/830,574

(22) Filed: Jul. 6, 2010

(65) Prior Publication Data
US 2011/0081645 A1    Apr. 7, 2011

Related U.S. Application Data

(63) Continuation of application No. 11/872,538, filed on Oct. 15, 2007, now Pat. No. 7,785,844, which is a continuation of application No. 10/461,790, filed on Jun. 13, 2003, now abandoned.

(60) Provisional application No. 60/389,393, filed on Jun. 14, 2002.

(51) Int. Cl.
C07H 21/04 (2006.01)
C12Q 1/68 (2006.01)
C12Q 1/70 (2006.01)

(52) U.S. Cl.
CPC .................................... C12Q 1/706 (2013.01)

(58) Field of Classification Search
None
See application file for complete search history.

(56) References Cited

U.S. PATENT DOCUMENTS

| 4,562,159 | A | 12/1985 | Shafritz |
| 5,124,246 | A | 6/1992 | Urdea et al. |
| 5,176,995 | A | 1/1993 | Sninsky et al. |
| 5,478,893 | A | 12/1995 | Ghosh et al. |
| 5,501,963 | A | 3/1996 | Burckhardt |
| 5,556,773 | A * | 9/1996 | Yourno ........................ 435/91.2 |
| 5,573,907 | A | 11/1996 | Carrino et al. |
| 5,578,444 | A | 11/1996 | Edwards et al. |
| 5,589,332 | A | 12/1996 | Shih et al. |
| 5,594,118 | A | 1/1997 | Urdea et al. |
| 5,614,362 | A | 3/1997 | Urdea et al. |
| 5,629,153 | A | 5/1997 | Urdea et al. |
| 5,646,262 | A | 7/1997 | Korba et al. |
| 5,663,242 | A | 9/1997 | Ghosh et al. |
| 5,667,974 | A | 9/1997 | Birkenmeyer et al. |
| 5,679,510 | A | 10/1997 | Ray et al. |
| 5,726,014 | A | 3/1998 | Edwards et al. |
| 5,736,316 | A | 4/1998 | Irvine et al. |
| 5,736,334 | A * | 4/1998 | Spies ................................. 435/5 |
| 5,780,219 | A | 7/1998 | McDonough et al. |
| 5,824,518 | A * | 10/1998 | Kacian et al. .............. 435/91.21 |
| 5,849,481 | A | 12/1998 | Urdea et al. |
| 5,856,084 | A | 1/1999 | Karayiannis et al. |
| 5,856,459 | A | 1/1999 | Frank et al. |
| 5,858,652 | A | 1/1999 | Laffler et al. |
| 5,858,732 | A | 1/1999 | Solomon et al. |
| 5,861,244 | A | 1/1999 | Wang et al. |
| 5,869,241 | A | 2/1999 | Edwards et al. |
| 5,928,862 | A | 7/1999 | Morrison |
| 5,955,598 | A | 9/1999 | Birkenmeyer et al. |
| 5,981,274 | A | 11/1999 | Tyrrell et al. |
| 5,985,662 | A | 11/1999 | Anderson et al. |
| 5,994,075 | A | 11/1999 | Goodfellow |
| 5,994,076 | A | 11/1999 | Chenchik et al. |
| 6,080,580 | A | 6/2000 | Baker et al. |
| 6,080,912 | A | 6/2000 | Bremel et al. |
| 6,172,193 | B1 | 1/2001 | Primi et al. |
| 6,174,670 | B1 | 1/2001 | Wittwer et al. |
| 6,228,642 | B1 | 5/2001 | Baker et al. |
| 6,232,079 | B1 | 5/2001 | Wittwer et al. |
| 6,245,514 | B1 | 6/2001 | Wittwer |
| 6,258,937 | B1 | 7/2001 | Tong et al. |
| 6,287,770 | B1 | 9/2001 | Weston et al. |
| 6,291,740 | B1 | 9/2001 | Bremel et al. |
| 6,303,295 | B1 | 10/2001 | Taylor et al. |
| 6,346,416 | B1 | 2/2002 | Dean et al. |
| 6,352,829 | B1 | 3/2002 | Chenchik et al. |
| 6,583,279 | B1 | 6/2003 | Berger et al. |
| 7,262,292 | B2 | 8/2007 | Pasupuleti et al. |
| 7,723,078 | B2 | 5/2010 | Dieman et al. |
| 7,785,844 | B2 * | 8/2010 | Linnen et al. .............. 435/91.51 |
| 2003/0143527 | A1 | 7/2003 | Shyamala |
| 2004/0029111 | A1 | 2/2004 | Linnen et al. |
| 2008/0081328 | A1 | 4/2008 | Linnen et al. |

FOREIGN PATENT DOCUMENTS

| AU | 2003253651 | 5/2010 |
| DE | 198 32 050 A1 | 1/2000 |
| EP | 0 309 230 A2 | 3/1989 |
| EP | 0 357 011 A2 | 3/1990 |
| EP | 0 408 295 A2 | 1/1991 |

(Continued)

OTHER PUBLICATIONS

Durigon et al. (Journal of Virological Methods 44 (1993) 155-165).*

(Continued)

Primary Examiner — Juliet Switzer
(74) Attorney, Agent, or Firm — Jeffrey E. Landes

(57) ABSTRACT

Compositions, methods and kits for detecting viral nucleic acids. Targets that can be detected in accordance with the invention include HBV and/or HIV-1 and/or HCV nucleic acids. Particularly described are oligonucleotides that are useful as hybridization probes and amplification primers that facilitate detection of very low levels of HBV nucleic acids.

33 Claims, 3 Drawing Sheets

(56) References Cited

FOREIGN PATENT DOCUMENTS

| | | |
|---|---|---|
| EP | 0 569 237 A3 | 11/1993 |
| EP | 0 590 327 A2 | 4/1994 |
| EP | 0 971 039 A2 | 6/1998 |
| EP | 1 033 411 A2 | 9/2000 |
| EP | 1 103 624 A2 | 5/2001 |
| EP | 1 104 811 A1 | 6/2001 |
| EP | 1 174 523 A2 | 1/2002 |
| EP | 1 179 600 A1 | 2/2002 |
| EP | 1 275 715 A1 | 1/2003 |
| EP | 2 292 801 A2 | 3/2011 |
| WO | 89/04375 A1 | 5/1989 |
| WO | 91/10746 A1 | 7/1991 |
| WO | 93/13120 A1 | 7/1993 |
| WO | 94/08032 A1 | 4/1994 |
| WO | 95/02690 A1 | 1/1995 |
| WO | 95/13399 A1 | 5/1995 |
| WO | 96/21043 A1 | 7/1996 |
| WO | 96/40996 A1 | 12/1996 |
| WO | 97/40193 A2 | 10/1997 |
| WO | WO 97/40193 * | 10/1997 |
| WO | 98/21317 A1 | 5/1998 |
| WO | 98/27225 A1 | 6/1998 |
| WO | 99/37805 A1 | 7/1999 |
| WO | 01/04358 A2 | 1/2001 |
| WO | 01/04361 A2 | 1/2001 |
| WO | WO 01/04361 * | 1/2001 |
| WO | 01/07661 A2 | 2/2001 |
| WO | 01/36442 A1 | 5/2001 |
| WO | 01/38498 A2 | 5/2001 |
| WO | 01/40279 A2 | 6/2001 |
| WO | 01/59103 A2 | 8/2001 |
| WO | 01/64959 A1 | 9/2001 |
| WO | 01/68921 A2 | 9/2001 |
| WO | 01/77317 A2 | 10/2001 |
| WO | 01/79548 A2 | 10/2001 |
| WO | 01/79563 A2 | 10/2001 |
| WO | 03/031934 A2 | 4/2003 |
| WO | 03/050308 A1 | 6/2003 |
| WO | 03/093797 A2 | 11/2003 |
| WO | 03/106714 A1 | 12/2003 |

OTHER PUBLICATIONS

Buck et al. (BioTechniques 27:528-536 (1999)).*
McDonough et al. (Infusion Therapy and Transfusion Medicine, 1998, 25: 164-169.*
Stuyver et al. (Journal of General Virology (2000) 81, 67-74).*
GenBank record having Accession AF160501, dated Feb. 17, 2000, three pages, obtained from http://www.ncbi.nlm.nih.gov/nuccore/AF160501.1?report=GenBank on Jan. 31, 2012.*
de Baar et al. (J. Clin. Microbiology 2001, 39(4)1378-1384).*
Roth et al. (The Lancet, vol. 353, 1999, pp. 359-363.*
Abe et al. J. Clin. Microbiol. 1999, 37(9):2899-2903.*
Sumazaki et al. Journal of Medical Virology 27:304-308 (1989).*
Heermann et al. Journal of Virological Methods 50 (1994) 43-58.*
Kaneko et al. J. Clin. Microbiol. 1989, 27(9):1930-1933.*
Innis et al. PCR Protocols, A Guide to Methods and Applications, Ed. by Michael Innis et al. 1990, pp. 3-12.*
Extended European Search Report in corresponding EP Application No. 10176396.9-2406 dated Aug. 22, 2011.
Caudai et al., "Antibody Testing and RT-PCR Results in Hepatitis C Virus (HCV) . . . "; Infection, 1998, 26 (3): 151-4.
Defoort et al., "Simultaneous Detection of Multiplex-Amplified Human Immunodeficiency Virus Type 1 RNA, Hepatitis C Virus RNA, and Hepatitis B Virus DNA Using a Flow Cytometer Microsphere-Based Hybridization Assay", J. Clin. Microbiol., Mar. 2000, 38(3):1066-1071, Am. Society for Microbiology, USA.
Fukai et al., "Etiologic Considerations of Fulminant Non-A, Non-B Viral Hepatitis in Japan . . . "; J Infectious Diseases, 1998, 178: 325-33.
Ganem, Don, "Hepadnaviridae and Their Replication", (Chptr 85) Fields Virology, 3rd Ed., Fields et al., Eds., Lippincott-Raven Pub., Philadephia, 1996, 2703-37.
Gerlich et al., Quantitative Assays for Hepatitis B Virus DNA: Standardization and Quality Control, Viral Hepatitis Review, 1995, 1 (1): 53-7.
Gitlin, Norman, Hepatitis B: Diagnosis, Prevention, and Treatment, Clinical Chem., 1997, 43:8(B): 1500-6.
Hill et al., "Molecular diagnostic testing for infectious diseases using TMA technology", Expert Rev. Mol. Diagn., Nov. 2001, 1(4):445-455, Future Drugs Ltd., London, GB.
Hollinger, F. Blaine, "Hepatitis B Virus", (Chptr 86) Fields Virology, 3rd Ed., Fields et al., Eds., Lippincott-Raven Pub., Philadelphia, 1996, 2739-2807.
Jagodzinski et. al., "Detection of Hepatitis B Viral Sequences in Early HBV Infection", Nov. 1994, Poster presented at 47th Annual Mtg., American Assoc. of Blood Banks.
Kaneko et al., "Detection of Hepatitis B Virus DNA in Serum by Polymerase Chain Reaction: Application for Clinical Diagnosis", Gastroenterology, 1990, 99: 799-804.
Kolk, D., et al., "A Fully Automated, High Throughput System for Simultaneous Screening of HIV-1, HCV and HBV in Blood Donations", Abs.P-123, Vox Sanguinis, 2002, 42.
Krajden, Mel, "Assessment of Hepatitis B Virus DNA Stability in Serum by the Chiron Quantiplex Branched-DNA Assay", J Clin Microbiology, Feb. 1998: 382-6.
Leone et al., "Molecular beacon probes combined with amplification by NASBA enable homogeneous, real-time detection of RNA", Nucl. Acids Res., Jan. 1998, 26(9):2150-2155, Oxford University Press, Surrey, GB.
Light et al., "Target Capture as Sample Processing for Trasncription-Mediated Amplification (TMA) and Subsequent Detection and Differentiation of Neisseria gonorrhoeae and Chlamydia trachomatis in a Single Tube," Clin. Chem., 1998, 44(6):A5, Supplement, Abstract #17, American Association for Clinical Chemistry, Washington, D.C., USA.
Linnen, J.M., et al., "Sensitivity & Specificity of a TMA-Based Triplex Assay for Simult. Screen. of H1V-1, HCV & HBV in Blood Donations", Abs.P-549, Vox Sanguinis, 2002, 183.
Linnen, J.M., et al., "Effect of Donor Mini-Pool Size on Closure of the Hepatitis B Virus (HBV) Detection Window . . . ", Abs.P-126, Vox Sanguinis, 2002, 43.
Linnen, J.M., et al., "Performance of the TMA Triplex Assay Which Simult. Detects HIV-1, HCV and HBV Nucleic Acid", Abs.SP155, Transfusion, Sep. 2001, 41 (95): 82S.
Magnius, et al., "Subtypes, Genotypes & Molecular Epidemiology of the Hepatitis B Virus . . . ", Intervirology, 1995 (38): 24-34.
Meng et al., "Automated Multiplex Assay System for Simultaneous Detection of Hepatitis B Virus DNA, Hepatitis C Virus RNA, and Human Immunodeficiency Virus Type 1 RNA", J. Clin. Microbiol., Aug. 2001, 39(8):2937-2945, ASM, USA.
McDonough et al., "High Throughput Assay for the Simultaneous or Separate Detection of Human Immunodeficiency Virus (HIV) and Hepatitis Type C Virus (HCV)", Infusionther Transfusionmed, 1998, 25:164-169, Karger GmbH, Basil Switzerland.
Nelson et al., "Simultaneous Detection of Multiple Nucleic Acid Targets in a Homogenous Format", Biochemistry, Jun. 1996, 35:8429-8438, American Chemical Society, Pennsylvania, US.
Okamoto, et al., "Nucleotide Sequence of a Closed Hepatitis B Virus Genome, Subtype ayr . . . " J. Gen. Virol., 1986 (67):2305-14.
Paterlini, et al., "Polymeric Chain Reaction to Detect Hepatitis B Virus DNA and RNA Sequences in Primary Liver Cancers . . . ", NEJM, 1990, 323 (2): 80-5.
Roth, et al., "Feasibility & Efficacy of Routine PCR Screening of Blood Donations for HCV, HBV & HIV-1 in a Blood Bank Setting", Lancet, 1999, 353: 359-63.
Stringfellow et al., "Early Detection of HBV Using the Transcription-Mediated Amplification/Dual Kinetic Assay System", Transfusion, 1999, 39(10):68S, XP009064337(Abstract).
Tobler et al., "History of Posttransfusion Hepatitis", Clin.Chem. 1997, 43-8(B): 1487-93.
Worman et al., "Molecular Biological Methods in Diagnosis & Treatment of Liver Diseases", Clin.Chem. 1997, 43-8 (B): 1476-86.
AU Communication for corresponding AU Application 2003253651 dated Jun. 24, 2009.

(56) References Cited

OTHER PUBLICATIONS

Restriction Requirement in U.S. Appl. No. 10/461,790 dated Jan. 26, 2006.
Office Action in U.S. Appl. No. 10/461,790 dated Jun. 9, 2006.
Office Action in U.S. Appl. No. 10/461,790 dated Oct. 18, 2006.
Examiner's Report in corresponding Australian Application No. 2010201842 dated Dec. 2, 2011.
Examiner's Report in corresponding Canadian Application No. 2,486,420 dated Mar. 28, 2012.
Examination Report, European Patent Application No. 10 176 396.9-2406, mailed Oct. 30, 2012.
Patent Examination Report No. 2, Australian Patent Application No. 2012202286, issued Dec. 13, 2013.
International Search Report of corresponding PCT Application PCT/US2003/18993 dated Nov. 5, 2003.
EPO Communication pursuant to Rules 109 & 110 in corresponding EP Application 03 760 408 dated Jan. 24, 2005.
EPO Communication pursuant to Rule 46(1) in corresponding EP Application 03 760 408 dated Jun. 29, 2005.
Supplementary Search Report pursuant to Article 157(2a) in corresponding EP Application 03 760 408 dated Apr. 4, 2006.
EPO Communication pursuant to Article 96(2) in corresponding EP Application 03 760 408 dated Jan. 18, 2007.
AU Communication (1st Exam Rpt) for corresponding AU Application 2003253651 dated May 30, 2008.
EPO Communication pursuant to Article 94(3) in corresponding EP Application 03 760 408 dated Jul. 23, 2009.
AU Notice of Acceptance for corresponding AU Application 2003253651 dated Jan. 13, 2010.
Office Action in corresponding U.S. Appl. No 11/872,538—dated Mar. 12, 2010.
ExIN and Notice of Allowance in corresponding U.S. Appl. No. 11/872,538—dated Jun. 16, 2010.
EPO Communication pursuant to Article 94(3) in corresponding EP Application 03 760 408 dated Aug. 5, 2010.
Partial European Search Report pursuant to Rule 64 in corresponding EP Application 10 176 396 dated Jan. 17, 2011.
EPO Communication pursuant to Rule 71(3) in corresponding EP Application 03 760 408 dated Mar. 3, 2011.
Official Action, Japanese Patent Application No. 2004-513526, dated Apr. 23, 2010.
Abstract, Japanese Patent Application No. 2011-019528, dated Feb. 3, 2011.

\* cited by examiner

SEQUENCE LISTING

```
<160> NUMBER OF SEQ ID NOS: 142

<210> SEQ ID NO 1
<211> LENGTH: 128
<212> TYPE: DNA
<213> ORGANISM: Hepatitis B Virus

<400> SEQUENCE: 1
gtgtcttggc caaaattcgc agtccccaac ctccaatcac tcaccaacct cctgtcctcc      60
aatttgtcct ggttatcgct ggatgtgtct gcggcgtttt atcatattcc tcttcatcct     120
gctgctat                                                              128

<210> SEQ ID NO 2
<211> LENGTH: 50
<212> TYPE: DNA
<213> ORGANISM: Hepatitis B Virus

<400> SEQUENCE: 2
ctggatgtgt ctgcggcgtt ttatcatatt cctcttcatc ctgctgctat                 50

<210> SEQ ID NO 3
<211> LENGTH: 28
<212> TYPE: DNA
<213> ORGANISM: Hepatitis B Virus

<400> SEQUENCE: 3
atcatattcc tcttcatcct gctgctat                                         28

<210> SEQ ID NO 4
<211> LENGTH: 54
<212> TYPE: DNA
<213> ORGANISM: Hepatitis B Virus

<400> SEQUENCE: 4
ggaattagag gacaaacggg caacatacct tgataatcca gaagaaccaa taag            54

<210> SEQ ID NO 5
<211> LENGTH: 21
<212> TYPE: DNA
<213> ORGANISM: Hepatitis B Virus
```

```
<400> SEQUENCE: 5
ttgataatcc agaagaacca a                                         21

<210> SEQ ID NO 6
<211> LENGTH: 21
<212> TYPE: DNA
<213> ORGANISM: Hepatitis B Virus

<400> SEQUENCE: 6
cttgataatc cagaagaacc a                                         21

<210> SEQ ID NO 7
<211> LENGTH: 24
<212> TYPE: DNA
<213> ORGANISM: Hepatitis B Virus

<400> SEQUENCE: 7
taccttgata atccagaaga acca                                      24

<210> SEQ ID NO 8
<211> LENGTH: 22
<212> TYPE: DNA
<213> ORGANISM: Hepatitis B Virus

<400> SEQUENCE: 8
gataatccag aagaaccaat aa                                        22

<210> SEQ ID NO 9
<211> LENGTH: 22
<212> TYPE: DNA
<213> ORGANISM: Hepatitis B Virus

<400> SEQUENCE: 9
ataatccaga agaaccaata ag                                        22

<210> SEQ ID NO 10
<211> LENGTH: 20
<212> TYPE: DNA
<213> ORGANISM: Hepatitis B Virus

<400> SEQUENCE: 10
agaggacaaa cgggcaacat                                           20

<210> SEQ ID NO 11
<211> LENGTH: 20
<212> TYPE: DNA
<213> ORGANISM: Hepatitis B Virus

<400> SEQUENCE: 11
aggacaaacg ggcaacatac                                           20

<210> SEQ ID NO 12
<211> LENGTH: 31
<212> TYPE: DNA
<213> ORGANISM: Hepatitis B Virus

<400> SEQUENCE: 12
ggaattagag gacaaacggg caacatacct t                              31

<210> SEQ ID NO 13
<211> LENGTH: 27
<212> TYPE: DNA
<213> ORGANISM: Hepatitis B Virus
```

```
<400> SEQUENCE: 13
ttagaggaca aacgggcaac atacctt                                        27

<210> SEQ ID NO 14
<211> LENGTH: 24
<212> TYPE: DNA
<213> ORGANISM: Hepatitis B Virus

<400> SEQUENCE: 14
gaggacaaac gggcaacata cctt                                           24

<210> SEQ ID NO 15
<211> LENGTH: 21
<212> TYPE: DNA
<213> ORGANISM: Hepatitis B Virus

<400> SEQUENCE: 15
gacaaacggg caacatacct t                                              21

<210> SEQ ID NO 16
<211> LENGTH: 24
<212> TYPE: DNA
<213> ORGANISM: Hepatitis B Virus

<400> SEQUENCE: 16
gtgtcttggc caaaattcgc agtc                                           24

<210> SEQ ID NO 17
<211> LENGTH: 26
<212> TYPE: DNA
<213> ORGANISM: Hepatitis B Virus

<400> SEQUENCE: 17
gtccccaacc tccaatcact caccaa                                         26

<210> SEQ ID NO 18
<211> LENGTH: 24
<212> TYPE: DNA
<213> ORGANISM: Hepatitis B Virus

<400> SEQUENCE: 18
cccaacctcc aatcactcac caac                                           24

<210> SEQ ID NO 19
<211> LENGTH: 26
<212> TYPE: DNA
<213> ORGANISM: Hepatitis B Virus

<400> SEQUENCE: 19
ctgtcctcca atttgtcctg gttatc                                         26

<210> SEQ ID NO 20
<211> LENGTH: 27
<212> TYPE: DNA
<213> ORGANISM: Hepatitis B Virus

<400> SEQUENCE: 20
ccaacctcct gtcctccaat tgtcct                                         27

<210> SEQ ID NO 21
<211> LENGTH: 27
<212> TYPE: DNA
```

```
<213> ORGANISM: Hepatitis B Virus

<400> SEQUENCE: 21
caacctcctg tcctccaatt tgtcctg                                              27

<210> SEQ ID NO 22
<211> LENGTH: 20
<212> TYPE: DNA
<213> ORGANISM: Hepatitis B Virus

<400> SEQUENCE: 22
ctggatgtgt ctgcggcgtt                                                      20

<210> SEQ ID NO 23
<211> LENGTH: 22
<212> TYPE: DNA
<213> ORGANISM: Hepatitis B Virus

<400> SEQUENCE: 23
gatgtgtctg cggcgtttta tc                                                   22

<210> SEQ ID NO 24
<211> LENGTH: 23
<212> TYPE: DNA
<213> ORGANISM: Hepatitis B Virus

<400> SEQUENCE: 24
atcatattcc tcttcatcct gct                                                  23

<210> SEQ ID NO 25
<211> LENGTH: 23
<212> TYPE: DNA
<213> ORGANISM: Hepatitis B Virus

<400> SEQUENCE: 25
atattcctct tcatcctgct gct                                                  23

<210> SEQ ID NO 26
<211> LENGTH: 23
<212> TYPE: DNA
<213> ORGANISM: Hepatitis B Virus
<220> FEATURE:
<221> NAME/KEY: modified_base
<222> LOCATION: (11)...(11)
<223> OTHER INFORMATION: I

<400> SEQUENCE: 26
atattcctct ncatcctgct gct                                                  23

<210> SEQ ID NO 27
<211> LENGTH: 24
<212> TYPE: DNA
<213> ORGANISM: Hepatitis B Virus

<400> SEQUENCE: 27
atattcctct tcatcctgct gcta                                                 24

<210> SEQ ID NO 28
<211> LENGTH: 23
<212> TYPE: DNA
<213> ORGANISM: Hepatitis B Virus

<400> SEQUENCE: 28
attcctcttc atcctgctgc tat                                                  23
```

```
<210> SEQ ID NO 29
<211> LENGTH: 21
<212> TYPE: DNA
<213> ORGANISM: Hepatitis B Virus

<400> SEQUENCE: 29
aatttgtcct ggttatcgct g                                              21

<210> SEQ ID NO 30
<211> LENGTH: 18
<212> TYPE: DNA
<213> ORGANISM: Hepatitis B Virus

<400> SEQUENCE: 30
cctggttatc gctggatg                                                  18

<210> SEQ ID NO 31
<211> LENGTH: 18
<212> TYPE: DNA
<213> ORGANISM: Hepatitis B Virus

<400> SEQUENCE: 31
ctggttatcg ctggatgt                                                  18

<210> SEQ ID NO 32
<211> LENGTH: 18
<212> TYPE: DNA
<213> ORGANISM: Hepatitis B Virus

<400> SEQUENCE: 32
tggttatcgc tggatgtg                                                  18

<210> SEQ ID NO 33
<211> LENGTH: 51
<212> TYPE: DNA
<213> ORGANISM: Artificial Sequence
<220> FEATURE:
<223> OTHER INFORMATION: HBV-specific promoter-primer

<400> SEQUENCE: 33
aatttaatac gactcactat agggagagtg tcttggccaa aattcgcagt c              51

<210> SEQ ID NO 34
<211> LENGTH: 53
<212> TYPE: DNA
<213> ORGANISM: Artificial Sequence
<220> FEATURE:
<223> OTHER INFORMATION: HBV-specific promoter-primer

<400> SEQUENCE: 34
aatttaatac gactcactat agggagagtc cccaacctcc aatcactcac caa            53

<210> SEQ ID NO 35
<211> LENGTH: 51
<212> TYPE: DNA
<213> ORGANISM: Artificial Sequence
<220> FEATURE:
<223> OTHER INFORMATION: HBV-specific promoter-primer

<400> SEQUENCE: 35
aatttaatac gactcactat agggagaccc aacctccaat cactcaccaa c              51

<210> SEQ ID NO 36
```

```
<210> SEQ ID NO 36
<211> LENGTH: 53
<212> TYPE: DNA
<213> ORGANISM: Artificial Sequence
<220> FEATURE:
<223> OTHER INFORMATION: HBV-specific promoter-primer

<400> SEQUENCE: 36
aatttaatac gactcactat agggagactg tcctccaatt tgtcctggtt atc        53

<210> SEQ ID NO 37
<211> LENGTH: 54
<212> TYPE: DNA
<213> ORGANISM: Artificial Sequence
<220> FEATURE:
<223> OTHER INFORMATION: HBV-specific promoter-primer

<400> SEQUENCE: 37
aatttaatac gactcactat agggagacca acctcctgtc ctccaatttg tcct       54

<210> SEQ ID NO 38
<211> LENGTH: 54
<212> TYPE: DNA
<213> ORGANISM: Artificial Sequence
<220> FEATURE:
<223> OTHER INFORMATION: HBV-specific promoter-primer

<400> SEQUENCE: 38
aatttaatac gactcactat agggagacaa cctcctgtcc tccaatttgt cctg       54

<210> SEQ ID NO 39
<211> LENGTH: 47
<212> TYPE: DNA
<213> ORGANISM: Artificial Sequence
<220> FEATURE:
<223> OTHER INFORMATION: HBV-specific promoter-primer

<400> SEQUENCE: 39
aatttaatac gactcactat agggagactg gatgtgtctg cggcgtt               47

<210> SEQ ID NO 40
<211> LENGTH: 49
<212> TYPE: DNA
<213> ORGANISM: Artificial Sequence
<220> FEATURE:
<223> OTHER INFORMATION: HBV-specific promoter-primer

<400> SEQUENCE: 40
aatttaatac gactcactat agggagagat gtgtctgcgg cgttttatc             49

<210> SEQ ID NO 41
<211> LENGTH: 50
<212> TYPE: DNA
<213> ORGANISM: Artificial Sequence
<220> FEATURE:
<223> OTHER INFORMATION: HBV-specific promoter-primer

<400> SEQUENCE: 41
aatttaatac gactcactat agggagaatc atattcctct tcatcctgct            50

<210> SEQ ID NO 42
<211> LENGTH: 50
<212> TYPE: DNA
<213> ORGANISM: Artificial Sequence
<220> FEATURE:
<223> OTHER INFORMATION: HBV-specific promoter-primer

<400> SEQUENCE: 42
```

-continued aatttaatac gactcactat agggagaata ttcctcttca tcctgctgct                50

<210> SEQ ID NO 43
<211> LENGTH: 50
<212> TYPE: DNA
<213> ORGANISM: Artificial Sequence
<220> FEATURE:
<223> OTHER INFORMATION: HBV-specific promoter-primer
<221> NAME/KEY: modified_base
<222> LOCATION: (38)...(38)
<223> OTHER INFORMATION: I

<400> SEQUENCE: 43
aatttaatac gactcactat agggagaata ttcctctnca tcctgctgct                50

<210> SEQ ID NO 44
<211> LENGTH: 51
<212> TYPE: DNA
<213> ORGANISM: Artificial Sequence
<220> FEATURE:
<223> OTHER INFORMATION: HBV-specific promoter-primer

<400> SEQUENCE: 44
aatttaatac gactcactat agggagaata ttcctcttca tcctgctgct a              51

<210> SEQ ID NO 45
<211> LENGTH: 50
<212> TYPE: DNA
<213> ORGANISM: Artificial Sequence
<220> FEATURE:
<223> OTHER INFORMATION: HBV-specific promoter-primer

<400> SEQUENCE: 45
aatttaatac gactcactat agggagaatt cctcttcatc ctgctgctat                50

<210> SEQ ID NO 46
<211> LENGTH: 48
<212> TYPE: DNA
<213> ORGANISM: Artificial Sequence
<220> FEATURE:
<223> OTHER INFORMATION: HBV-specific promoter-primer

<400> SEQUENCE: 46
aatttaatac gactcactat agggagaaat ttgtcctggt tatcgctg                  48

<210> SEQ ID NO 47
<211> LENGTH: 45
<212> TYPE: DNA
<213> ORGANISM: Artificial Sequence
<220> FEATURE:
<223> OTHER INFORMATION: HBV-specific promoter-primer

<400> SEQUENCE: 47
aatttaatac gactcactat agggagacct ggttatcgct ggatg                     45

<210> SEQ ID NO 48
<211> LENGTH: 45
<212> TYPE: DNA
<213> ORGANISM: Artificial Sequence
<220> FEATURE:
<223> OTHER INFORMATION: HBV-specific promoter-primer

<400> SEQUENCE: 48
aatttaatac gactcactat agggagactg gttatcgctg gatgt                     45

```
<210> SEQ ID NO 49
<211> LENGTH: 45
<212> TYPE: DNA
<213> ORGANISM: Artificial Sequence
<220> FEATURE:
<223> OTHER INFORMATION: HBV-specific promoter-primer

<400> SEQUENCE: 49
aatttaatac gactcactat agggagatgg ttatcgctgg atgtg            45

<210> SEQ ID NO 50
<211> LENGTH: 17
<212> TYPE: RNA
<213> ORGANISM: Hepatitis B Virus
<220> FEATURE:
<221> NAME/KEY: misc_feature
<222> LOCATION: (1)...(16)
<223> OTHER INFORMATION: 2'-OMe nucleotide analogs

<400> SEQUENCE: 50
agcaggauga agaggaa                                            17

<210> SEQ ID NO 51
<211> LENGTH: 18
<212> TYPE: RNA
<213> ORGANISM: Hepatitis B Virus
<220> FEATURE:
<221> NAME/KEY: misc_feature
<222> LOCATION: (1)...(17)
<223> OTHER INFORMATION: 2'-OMe nucleotide analogs

<400> SEQUENCE: 51
gcagcaggau gaagagga                                           18

<210> SEQ ID NO 52
<211> LENGTH: 17
<212> TYPE: DNA
<213> ORGANISM: Hepatitis B Virus
<220> FEATURE:
<221> NAME/KEY: misc_feature
<222> LOCATION: (1)...(16)
<223> OTHER INFORMATION: 2'-OMe nucleotide analogs

<400> SEQUENCE: 52
gcagcaggat gaagagg                                            17

<210> SEQ ID NO 53
<211> LENGTH: 18
<212> TYPE: RNA
<213> ORGANISM: Hepatitis B Virus
<220> FEATURE:
<221> NAME/KEY: misc_feature
<222> LOCATION: (1)...(17)
<223> OTHER INFORMATION: 2'-OMe nucleotide analogs

<400> SEQUENCE: 53
ugaggcauag cagcagga                                           18

<210> SEQ ID NO 54
<211> LENGTH: 19
<212> TYPE: DNA
<213> ORGANISM: Hepatitis B Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 54
```
gaagatgagg catagcagc                                              19

<210> SEQ ID NO 55
<211> LENGTH: 23
<212> TYPE: RNA
<213> ORGANISM: Hepatitis B Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 55
acaagaagau gaggcauagc agc                                         23

<210> SEQ ID NO 56
<211> LENGTH: 19
<212> TYPE: RNA
<213> ORGANISM: Hepatitis B Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 56
agaagaugag gcauagcag                                              19

<210> SEQ ID NO 57
<211> LENGTH: 18
<212> TYPE: RNA
<213> ORGANISM: Hepatitis B Virus
<220> FEATURE:
<221> NAME/KEY: misc_feature
<222> LOCATION: (1)...(17)
<223> OTHER INFORMATION: 2'-OMe nucleotide analogs

<400> SEQUENCE: 57
aagaagauga ggcauagc                                               18

<210> SEQ ID NO 58
<211> LENGTH: 18
<212> TYPE: DNA
<213> ORGANISM: Hepatitis B Virus
<220> FEATURE:
<221> NAME/KEY: misc_feature
<222> LOCATION: (1)...(17)
<223> OTHER INFORMATION: 2'-OMe nucleotide analogs

<400> SEQUENCE: 58
acaagaagat gaggcata                                               18

<210> SEQ ID NO 59
<211> LENGTH: 18
<212> TYPE: RNA
<213> ORGANISM: Hepatitis B Virus
<220> FEATURE:
<221> NAME/KEY: misc_feature
<222> LOCATION: (1)...(17)
<223> OTHER INFORMATION: 2'-OMe nucleotide analogs

<400> SEQUENCE: 59
ccaacaagaa gaugaggc                                               18

<210> SEQ ID NO 60
<211> LENGTH: 23
<212> TYPE: RNA
<213> ORGANISM: Hepatitis B Virus
<220> FEATURE:
<221> NAME/KEY: misc_feature

```
<222> LOCATION: (1)...(22)
<223> OTHER INFORMATION: 2'-OMe nucleotide analogs
<221> NAME/KEY: modified_base
<222> LOCATION: (2)...(2)
<223> OTHER INFORMATION: I

<400> SEQUENCE: 60
anuccagaag aaccaacaag aag                                            23

<210> SEQ ID NO 61
<211> LENGTH: 23
<212> TYPE: RNA
<213> ORGANISM: Hepatitis B Virus
<220> FEATURE:
<221> NAME/KEY: misc_feature
<222> LOCATION: (1)...(22)
<223> OTHER INFORMATION: 2'-OMe nucleotide analogs
<221> NAME/KEY: modified_base
<222> LOCATION: (2)...(2)
<223> OTHER INFORMATION: I

<400> SEQUENCE: 61
anuccagaag aaccaacaag aag                                            23

<210> SEQ ID NO 62
<211> LENGTH: 20
<212> TYPE: DNA
<213> ORGANISM: Hepatitis B Virus
<220> FEATURE:
<221> NAME/KEY: misc_feature
<222> LOCATION: (1)...(19)
<223> OTHER INFORMATION: 2'-OMe nucleotide analogs

<400> SEQUENCE: 62
ccagaagaac caacaagaag                                                20

<210> SEQ ID NO 63
<211> LENGTH: 22
<212> TYPE: RNA
<213> ORGANISM: Hepatitis B Virus
<220> FEATURE:
<221> NAME/KEY: misc_feature
<222> LOCATION: (1)...(21)
<223> OTHER INFORMATION: 2'-OMe nucleotide analogs

<400> SEQUENCE: 63
ccuugauagu ccagaagaac ca                                             22

<210> SEQ ID NO 64
<211> LENGTH: 23
<212> TYPE: RNA
<213> ORGANISM: Hepatitis B Virus
<220> FEATURE:
<221> NAME/KEY: misc_feature
<222> LOCATION: (1)...(22)
<223> OTHER INFORMATION: 2'-OMe nucleotide analogs

<400> SEQUENCE: 64
ccuugauagu ccagaagaac caa                                            23

<210> SEQ ID NO 65
<211> LENGTH: 17
<212> TYPE: RNA
<213> ORGANISM: Hepatitis B Virus
<220> FEATURE:
<221> NAME/KEY: misc_feature
<222> LOCATION: (1)...(16)
<223> OTHER INFORMATION: 2'-OMe nucleotide analogs
```

```
<400> SEQUENCE: 65
acgggcaaca uaccuug                                            17

<210> SEQ ID NO 66
<211> LENGTH: 16
<212> TYPE: RNA
<213> ORGANISM: Hepatitis B Virus
<220> FEATURE:
<221> NAME/KEY: misc_feature
<222> LOCATION: (1)...(15)
<223> OTHER INFORMATION: 2'-OMe nucleotide analogs

<400> SEQUENCE: 66
cgggcaacau accuug                                             16

<210> SEQ ID NO 67
<211> LENGTH: 71
<212> TYPE: DNA
<213> ORGANISM: Hepatitis B Virus

<400> SEQUENCE: 67
acgggcaaca taccttgata gtccagaaga accaacaaga agatgaggca tagcagcagg    60
atgcagagga a                                                  71

<210> SEQ ID NO 68
<211> LENGTH: 93
<212> TYPE: DNA
<213> ORGANISM: Hepatitis B Virus

<400> SEQUENCE: 68
agactcgtgg tggacttctc tcaatttct aggggatca cccgtgtgtc ttggccaaaa    60
ttcgcagtcc ccaacctcca atcactcacc aac                          93

<210> SEQ ID NO 69
<211> LENGTH: 73
<212> TYPE: DNA
<213> ORGANISM: Hepatitis B Virus

<400> SEQUENCE: 69
cgtttctctt ggctcagttt actagtgcca tttgttcagt ggttcgtagg gctttccccc    60
actgtttggc ttt                                                73

<210> SEQ ID NO 70
<211> LENGTH: 36
<212> TYPE: DNA
<213> ORGANISM: Hepatitis B Virus

<400> SEQUENCE: 70
agactcgtgg tggacttctc tcaatttct aggggg                        36

<210> SEQ ID NO 71
<211> LENGTH: 30
<212> TYPE: DNA
<213> ORGANISM: Hepatitis B Virus

<400> SEQUENCE: 71
gtggtggact tctctcaatt ttctaggggg                              30

<210> SEQ ID NO 72
<211> LENGTH: 20
<212> TYPE: DNA
<213> ORGANISM: Hepatitis B Virus
```

-continued

```
<400> SEQUENCE: 72
ggatcacccg tgtgtcttgg                                                   20

<210> SEQ ID NO 73
<211> LENGTH: 25
<212> TYPE: DNA
<213> ORGANISM: Hepatitis B Virus

<400> SEQUENCE: 73
gtgtcttggc caaaattcgc agtcc                                             25

<210> SEQ ID NO 74
<211> LENGTH: 40
<212> TYPE: DNA
<213> ORGANISM: Hepatitis B Virus

<400> SEQUENCE: 74
gccaaaattc gcagtcccca acctccaatc actcaccaac                             40

<210> SEQ ID NO 75
<211> LENGTH: 27
<212> TYPE: DNA
<213> ORGANISM: Hepatitis B Virus

<400> SEQUENCE: 75
gccaaaattc gcagtcccca acctcca                                           27

<210> SEQ ID NO 76
<211> LENGTH: 27
<212> TYPE: DNA
<213> ORGANISM: Hepatitis B Virus

<400> SEQUENCE: 76
ttcgcagtcc ccaacctcca atcactc                                           27

<210> SEQ ID NO 77
<211> LENGTH: 40
<212> TYPE: DNA
<213> ORGANISM: Hepatitis B Virus

<400> SEQUENCE: 77
cgtttctcct ggctcagttt actagtgcca tttgttcagt                             40

<210> SEQ ID NO 78
<211> LENGTH: 45
<212> TYPE: DNA
<213> ORGANISM: Hepatitis B Virus

<400> SEQUENCE: 78
cgtttctcct ggctcagttt actagtgcca tttgttcagt ggtcg                       45

<210> SEQ ID NO 79
<211> LENGTH: 32
<212> TYPE: DNA
<213> ORGANISM: Hepatitis B Virus

<400> SEQUENCE: 79
tggctcagtt tactagtgcc atttgttcag tg                                     32

<210> SEQ ID NO 80
<211> LENGTH: 32
<212> TYPE: DNA
```

<213> ORGANISM: Hepatitis B Virus

<400> SEQUENCE: 80
tggctcagtt tactagtgcc atttgttcag tg    32

<210> SEQ ID NO 81
<211> LENGTH: 34
<212> TYPE: DNA
<213> ORGANISM: Hepatitis B Virus

<400> SEQUENCE: 81
tggctcagtt tactagtgcc atttgttcag tggt    34

<210> SEQ ID NO 82
<211> LENGTH: 36
<212> TYPE: DNA
<213> ORGANISM: Hepatitis B Virus

<400> SEQUENCE: 82
ggctcagttt actagtgcca tttgttcagt ggttcg    36

<210> SEQ ID NO 83
<211> LENGTH: 42
<212> TYPE: DNA
<213> ORGANISM: Hepatitis B Virus

<400> SEQUENCE: 83
ggctcagttt actagtgcca tttgttcagt ggttcgtagg gc    42

<210> SEQ ID NO 84
<211> LENGTH: 50
<212> TYPE: DNA
<213> ORGANISM: Hepatitis B Virus

<400> SEQUENCE: 84
ggctcagttt actagtgcca tttgttcagt ggttcgtagg gctttccccc    50

<210> SEQ ID NO 85
<211> LENGTH: 33
<212> TYPE: DNA
<213> ORGANISM: Hepatitis B Virus

<400> SEQUENCE: 85
gtgccatttg ttcagtggtt cgtagggctt tcc    33

<210> SEQ ID NO 86
<211> LENGTH: 25
<212> TYPE: DNA
<213> ORGANISM: Hepatitis B Virus

<400> SEQUENCE: 86
gggctttccc ccactctttg gcttt    25

<210> SEQ ID NO 87
<211> LENGTH: 25
<212> TYPE: DNA
<213> ORGANISM: Hepatitis B Virus

<400> SEQUENCE: 87
gggctttccc ccactgtttg gcttt    25

<210> SEQ ID NO 88
<211> LENGTH: 17

```
<212> TYPE: RNA
<213> ORGANISM: Hepatitis B Virus

<400> SEQUENCE: 88
uuccucuuca uccugcu                                                  17

<210> SEQ ID NO 89
<211> LENGTH: 35
<212> TYPE: RNA
<213> ORGANISM: Hepatitis B Virus

<400> SEQUENCE: 89
uuccucuuca uccugcugcu augccucauc uucuu                              35

<210> SEQ ID NO 90
<211> LENGTH: 39
<212> TYPE: RNA
<213> ORGANISM: Hepatitis B Virus

<400> SEQUENCE: 90
uuccucugca uccugcugcu augccucauc uucuuguug                          39

<210> SEQ ID NO 91
<211> LENGTH: 18
<212> TYPE: RNA
<213> ORGANISM: Hepatitis B Virus

<400> SEQUENCE: 91
gccucaucuu cuuguugg                                                 18

<210> SEQ ID NO 92
<211> LENGTH: 35
<212> TYPE: RNA
<213> ORGANISM: Hepatitis B Virus

<400> SEQUENCE: 92
cucaucuucu uguugguucu ucuggacuau caagg                              35

<210> SEQ ID NO 93
<211> LENGTH: 23
<212> TYPE: RNA
<213> ORGANISM: Hepatitis B Virus

<400> SEQUENCE: 93
uugguucuuc uggacuauca agg                                           23

<210> SEQ ID NO 94
<211> LENGTH: 17
<212> TYPE: RNA
<213> ORGANISM: Hepatitis B Virus

<400> SEQUENCE: 94
caagguaugu ugcccgu                                                  17

<210> SEQ ID NO 95
<211> LENGTH: 59
<212> TYPE: DNA
<213> ORGANISM: Hepatitis B Virus

<400> SEQUENCE: 95
ccttgatagt ccagaagaac caacaagaag atgaggcata gcagcaggat gcagaggaa    59

<210> SEQ ID NO 96
```

```
<211> LENGTH: 27
<212> TYPE: DNA
<213> ORGANISM: Bacteriophage T7

<400> SEQUENCE: 96
aatttaatac gactcactat agggaga                                           27

<210> SEQ ID NO 97
<211> LENGTH: 1977
<212> TYPE: DNA
<213> ORGANISM: Hepatitis B Virus

<400> SEQUENCE: 97
gagcucggua cccggggauc cagagucag ggucuguau cuccugcug uggcuccag            60 uucaggaaca guaaacccug cuccgaauau ugccucucac aucucgucaa ucuccgcgag       120
gacuggggac ccugugacga ucauggagaa caucacauca ggauuccuag gaccccugcu      180
cguguuacag gcggguuuu cuuguugac aagaauccuc acaauaccgc agagucuaga        240
cucguggugg acuucucuca auuucuagg gggaucaccc gugugucuug gccaaaauuc       300 gcaguccca accuccaauc acucaccaac cuccugaccu ccaauuuguc cugguuaucg      360
cuggaugugu cugcggcguu uuaucauaaa ggagaacauc cugcacgaag cuugcaucuu      420
cuuauugguu cuucuggauu aucaagguau guugcccguu ugccucuaa uccaggauc       480 aacaacaacc aguacgggac caugcaaaac cugcacgacu ccugcucaag caacucuaa      540 guuucccuca guugcugua caaaaccuac ggauggaaau ugcaccugua uccccauccc     600 aucgccugg gcuucgcaa auaccuaug ggagugggcc ucaguccguu ucucuuggcu       660
caguuuacua ugccauuug uucaguggu cguagggcu ucccccacug uuuggcuuuc      720
agcuauaugg augaugugu auggggggcc aagucuguac agcaucguga gucccuuuau   780
accgcuguua ccaauuuucu uuugucucug gguauacauu uaaacccuaa caaacaaaa    840 agaugggguu auucccuaaa cuucauggcc uacauaauug gaaguggggg aacuuugcca    900
caggaucaua uuguacaaaa gaucaaacac uguuuuagaa aacuuccugu uaacaggccu    960
auugauugga aaguaugcca aagaauugug ggucuuuugg gcuugcugc uccauuuca    1020 caauguggau auccugccuu aaugccuuug uaugcaugua uacaagcuaa acaggcuuc    1080 acuuucgc caacuuacaa ggccuuucua guaaaacagu acaugaaccu uuacccguuu    1140
gcucggcaac ggccuggucu gugccaagug uuugcugacg caacccccac uggcugggc    1200 uuagccauag ccaucagcg caugcgugga accuuugugg cuccucugcc gauccauacu    1260
gcggaacucc uagccgcuug uuuugcucgc agccggucug agcaaagcu caucggaacu    1320 gacaauucug ucguccucuc gcggaaauau acaucauuuc cauggcugcu aggcuguacu    1380
gccaacugga uccuucgcgg gacguccuuu guuuacgucc cgucggcgcu gaaucccgcg    1440 gacgacccu ucggggccg cuugggacuc ucucgucccc uucuccgucu gccguuccag    1500
ccgaccacgg ggcgcaccuc ucuuuacgcg gucucccccgu cugugccuuc ucaucugccg    1560
guccgugugc acuucgcuuc accucugcac guugcauggc gaccaccgug aacgccauc    1620 agauccugcc caaggucuua cauaagagga cucuuggacu cccagcaaug ucaacgaccg    1680
accuugaggc cuacuucaaa gacugugugu uuaaggacug gaggaguug ggggaggaga    1740 uuagguuaau gaucuuugua uuaggaggcu guaggcauaa auuggucugc gcaccagcac    1800
caugcaacuu uuucaccucu gccuaaucau ucuuugacca ugucccacug uucaagcccuc   1860 caagcugugc cuugggugc uuuggggcau ggacauugac ccuuauaaag aauuuggagc    1920
```

```
uacuguggag uuacucucgu uuuugccuuc ugacuucuuu ccuuccguac gagaucc      1977

<210> SEQ ID NO 98
<211> LENGTH: 23
<212> TYPE: DNA
<213> ORGANISM: HIV-1

<400> SEQUENCE: 98
cgggcgccac tgctagagat ttt                                          23

<210> SEQ ID NO 99
<211> LENGTH: 28
<212> TYPE: DNA
<213> ORGANISM: HIV-1

<400> SEQUENCE: 99
gtttgtatgt ctgttgctat tatgtcta                                     28

<210> SEQ ID NO 100
<211> LENGTH: 50
<212> TYPE: DNA
<213> ORGANISM: Artificial Sequence
<220> FEATURE:
<223> OTHER INFORMATION: HIV-specific promoter-primer

<400> SEQUENCE: 100
aatttaatac gactcactat agggagacgg gcgccactgc tagagatttt             50

<210> SEQ ID NO 101
<211> LENGTH: 55
<212> TYPE: DNA
<213> ORGANISM: Artificial Sequence
<220> FEATURE:
<223> OTHER INFORMATION: HIV-specific promoter-primer

<400> SEQUENCE: 101
aatttaatac gactcactat agggagagtt tgtatgtctg ttgctattat gtcta       55

<210> SEQ ID NO 102
<211> LENGTH: 18
<212> TYPE: DNA
<213> ORGANISM: HIV-1

<400> SEQUENCE: 102
gcctcaataa agcttgcc                                                18

<210> SEQ ID NO 103
<211> LENGTH: 19
<212> TYPE: DNA
<213> ORGANISM: HIV-1

<400> SEQUENCE: 103
acagcagtac aaatggcag                                               19

<210> SEQ ID NO 104
<211> LENGTH: 20
<212> TYPE: DNA
<213> ORGANISM: HIV-1

<400> SEQUENCE: 104
gacagcagta caaatggcag                                              20

<210> SEQ ID NO 105
```

```
<211> LENGTH: 21
<212> TYPE: DNA
<213> ORGANISM: HIV-1

<400> SEQUENCE: 105
agacagcagt acaaatggca g                                             21

<210> SEQ ID NO 106
<211> LENGTH: 22
<212> TYPE: DNA
<213> ORGANISM: HIV-1

<400> SEQUENCE: 106
ccacaatttt aaagaaaaag gg                                            22

<210> SEQ ID NO 107
<211> LENGTH: 20
<212> TYPE: RNA
<213> ORGANISM: HIV-1
<220> FEATURE:
<221> NAME/KEY: modified_base
<222> LOCATION: (7)...(7)
<223> OTHER INFORMATION: I

<400> SEQUENCE: 107
cugguancua gagaucccuc                                               20

<210> SEQ ID NO 108
<211> LENGTH: 19
<212> TYPE: DNA
<213> ORGANISM: HIV-1
<220> FEATURE:
<221> NAME/KEY: modified_base
<222> LOCATION: (8)...(8)
<223> OTHER INFORMATION: I
<221> NAME/KEY: modified_base
<222> LOCATION: (9)...(9)
<223> OTHER INFORMATION: I
<221> NAME/KEY: modified_base
<222> LOCATION: (10)...(10)
<223> OTHER INFORMATION: I

<400> SEQUENCE: 108
ggattggnnn gtacagtgc                                                19

<210> SEQ ID NO 109
<211> LENGTH: 24
<212> TYPE: RNA
<213> ORGANISM: HIV-1

<400> SEQUENCE: 109
ccacaagcuu agaagauaga gagg                                          24

<210> SEQ ID NO 110
<211> LENGTH: 15
<212> TYPE: DNA
<213> ORGANISM: HIV-1

<400> SEQUENCE: 110
ggatctctag ctacc                                                    15

<210> SEQ ID NO 111
<211> LENGTH: 22
<212> TYPE: DNA
<213> ORGANISM: HIV-1

<400> SEQUENCE: 111
```

```
cccttttctt ttaaaattgt gg                                            22

<210> SEQ ID NO 112
<211> LENGTH: 16
<212> TYPE: DNA
<213> ORGANISM: HIV-1

<400> SEQUENCE: 112
ctatcttcta agcttg                                                   16

<210> SEQ ID NO 113
<211> LENGTH: 21
<212> TYPE: RNA
<213> ORGANISM: HIV-1

<400> SEQUENCE: 113
acugacgcuc ucgcacccau c                                             21

<210> SEQ ID NO 114
<211> LENGTH: 24
<212> TYPE: RNA
<213> ORGANISM: HIV-1

<400> SEQUENCE: 114
ucugcugucc cuguaauaaa cccg                                          24

<210> SEQ ID NO 115
<211> LENGTH: 28
<212> TYPE: DNA
<213> ORGANISM: Hepatitis C Virus
<220> FEATURE:
<221> NAME/KEY: modified_base
<222> LOCATION: (21)...(21)
<223> OTHER INFORMATION: I

<400> SEQUENCE: 115
agtaccacaa ggcctttcgc nacccaac                                      28

<210> SEQ ID NO 116
<211> LENGTH: 55
<212> TYPE: DNA
<213> ORGANISM: Artificial Sequence
<220> FEATURE:
<223> OTHER INFORMATION: HCV-specific promoter-primer
<221> NAME/KEY: modified_base
<222> LOCATION: (48)...(48)
<223> OTHER INFORMATION: I

<400> SEQUENCE: 116
aatttaatac gactcactat agggagaagt accacaaggc ctttcgcnac ccaac        55

<210> SEQ ID NO 117
<211> LENGTH: 18
<212> TYPE: DNA
<213> ORGANISM: Hepatitis C Virus

<400> SEQUENCE: 117
ctagccatgg cgttagta                                                 18

<210> SEQ ID NO 118
<211> LENGTH: 23
<212> TYPE: DNA
<213> ORGANISM: Hepatitis C Virus

<400> SEQUENCE: 118
```

```
ctactgtctt cacgcagaaa gcg                                              23
```

<210> SEQ ID NO 119
<211> LENGTH: 22
<212> TYPE: RNA
<213> ORGANISM: Hepatitis C Virus
<220> FEATURE:
<221> NAME/KEY: modified_base
<222> LOCATION: (22)...(22)
<223> OTHER INFORMATION: t
<221> NAME/KEY: misc_feature
<222> LOCATION: (1)...(21)
<223> OTHER INFORMATION: 2'-OMe nucleotide analogs

<400> SEQUENCE: 119

```
cccgggagag ccauaguggu cn                                               22
```

<210> SEQ ID NO 120
<211> LENGTH: 19
<212> TYPE: DNA
<213> ORGANISM: Hepatitis C Virus

<400> SEQUENCE: 120

```
ctgcggaacc ggtgagtac                                                   19
```

<210> SEQ ID NO 121
<211> LENGTH: 19
<212> TYPE: DNA
<213> ORGANISM: Hepatitis C Virus

<400> SEQUENCE: 121

```
agccuccagg acccccct                                                    19
```

<210> SEQ ID NO 122
<211> LENGTH: 14
<212> TYPE: DNA
<213> ORGANISM: Hepatitis C Virus

<400> SEQUENCE: 122

```
gaccactatg gctc                                                        14
```

<210> SEQ ID NO 123
<211> LENGTH: 14
<212> TYPE: DNA
<213> ORGANISM: Hepatitis C Virus

<400> SEQUENCE: 123

```
gtactcaccg gttc                                                        14
```

<210> SEQ ID NO 124
<211> LENGTH: 19
<212> TYPE: RNA
<213> ORGANISM: Hepatitis C Virus

<400> SEQUENCE: 124

```
gggcacucgc aagcacccu                                                   19
```

<210> SEQ ID NO 125
<211> LENGTH: 18
<212> TYPE: RNA
<213> ORGANISM: Hepatitis C Virus

<400> SEQUENCE: 125

```
cauggugcac ggucuacg                                                    18
```

```
<210> SEQ ID NO 126
<211> LENGTH: 35
<212> TYPE: DNA
<213> ORGANISM: Hepatitis B Virus

<400> SEQUENCE: 126
aagaagatga ggcatagcag caggatgaag aggaa                              35

<210> SEQ ID NO 127
<211> LENGTH: 18
<212> TYPE: RNA
<213> ORGANISM: Hepatitis B Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 127
gaagaugagg cauagcag                                                 18

<210> SEQ ID NO 128
<211> LENGTH: 20
<212> TYPE: RNA
<213> ORGANISM: Hepatitis B Virus
<220> FEATURE:
<221> NAME/KEY: misc_feature
<222> LOCATION: (1)...(20)
<223> OTHER INFORMATION: 2'-OMe nucleotide analogs

<400> SEQUENCE: 128
aagaagauga ggcauagcag                                               20

<210> SEQ ID NO 129
<211> LENGTH: 18
<212> TYPE: RNA
<213> ORGANISM: Hepatitis B Virus
<220> FEATURE:
<221> NAME/KEY: misc_feature
<222> LOCATION: (1)...(18)
<223> OTHER INFORMATION: 2'-OMe nucleotide analogs

<400> SEQUENCE: 129
cagcaggaug aagaggaa                                                 18

<210> SEQ ID NO 130
<211> LENGTH: 14
<212> TYPE: RNA
<213> ORGANISM: Hepatitis B Virus
<220> FEATURE:
<221> NAME/KEY: misc_feature
<222> LOCATION: (1)...(14)
<223> OTHER INFORMATION: 2'-OMe nucleotide analogs

<400> SEQUENCE: 130
caggaugaag agga                                                     14

<210> SEQ ID NO 131
<211> LENGTH: 12
<212> TYPE: RNA
<213> ORGANISM: Hepatitis B Virus
<220> FEATURE:
<221> NAME/KEY: misc_feature
<222> LOCATION: (1)...(12)
<223> OTHER INFORMATION: 2'-OMe nucleotide analogs

<400> SEQUENCE: 131
aagaagauga gg                                                       12
```

-continued

```
<210> SEQ ID NO 132
<211> LENGTH: 16
<212> TYPE: RNA
<213> ORGANISM: Hepatitis B Virus
<220> FEATURE:
<221> NAME/KEY: misc_feature
<222> LOCATION: (1)...(16)
<223> OTHER INFORMATION: 2'-OMe nucleotide analogs

<400> SEQUENCE: 132
gaagaugagg cauagc                                                     16

<210> SEQ ID NO 133
<211> LENGTH: 14
<212> TYPE: RNA
<213> ORGANISM: Hepatitis B Virus
<220> FEATURE:
<221> NAME/KEY: misc_feature
<222> LOCATION: (1)...(14)
<223> OTHER INFORMATION: 2'-OMe nucleotide analogs

<400> SEQUENCE: 133
gaagaugagg caua                                                       14

<210> SEQ ID NO 134
<211> LENGTH: 16
<212> TYPE: RNA
<213> ORGANISM: HIV-1
<220> FEATURE:
<221> NAME/KEY: misc_feature
<222> LOCATION: (1)...(16)
<223> OTHER INFORMATION: 2'-OMe nucleotide analogs

<400> SEQUENCE: 134
ggguacagug cagggg                                                     16

<210> SEQ ID NO 135
<211> LENGTH: 28
<212> TYPE: RNA
<213> ORGANISM: HIV-1
<220> FEATURE:
<221> NAME/KEY: misc_feature
<222> LOCATION: (1)...(28)
<223> OTHER INFORMATION: 2'-OMe nucleotide analogs

<400> SEQUENCE: 135
ccgagagggu acagugcagg ggucucgg                                        28

<210> SEQ ID NO 136
<211> LENGTH: 19
<212> TYPE: RNA
<213> ORGANISM: HIV-1
<220> FEATURE:
<221> NAME/KEY: misc_feature
<222> LOCATION: (1)...(19)
<223> OTHER INFORMATION: 2'-OMe nucleotide analogs

<400> SEQUENCE: 136
agggguacag ugcaggggu                                                  19

<210> SEQ ID NO 137
<211> LENGTH: 17
<212> TYPE: DNA
<213> ORGANISM: HIV-1

<400> SEQUENCE: 137
ggggtacagt gcagggg                                                    17
```

```
<210> SEQ ID NO 138
<211> LENGTH: 10
<212> TYPE: RNA
<213> ORGANISM: Hepatitis C Virus
<220> FEATURE:
<221> NAME/KEY: misc_feature
<222> LOCATION: (1)...(10)
<223> OTHER INFORMATION: 2'-OMe nucleotide analogs

<400> SEQUENCE: 138
aaccggugag                                                              10

<210> SEQ ID NO 139
<211> LENGTH: 14
<212> TYPE: RNA
<213> ORGANISM: Hepatitis C Virus
<220> FEATURE:
<221> NAME/KEY: misc_feature
<222> LOCATION: (1)...(14)
<223> OTHER INFORMATION: 2'-OMe nucleotide analogs

<400> SEQUENCE: 139
uacaccggaa uugc                                                         14

<210> SEQ ID NO 140
<211> LENGTH: 13
<212> TYPE: RNA
<213> ORGANISM: Hepatitis C Virus
<220> FEATURE:
<221> NAME/KEY: misc_feature
<222> LOCATION: (1)...(13)
<223> OTHER INFORMATION: 2'-OMe nucleotide analogs

<400> SEQUENCE: 140
uaguaugagu guc                                                          13

<210> SEQ ID NO 141
<211> LENGTH: 86
<212> TYPE: DNA
<213> ORGANISM: Hepatitis C Virus

<400> SEQUENCE: 141
tagtatgagt gtcgtgcagc ctccaggacc cccctcccg ggagagccat agtggtctgc        60
ggaaccggtg agtacaccgg aattgc                                            86

<210> SEQ ID NO 142
<211> LENGTH: 46
<212> TYPE: DNA
<213> ORGANISM: Hepatitis B Virus

<400> SEQUENCE: 142
aggacaaacg ggcaacatac cttgataatc cagaagaacc aataag                      46
```

COMPOSITIONS AND METHODS FOR DETECTING HEPATITIS B VIRUS

CROSS-REFERENCE TO RELATED APPLICATIONS

This application is a continuation of U.S. application Ser. No. 11/872,538, now U.S. Pat. No. 7,785,844, which is a continuation of U.S. patent application Ser. No. 10/461,790, filed Jun. 13, 2003, abandoned, which claims the benefit of U.S. Provisional Application No. 60/389,393, filed Jun. 14, 2002. The entire disclosures of these prior applications are hereby incorporated by reference.

GOVERNMENT INTEREST IN THE INVENTION

Certain aspects of the invention disclosed herein were made with government support under contracts N01-HB-67130 and N01-HB-07148 with the National Heart, Lung and Blood Institute of the National Institutes of Health. The United States government has certain rights in these aspects of the invention.

FIELD OF THE INVENTION

The present invention relates to the field of biotechnology. More specifically, the invention relates to diagnostic assays for detecting the nucleic acids of any or all of hepatitis B virus, human immunodeficiency virus type 1, and hepatitis C virus.

BACKGROUND OF THE INVENTION

Infection by the hepatitis B virus (HBV) occurs worldwide and is an important cause of both acute and chronic viral hepatitis. HBV is a partially double-stranded circular DNA virus having a viral particle size of 42 nm. This particle includes an outer lipoprotein coat and the hepatitis B surface antigen (HBsAg). The HBsAg, circulates in the blood as a viral particle-bound form, or as a free, noninfectious protein aggregated into 22-nm spherical and tubular particles. Transmission of HBV is mediated primarily through blood and/or sexual contact. The incubation period for this virus ranges as high as 180 days (Gitlin, *Clin. Chem.* 43:1500 (1997)).

The HBsAg, which can be detected from 2 to 12 weeks after infection with HBV, is the first serologic marker of HBV infection. The presence of this marker often precedes symptoms or abnormalities of hepatic biochemistry by 6-8 weeks. Antibodies specific for the hepatitis B core antigen, which is contained within the viral particle, usually appear 2 weeks after the detection of HBsAg, and remain detectable for up to 6 months after the onset of the acute hepatitis (Gitlin, Supra).

The risk of hepatitis virus transmission from transfusions has declined dramatically since post-transfusion hepatitis (PTH) was first recognized in the 1940s. For example, in 1970 scientists at the NIH reported the results of a prospective study to determine the incidence of icteric and anicteric hepatitis in patients that had undergone open-heart surgery and received blood from commercial or volunteer blood donors. Icteric and anicteric hepatitis developed in 51% of the recipients of commercial blood, but in none of the patients who received blood from volunteer donors.

It was also revealed in 1970 at an NIH Conference that the "Australia" antigen (now known as the hepatitis B surface antigen) was part of an infectious agent, presumably a hepatitis virus. Only a couple of years later, the simultaneous exclusion of commercial blood and HBsAg-positive donors reduced the incidence of PTH to about 7% of the prior rate (Tobler et al., *Clin. Chem.* 43:1487 (1997)). These measures dramatically improved the safety of the donated blood supply.

Nucleic acid testing has more recently been undertaken to increase assay sensitivity, thereby ensuring an even higher level of safety for the supply of donated blood. Assays and reagents for detecting HBV have been previously disclosed in, for example, U.S. Pat. Nos. 5,780,219 and 4,562,159; and in published International Patent Application Nos. WO94/08032 and WO95/02690.

SUMMARY OF THE INVENTION

A first aspect of the invention relates to a capture oligonucleotide composition that includes a polynucleotide that has a length of up to 100 nucleotides, and includes an HBV-complementary sequence that is either 20 contiguous nucleotides of SEQ ID NO:68, or 25 contiguous nucleotides of SEQ ID NO:69. Further, the polynucleotide is immobilized to a solid support. In one embodiment of the invention, the solid support is a paramagnetic particle. In another embodiment, the polynucleotide further includes a first homopolymeric sequence, the solid support is a paramagnetic particle covalently linked to a second homopolymeric sequence, and the polynucleotide is immobilized to the solid support by complementary base pairing between the first homopolymeric sequence and the second homopolymeric sequence. In still another embodiment, the HBV-complementary sequence of the polynucleotide is any of SEQ ID NOs:70-76. More preferably, the HBV-complementary sequence of the polynucleotide is SEQ ID NO:73. In still another embodiment, the HBV-complementary sequence of the polynucleotide is any of SEQ ID NOs:77-87. More preferably, the HBV-complementary sequence of the polynucleotide is SEQ ID NOs:80 or 87.

A second aspect of the invention relates to a kit for detecting HBV target nucleic acids. In this instance the invented kit includes at least one capture oligonucleotide of up to 100 nucleotides in length and including an HBV-complementary sequence of at least 20 contiguous nucleotides of SEQ ID NO:68 or a sequence of at least 25 contiguous nucleotides of SEQ ID NO:69. This capture oligonucleotide is immobilized to a solid support. The kit further includes at least one first strand primer that includes a downstream HBV-complementary sequence, and optionally a first strand primer upstream sequence that is not complementary to HBV nucleic acids. The downstream HBV-complementary sequence of first strand primer consists of 20-50 contiguous bases contained within SEQ ID NO:2, allowing for the presence of RNA and DNA equivalents and nucleotide analogs. Still further, the kit includes at least one second strand primer that includes a downstream HBV-complementary sequence, and optionally a second strand primer upstream sequence that is not complementary to HBV nucleic acids. The downstream HBV-complementary sequence of the second strand primer consists of 20-54 contiguous bases contained within the sequence of SEQ ID NO:4, allowing for the presence of RNA and DNA equivalents and nucleotide analogs. In one embodiment of the invention, the downstream HBV-complementary sequence of the at least one first strand primer can be any of SEQ ID NOs:22-28. More preferably, the at least one capture oligonucleotide is any of SEQ ID NO:73, SEQ ID NO:80 and SEQ ID NO:87. More generally, and with respect to primers contained in the kit, the first strand primer upstream sequence that is not complementary to HBV nucleic acids can be a promoter sequence for an RNA polymerase. In another embodiment, the downstream HBV-complementary sequence of the at least one first strand primer can be any of SEQ ID NOs:22-28. In still another embodiment, the downstream HBV-complementary sequence of the at least one second strand primer is any of SEQ ID NOs:5-15. When the downstream HBV-complementary sequence of the at least one first strand primer is any of SEQ ID NOs:22-28, the downstream HBV-complementary sequence of the at least one second strand primer is preferably any of SEQ ID NOs:5-15. In an alternative embodiment, when the downstream HBV-complementary sequence of the at least one first strand primer is any of SEQ ID NOs:22-28, the downstream HBV-complementary sequence of the at least one second strand primer is preferably any of SEQ ID NOs:5-15. According to a different embodiment, the invented kit further includes at least one detectably labeled probe that hybridizes to an amplicon produced in an amplification reaction using the invented first and second strand primers. Preferred probes have lengths of up to 23 nucleotides, and sequences of at least 17 contiguous nucleotides contained in the sequence of SEQ ID NO:95 or the complement thereof, allowing for the presence of RNA and DNA equivalents and nucleotide analogs. More preferably, the detectably labeled probe is any of SEQ ID NOs:50-66. In an alternative embodiment, when the downstream HBV-complementary sequence of the first strand primer is any of SEQ ID NOs:22-28, and when the downstream HBV-complementary sequence of the second strand primer is any of SEQ ID NOs:5-15, there is further included at least one detectably labeled probe having a sequence that is any of SEQ ID NOs:50-66. When the invented kit includes at least one detectably labeled probe that hybridizes to an amplicon produced in an amplification reaction using the invented first and second strand primers, the probe can be a molecular beacon that includes a target-complementary loop sequence of nucleotides. This target-complementary loop sequence of nucleotides is preferably a sequence of 12-20 contiguous nucleotides contained within the sequence of SEQ ID NO:126. More preferably, the target-complementary loop sequence of nucleotides is any of SEQ ID NOs:127-133. Generally speaking, the at least one second strand primer of the invented kit may include two second strand primers. When this is the case, the at least one first strand primer preferably is any of SEQ ID NO:22, SEQ ID NO:23, SEQ ID NO:26 and SEQ ID NO:27. Generally speaking, the at least one first strand primer of the invented kit may include two first strand primers, and the at least one second strand primer may include two second strand primers. In a highly preferred embodiment of this kit, there is further included an HBV pseudo target that comprises RNA.

A third aspect of the invention also relates to a kit for amplifying HBV target nucleic acids that may be present in a biological sample. This kit includes a first strand primer that includes a downstream HBV-complementary sequence, and optionally a first strand primer upstream sequence that is not complementary to HBV nucleic acids. The downstream HBV-complementary sequence of the first strand primer consists of 20-50 contiguous bases contained within SEQ ID NO:2, allowing for the presence of RNA and DNA equivalents and nucleotide analogs. The kit also contains a second strand primer that includes a downstream HBV-complementary sequence, and optionally a second strand primer upstream sequence that is not complementary to HBV nucleic acids. The downstream HBV-complementary sequence of the second strand primer consists of 20-54 contiguous bases contained within the sequence of SEQ ID NO:4, allowing for the presence of RNA and DNA equivalents and nucleotide analogs. In a particular embodiment of the invention, the first strand primer upstream sequence is a promoter sequence for an RNA polymerase. In certain other embodiments, the downstream HBV-complementary sequence of the first strand primer consists of 20-24 contiguous bases contained within SEQ ID NO:2. In a more preferred embodiment, the downstream HBV-complementary sequence of the first strand primer is any of SEQ ID NOs:22-28, or still more preferably any of SEQ ID NO:22, SEQ ID NO:23, SEQ ID NO:26 or SEQ ID NO:27. In certain specific embodiments of the invention, the downstream HBV-complementary sequence of the second strand primer is any of SEQ ID NOs:5-15, or still more preferably either SEQ ID NO:11 or SEQ ID NO:15. In accordance with another embodiment, when the downstream HBV-complementary sequence of the first strand primer is any of SEQ ID NO:22, SEQ ID NO:23, SEQ ID NO:26 or SEQ ID NO:27, the downstream HBV-complementary sequence of the second strand primer is preferably any of SEQ ID NOs:5-15. When this is the case, the downstream HBV-complementary sequence of the second strand primer is preferably either SEQ ID NO:11 and SEQ ID NO:15. In a highly preferred embodiment of this invention, the kit further includes at least one detectably labeled probe that hybridizes to an HBV amplicon which is produced in an amplification reaction carried out using the first strand primer and the second strand primer. In a still more highly preferred embodiment, the detectably labeled probe includes the sequence of SEQ ID NO:50 or the complement thereof, SEQ ID NO:57 or the complement thereof, or SEQ ID NO:55 or the complement of thereof. In an alternative embodiment, the detectably labeled probe is a molecular beacon that includes a target-complementary loop sequence of nucleotides. This target-complementary loop sequence of nucleotides typically consists of 12-20 contiguous nucleotides contained in the sequence of SEQ ID NO:126 or the complement thereof, allowing for the presence of nucleotide analogs and RNA and DNA equivalent bases. In a different embodiment, the kit includes an additional first strand primer. In a preferred embodiment, when the kit includes an additional first strand primer, the downstream HBV-complementary sequence of the second strand primer has the sequence of SEQ ID NO:11 or SEQ ID NO:15. In still a different embodiment, the kit further includes an additional second strand primer. For example, when the kit includes an additional second strand primer, the downstream HBV-complementary sequence of the first strand primer is preferably any of SEQ ID NO:22, SEQ ID NO:23, SEQ ID NO:26 or SEQ ID NO:27. In still a different embodiment, the kit further includes both an additional first strand primer and an additional second strand primer. This embodiment is illustrated by a kit wherein the downstream HBV-complementary sequence of the first strand primer includes SEQ ID NO:22, wherein the additional first strand primer includes SEQ ID NO:23, wherein the downstream HBV-complementary sequence of the second strand primer includes SEQ ID NO:15, and wherein the additional second strand primer includes SEQ ID NO:11. In a highly preferred embodiment of this kit, there is further included an HBV pseudo target that is made of RNA. In another embodiment, when the kit further includes both an additional first strand primer and an additional second strand primer, the downstream HBV-complementary sequence of the first strand primer can include SEQ ID NO:23, the additional first strand primer can include SEQ ID NO:26, the downstream HBV-complementary sequence of the second strand primer can include SEQ ID NO:15, and the additional second strand primer can include SEQ ID NO:11. In another embodiment, when the kit further includes both an additional first strand primer and an additional second strand primer, the downstream HBV-complementary sequence of the first strand primer can include SEQ ID NO:24, the additional first strand primer can include SEQ ID NO:17, the second strand primer can include SEQ ID NO:15, and the additional second strand primer can include SEQ ID NO:5. In another embodiment, when the kit further includes both an additional first strand primer and an additional second strand primer, the first strand primer can include SEQ ID NO:24, the additional first strand primer can include SEQ ID NO:20, the second strand primer can include SEQ ID NO:15, and the additional second strand primer can include SEQ ID NO:5. Generally speaking, kits in accordance with the invention can further include either or both of primers for amplifying an HIV-1 target nucleic acid, and primers for amplifying an HCV target nucleic acid.

DEFINITIONS

The following terms have the following meanings for the purposes of this disclosure, unless expressly stated to the contrary herein.

As used herein, a "biological sample" is any tissue or polynucleotide-containing material obtained from a human. Biological samples in accordance with the invention include peripheral blood, plasma, serum, bone marrow, biopsy tissue including lymph nodes, respiratory tissue or exudates, gastrointestinal tissue, cervical swab samples, semen or other body fluids, tissues or materials. A biological sample may be treated to disrupt tissue or cell structure, thereby releasing intracellular components into a solution which may contain enzymes, buffers, salts, detergents and the like.

As used herein, "polynucleotide" means either RNA or DNA, along with any synthetic nucleotide analogs or other molecules that may be present in the sequence and that do not prevent hybridization of the polynucleotide with a second molecule having a complementary sequence. The term includes polymers containing analogs of naturally occurring nucleotides and particularly includes analogs having a methoxy group at the 2' position of the ribose (OMe).

As used herein, a "detectable label" is a chemical species that can be detected or can lead to a detectable response. Detectable labels in accordance with the invention can be linked to polynucleotide probes either directly or indirectly, and include radioisotopes, enzymes, haptens, chromophores such as dyes or particles that impart a detectable color (e.g., latex beads or metal particles), luminescent compounds (e.g., bioluminescent, phosphorescent or chemiluminescent moieties) and fluorescent compounds.

A "homogeneous detectable label" refers to a label that can be detected in a homogeneous fashion by determining whether the label is on a probe hybridized to a target sequence. That is, homogeneous detectable labels can be detected without physically removing hybridized from unhybridized forms of the label or labeled probe. These labels have been described in detail by Arnold et al., U.S. Pat. No. 5,283, 174; Woodhead et al., U.S. Pat. No. 5,656,207; and Nelson et al., U.S. Pat. No. 5,658,737. Preferred labels for use in homogenous assays include chemiluminescent compounds (e.g., see Woodhead et al., U.S. Pat. No. 5,656,207; Nelson et al., U.S. Pat. No. 5,658,737; and Arnold, Jr., et al., U.S. Pat. No. 5,639,604). Preferred chemiluminescent labels are acridinium ester ("AE") compounds, such as standard AE or derivatives thereof (e.g., naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE).

As used herein, "amplification" refers to an in vitro procedure for obtaining multiple copies of a target nucleic acid sequence, its complement or fragments thereof.

By "target nucleic acid" or "target" is meant a nucleic acid containing a target nucleic acid sequence.

By "target nucleic acid sequence," "target nucleotide sequence," "target sequence" or "target region" is meant a specific deoxyribonucleotide or ribonucleotide sequence comprising all or part of the nucleotide sequence of a single-stranded nucleic acid molecule, and the deoxyribonucleotide or ribonucleotide sequence complementary thereto.

By "transcription associated amplification" is meant any type of nucleic acid amplification that uses an RNA polymerase to produce multiple RNA transcripts from a nucleic acid template. One example of a transcription associated amplification method, called "Transcription Mediated Amplification" (TMA), generally employs an RNA polymerase, a DNA polymerase, deoxyribonucleoside triphosphates, ribonucleoside triphosphates, and a promoter-template complementary oligonucleotide, and optionally may include one or more analogous oligonucleotides. Variations of TMA are well known in the art as disclosed in detail in Burg et al., U.S. Pat. No. 5,437,990; Kacian et al., U.S. Pat. Nos. 5,399,491 and 5,554,516; Kacian et al., PCT No. WO 93/22461; Gingeras et al., PCT No. WO 88/01302; Gingeras et al., PCT No. WO 88/10315; Malek et al., U.S. Pat. No. 5,130,238; Urdea et al., U.S. Pat. Nos. 4,868,105 and 5,124, 246; McDonough et al., PCT No. WO 94/03472; and Ryder et al., PCT No. WO 95/03430. The methods of Kacian et al. are preferred for conducting nucleic acid amplification procedures of the type disclosed herein.

As used herein, an "oligonucleotide" or "oligomer" is a polymeric chain of at least two, generally between about five and about 100, chemical subunits, each subunit comprising a nucleotide base moiety, a sugar moiety, and a linking moiety that joins the subunits in a linear spatial configuration. Common nucleotide base moieties are guanine (G), adenine (A), cytosine (C), thymine (T) and uracil (U), although other rare or modified nucleotide bases able to hydrogen bond are well known to those skilled in the art. Oligonucleotides may optionally include analogs of any of the sugar moieties, the base moieties, and the backbone constituents. Preferred oligonucleotides of the present invention fall in a size range of about 10 to about 60 residues. Oligonucleotides may be purified from naturally occurring sources, but preferably are synthesized using any of a variety of well known enzymatic or chemical methods.

As used herein, a "probe" is an oligonucleotide that hybridizes specifically to a target sequence in a nucleic acid, preferably in an amplified nucleic acid, under conditions that promote hybridization, to form a detectable hybrid. A probe may contain a detectable moiety which either may be attached to the end(s) of the probe or may be internal. The nucleotides of the probe which combine with the target polynucleotide need not be strictly contiguous, as may be the case with a detectable moiety internal to the sequence of the probe. Detection may either be direct (i.e., resulting from a probe hybridizing directly to the target sequence or amplified nucleic acid) or indirect (i.e., resulting from a probe hybridizing to an intermediate molecular structure that links the probe to the target sequence or amplified nucleic acid). The "target" of a probe generally refers to a sequence contained within an amplified nucleic acid sequence which hybridizes specifically to at least a portion of a probe oligonucleotide using standard hydrogen bonding (i.e., base pairing). A probe may comprise target-specific sequences and other sequences that contribute to three-dimensional conformation of the probe (e.g., as described in Lizardi et al., U.S. Pat. Nos. 5,118,801 and 5,312,728). Sequences that are "sufficiently complementary" allow stable hybridization of a probe oligonucleotide to a target sequence that is not completely complementary to the probe's target-specific sequence.

As used herein, an "amplification primer" is an oligonucleotide that hybridizes to a target nucleic acid, or its complement, and participates in a nucleic acid amplification reaction. Amplification primers, or more simply "primers," may be an optionally modified oligonucleotide which is capable of hybridizing to a template nucleic acid and which has a 3' end that can be extended by a DNA polymerase activity.

By "substantially homologous," "substantially corresponding" or "substantially corresponds" is meant that the subject oligonucleotide has a base sequence containing an at least 10 contiguous base region that is at least 70% homologous, preferably at least 80% homologous, more preferably at least 90% homologous, and most preferably 100% homologous to an at least 10 contiguous base region present in a reference base sequence (excluding RNA and DNA equivalents). Those skilled in the art will readily appreciate modifications that could be made to the hybridization assay conditions at various percentages of homology to permit hybridization of the oligonucleotide to the target sequence while preventing unacceptable levels of non-specific hybridization. The degree of similarity is determined by comparing the order of nucleobases making up the two sequences and does not take into consideration other structural differences which may exist between the two sequences, provided the structural differences do not prevent hydrogen bonding with complementary bases. The degree of homology between two sequences can also be expressed in terms of the number of base mismatches present in each set of at least 10 contiguous bases being compared, which may range from 0-2 base differences.

By "substantially complementary" is meant that the subject oligonucleotide has a base sequence containing an at least 10 contiguous base region that is at least 70% complementary, preferably at least 80% complementary, more preferably at least 90% complementary, and most preferably 100% complementary to an at least 10 contiguous base region present in a target nucleic acid sequence (excluding RNA and DNA equivalents). (Those skilled in the art will readily appreciate modifications that could be made to the hybridization assay conditions at various percentages of complementarity to permit hybridization of the oligonucleotide to the target sequence while preventing unacceptable levels of non-specific hybridization.) The degree of complementarity is determined by comparing the order of nucleobases making up the two sequences and does not take into consideration other structural differences which may exist between the two sequences, provided the structural differences do not prevent hydrogen bonding with complementary bases. The degree of complementarity between two sequences can also be expressed in terms of the number of base mismatches present in each set of at least 10 contiguous bases being compared, which may range from 0-2 base mismatches.

By "sufficiently complementary" is meant a contiguous nucleic acid base sequence that is capable of hybridizing to another base sequence by hydrogen bonding between a series of complementary bases. Complementary base sequences may be complementary at each position in the base sequence of an oligonucleotide using standard base pairing (e.g., G:C, A:T or A:U pairing) or may contain one or more residues that are not complementary using standard hydrogen bonding (including abasic "nucleotides"), but in which the entire complementary base sequence is capable of specifically hybridizing with another base sequence in appropriate hybridization conditions. Contiguous bases are preferably at least about 80%, more preferably at least about 90%, and most preferably about 100% complementary to a sequence to which an oligonucleotide is intended to specifically hybridize. Appropriate hybridization conditions are well known to those skilled in the art, can be predicted readily based on base sequence composition, or can be determined empirically by using routine testing (e.g., See Sambrook et al., *Molecular Cloning, A Laboratory Manual*, $2^{nd}$ ed. (Cold Spring Harbor Laboratory Press, Cold Spring Harbor, N.Y., 1989) at §§1.90-1.91, 7.37-7.57, 9.47-9.51 and 11.47-11.57 particularly at §§9.50-9.51, 11.12-11.13, 11.45-11.47 and 11.55-11.57).

By "capture oligonucleotide" is meant at least one nucleic acid oligonucleotide that provides means for specifically joining a target sequence and an immobilized oligonucleotide due to base pair hybridization. A capture oligonucleotide preferably includes two binding regions: a target sequence-binding region and an immobilized probe-binding region, usually contiguous on the same oligonucleotide, although the capture oligonucleotide may include a target sequence-binding region and an immobilized probe-binding region which are present on two different oligonucleotides joined together by one or more linkers. For example, an immobilized probe-binding region may be present on a first oligonucleotide, the target sequence-binding region may be present on a second oligonucleotide, and the two different oligonucleotides are joined by hydrogen bonding with a linker that is a third oligonucleotide containing sequences that hybridize specifically to the sequences of the first and second oligonucleotides.

By "immobilized probe" or "immobilized nucleic acid" is meant a nucleic acid that joins, directly or indirectly, a capture oligonucleotide to an immobilized support. An immobilized probe is an oligonucleotide joined to a solid support that facilitates separation of bound target sequence from unbound material in a sample.

By "separating" or "purifying" is meant that one or more components of the biological sample are removed from one or more other components of the sample. Sample components include nucleic acids in a generally aqueous solution phase which may also include materials such as proteins, carbohydrates, lipids and labeled probes. Preferably, the separating or purifying step removes at least about 70%, more preferably at least about 90% and, even more preferably, at least about 95% of the other components present in the sample.

By "RNA and DNA equivalents" or "RNA and DNA equivalent bases" is meant RNA and DNA molecules having the same complementary base pair hybridization properties. RNA and DNA equivalents have different sugar moieties (i.e., ribose versus deoxyribose) and may differ by the presence of uracil in RNA and thymine in DNA. The differences between RNA and DNA equivalents do not contribute to differences in homology because the equivalents have the same degree of complementarity to a particular sequence.

By "consisting essentially of" is meant that additional component(s), composition(s) or method step(s) that do not materially change the basic and novel characteristics of the present invention may be included in the compositions or kits or methods of the present invention. Such characteristics include the ability to selectively detect HBV nucleic acids in biological samples such as whole blood or plasma, at about 100 copies of the HBV nucleic acid. Any component(s), composition(s), or method step(s) that have a material effect on the basic and novel characteristics of the present invention would fall outside of this term.

DETAILED DESCRIPTION OF THE INVENTION

Figure 1:
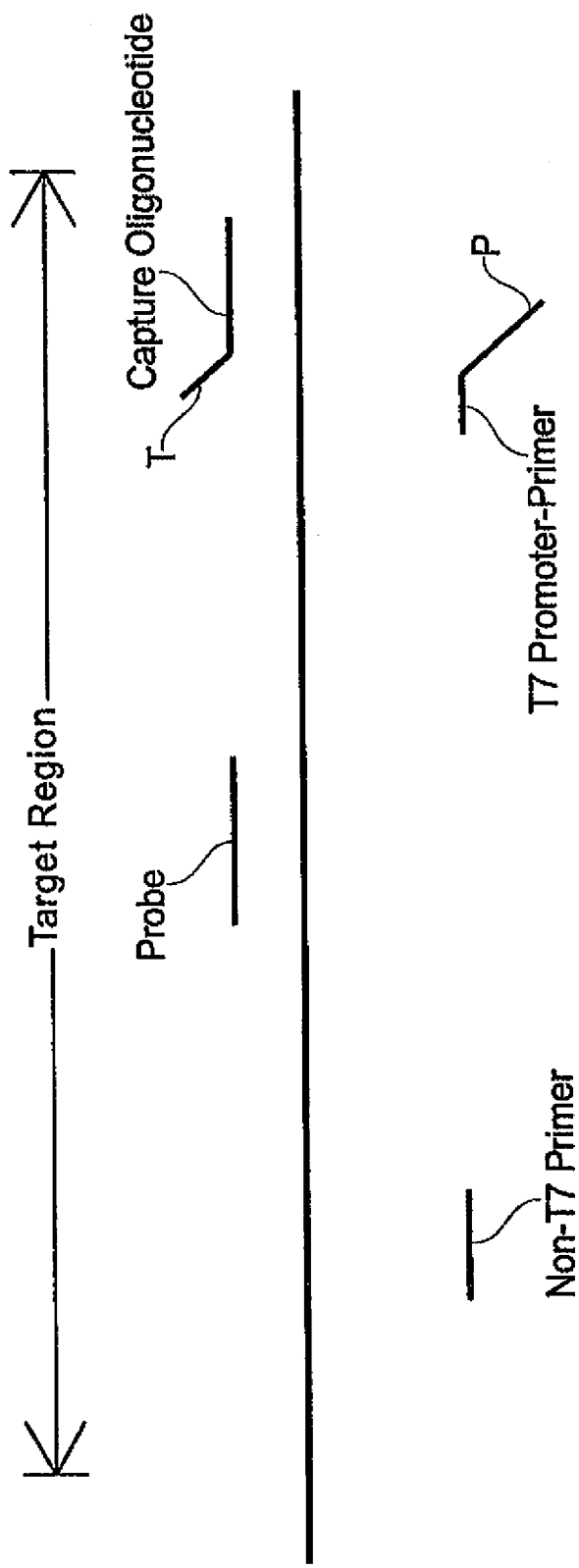
FIG. 1 is a schematic diagram illustrating the various polynucleotides that can be used for detecting a target region within the HBV nucleic acid (represented by a thick horizontal line). Positions of the following nucleic acids are shown relative to the target region: "Capture Oligonucleotide" refers to the nucleic acid used to hybridize to and capture the target nucleic acid prior to amplification, where "T" refers to a tail sequence used to hybridize an immobilized oligonucleotide having a complementary sequence (not shown); "Non-T7 Primer" and "T7 Promoter-Primer" represent two amplification primers used for conducting TMA, where "P" indicates the promoter sequence of the T7 promoter-primer; and "Probe" refers to the probe used for detecting amplified nucleic acid.

The present invention relates to compositions, methods and kits for selectively detecting the nucleic acids of hepatitis B virus (HBV) and/or human immunodeficiency virus-1 (HIV-1) and/or hepatitis C virus (HCV). The compositions disclosed herein are useful for amplifying and detecting these nucleic acids in biological samples such as human blood, serum, plasma or other body fluid or tissue to be tested for the presence of viral nucleic acids. Many of the amplification primers disclosed herein advantageously can be used as components of multiplex amplification reactions, wherein several amplicon species can be produced from a complex assortment of primers and accessory polynucleotides. For example, the most highly preferred HBV-specific primers disclosed herein can be used in multiplex amplification reactions that are capable of amplifying polynucleotides of the unrelated viruses without substantially compromising the sensitivities of those assays.

The probes, primers and methods disclosed herein can be used either in diagnostic applications or for screening donated blood and blood products or other tissues that may contain infectious particles. Additionally, there is disclosed a quantitative assay that employs nucleic acid amplification techniques to measure the number of copies of HBV nucleic acid in a biological sample. This quantitative assay represents an important tool for monitoring viral load in patients undergoing antiviral therapy.

Introduction and Overview

The present invention includes compositions (nucleic acid capture oligonucleotides, amplification oligonucleotides and probes), methods and kits for detecting HBV nucleic acids in a biological sample. To design oligonucleotide sequences appropriate for such uses, known HBV DNA sequences, including subtypes, were first aligned by matching regions having similar sequences and then comparing the sequences to identify candidate regions of the viral genome that could serve as reagents in a diagnostic assay. Based on these comparisons, the "S gene/pol gene" region of the HBV genome was selected for detection using the capture oligonucleotides, primers and probes shown schematically in FIG. 1. Portions of sequences containing relatively few variants between the compared sequences were chosen as starting points for designing synthetic oligonucleotides suitable for use in capture, amplification and detection of amplified sequences. Other considerations in designing oligonucleotides included the relative GC content of the sequence (ranging from about 30% to about 55%), and the relative absence of predicted secondary structure (e.g., hairpin turns forming intramolecular hybrids) within a sequence.

Based on these analyses, the capture oligonucleotide, amplification primer and probe sequences presented below were designed. Those having an ordinary level of skill in the art will appreciate that primer sequences specific for HBV, with or without a T7 promoter sequence, may be used as primers in the various primer-based in vitro amplification methods described below. Additionally, it is also contemplated that the hybridization probes disclosed herein could be used as amplification primers, and that the amplification primers disclosed herein could be used as hybridization probes. Still further, it is contemplated that the hybridization probes disclosed herein could be used as capture oligonucleotides, and that the capture oligonucleotides disclosed herein could be used as hybridization probes. Even still further, it is contemplated that the amplification primers disclosed herein could be used as capture oligonucleotides, and that the capture oligonucleotides disclosed herein could be used as amplification primers.

Useful Amplification Methods

Amplification methods useful in connection with the present invention include: Transcription Mediated Amplification (TMA), Nucleic Acid Sequence-Based Amplification (NASBA), the Polymerase Chain Reaction (PCR), Strand Displacement Amplification (SDA), and amplification methods using self-replicating polynucleotide molecules and replication enzymes such as MDV-1 RNA and Q-beta enzyme. Methods for carrying out these various amplification techniques respectively can be found in U.S. Pat. No. 5,399,491, published European patent application EP 0 525 882, U.S. Pat. No. 4,965,188, U.S. Pat. No. 5,455,166, U.S. Pat. No. 5,472,840 and Lizardi et al., *BioTechnology* 6:1197 (1988). The disclosures of these documents which describe how to perform nucleic acid amplification reactions are hereby incorporated by reference.

In a highly preferred embodiment of the invention, HBV nucleic acid sequences are amplified using a TMA protocol. According to this protocol, the reverse transcriptase which provides the DNA polymerase activity also possesses an endogenous RNase H activity. One of the primers used in this procedure contains a promoter sequence positioned upstream of a sequence that is complementary to one strand of a target nucleic acid that is to be amplified. In the first step of the amplification, a promoter-primer hybridizes to the HBV target DNA at a defined site. Reverse transcriptase creates a complementary DNA copy of the target DNA by extension from the 3' end of the promoter-primer. Following interaction of an opposite strand primer with the newly synthesized DNA strand, a second strand of DNA is synthesized from the end of the primer by reverse transcriptase, thereby creating a double-stranded DNA molecule. RNA polymerase recognizes the promoter sequence in this double-stranded DNA template and initiates transcription. Each of the newly synthesized RNA amplicons re-enters the TMA process and serves as a template for a new round of replication, thereby leading to an exponential expansion of the RNA amplicon. Since each of the DNA templates can make 100-1000 copies of RNA amplicon, this expansion can result in the production of 10 billion amplicons in less than one hour. The entire process is autocatalytic and is performed at a constant temperature.

Structural Features of Primers

As indicated above, a "primer" refers to an optionally modified oligonucleotide which is capable of hybridizing to a template nucleic acid and which has a 3' end that can be extended by a DNA polymerase activity. The 5' region of the primer may be non-complementary to the target nucleic acid. If the 5' non-complementary region includes a promoter sequence, it is referred to as a "promoter-primer." Those skilled in the art will appreciate that any oligonucleotide that can function as a primer (i.e., an oligonucleotide that hybridizes specifically to a target sequence and has a 3' end capable of extension by a DNA polymerase activity) can be modified to include a 5' promoter sequence, and thus could function as a promoter-primer. Similarly, any promoter-primer can be modified by removal of, or synthesis without, a promoter sequence and still function as a primer.

Nucleotide base moieties of primers may be modified (e.g., by the addition of propyne groups), as long as the modified base moiety retains the ability to form a non-covalent association with G, A, C, T or U, and as long as an oligonucleotide comprising at least one modified nucleotide base moiety is not sterically prevented from hybridizing with a single-stranded nucleic acid. As indicated below in connection with the chemical composition of useful probes, the nitrogenous bases of primers in accordance with the invention may be conventional bases (A, G, C, T, U), known analogs thereof (e.g., inosine or "I"; see *The Biochemistry of the Nucleic Acids* 5-36, Adams et al., ed., 11$^{th}$ ed., 1992), known derivatives of purine or pyrimidine bases (e.g., N$^4$-methyl deoxyguanosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines (see, Cook, PCT Int'l Pub. No. WO 93/13121) and "abasic" residues where the backbone includes no nitrogenous base for one or more residues of the polymer (see Arnold et al., U.S. Pat. No. 5,585,481). Common sugar moieties that comprise the primer backbone include ribose and deoxyribose, although 2'-O-methyl ribose (OMe), halogenated sugars, and other modified sugar moieties may also be used. Usually, the linking group of the primer backbone is a phosphorus-containing moiety, most commonly a phosphodiester linkage, although other linkages, such as, for example, phosphorothioates, methylphosphonates, and non-phosphorus-containing linkages such as peptide-like linkages found in "peptide nucleic acids" (PNA) also are intended for use in the assay disclosed herein.

Useful Probe Labeling Systems and Detectable Moieties

Essentially any labeling and detection system that can be used for monitoring specific nucleic acid hybridization can be used in conjunction with the present invention. Included among the collection of useful labels are radiolabels, enzymes, haptens, linked oligonucleotides, chemiluminescent molecules and redox-active moieties that are amenable to electronic detection methods. Preferred chemiluminescent molecules include acridinium esters of the type disclosed by Arnold et al., in U.S. Pat. No. 5,283,174 for use in connection with homogenous protection assays, and of the type disclosed by Woodhead et al., in U.S. Pat. No. 5,656,207 for use in connection with assays that quantify multiple targets in a single reaction. The disclosures contained in these patent documents are hereby incorporated by reference. Preferred electronic labeling and detection approaches are disclosed in U.S. Pat. Nos. 5,591,578 and 5,770,369, and the published international patent application WO 98/57158, the disclosures of which are hereby incorporated by reference. Redox active moieties useful as labels in the present invention include transition metals such as Cd, Mg, Cu, Co, Pd, Zn; Fe and Ru.

Particularly preferred detectable labels for probes in accordance with the present invention are detectable in homogeneous assay systems (i.e., where, in a mixture, bound labeled probe exhibits a detectable change, such as stability or differential degradation, compared to unbound labeled probe). A preferred label for use in homogenous assays is a chemiluminescent compound (e.g., as described by Woodhead et al., in U.S. Pat. No. 5,656,207; by Nelson et al., in U.S. Pat. No. 5,658,737; or by Arnold et al., in U.S. Pat. No. 5,639,604). Particularly preferred chemiluminescent labels include acridinium ester ("AE") compounds, such as standard AE or derivatives thereof, such as naphthyl-AE, ortho-AE, 1- or 3-methyl-AE, 2,7-dimethyl-AE, 4,5-dimethyl-AE, ortho-dibromo-AE, ortho-dimethyl-AE, meta-dimethyl-AE, ortho-methoxy-AE, ortho-methoxy(cinnamyl)-AE, ortho-methyl-AE, ortho-fluoro-AE, 1- or 3-methyl-ortho-fluoro-AE, 1- or 3-methyl-meta-difluoro-AE, and 2-methyl-AE.

In some applications, probes exhibiting at least some degree of self-complementarity are desirable to facilitate detection of probe:target duplexes in a test sample without first requiring the removal of unhybridized probe prior to detection. By way of example, structures referred to as "Molecular Torches" are designed to include distinct regions of self-complementarity (coined "the target binding domain" and "the target closing domain") which are connected by a joining region and which hybridize to one another under predetermined hybridization assay conditions. When exposed to denaturing conditions, the two complementary regions (which may be fully or partially complementary) of the Molecular Torch melt, leaving the target binding domain available for hybridization to a target sequence when the predetermined hybridization assay conditions are restored. Molecular Torches are designed so that the target binding domain favors hybridization to the target sequence over the target closing domain. The target binding domain and the target closing domain of a Molecular Torch include interacting labels (e.g., luminescent/quencher) positioned so that a different signal is produced when the Molecular Torch is self-hybridized as opposed to when the Molecular Torch is hybridized to a target nucleic acid, thereby permitting detection of probe:target duplexes in a test sample in the presence of unhybridized probe having a viable label associated therewith. Molecular Torches are fully described in International Publication No. WO 00/01850, the disclosure of which is hereby incorporated by reference.

Another example of a self-complementary hybridization assay probe that may be used in conjunction with the invention is a structure commonly referred to as a "Molecular Beacon." Molecular Beacons comprise nucleic acid molecules having a target complement sequence, an affinity pair (or nucleic acid arms) holding the probe in a closed conformation in the absence of a target nucleic acid sequence, and a label pair that interacts when the probe is in a closed conformation. Hybridization of the target nucleic acid and the target complement sequence separates the members of the affinity pair, thereby shifting the probe to an open confirmation. The shift to the open confirmation is detectable due to reduced interaction of the label pair, which may be, for example, a fluorophore and a quencher. Molecular Beacons are described in U.S. Pat. No. 5,925,517, the disclosure of which is hereby incorporated by reference. Molecular beacons useful for detecting HBV-specific nucleic acid sequences may be created by appending to either end of one of the probe sequences disclosed herein, a first nucleic acid arm comprising a fluorophore and a second nucleic acid arm comprising a quencher moiety. In this configuration, the HBV-specific probe sequence disclosed herein serves as the target-complementary "loop" portion of the resulting molecular beacon.

Molecular beacons preferably are labeled with an interactive pair of detectable labels. Examples of detectable labels that are preferred as members of an interactive pair of labels interact with each other by FRET or non-FRET energy transfer mechanisms. Fluorescence resonance energy transfer (FRET) involves the radiationless transmission of energy quanta from the site of absorption to the site of its utilization in the molecule, or system of molecules, by resonance interaction between chromophores, over distances considerably greater than interatomic distances, without conversion to thermal energy, and without the donor and acceptor coming into kinetic collision. The "donor" is the moiety that initially absorbs the energy, and the "acceptor" is the moiety to which the energy is subsequently transferred. In addition to FRET, there are at least three other "non-FRET" energy transfer processes by which excitation energy can be transferred from a donor to an acceptor molecule.

When two labels are held sufficiently close that energy emitted by one label can be received or absorbed by the second label, whether by a FRET or non-FRET mechanism, the two labels are said to be in "energy transfer relationship" with each other. This is the case, for example, when a molecular beacon is maintained in the closed state by formation of a stem duplex, and fluorescent emission from a fluorophore attached to one arm of the probe is quenched by a quencher moiety on the opposite arm.

Highly preferred label moieties for the invented molecular beacons include a fluorophore and a second moiety having fluorescence quenching properties (i.e., a "quencher"). In this embodiment, the characteristic signal is likely fluorescence of a particular wavelength, but alternatively could be a visible light signal. When fluorescence is involved, changes in emission are preferably due to FRET, or to radiative energy transfer or non-FRET modes. When a molecular beacon having a pair of interactive labels in the closed state is stimulated by an appropriate frequency of light, a fluorescent signal is generated at a first level, which may be very low. When this same probe is in the open state and is stimulated by an appropriate frequency of light, the fluorophore and the quencher moieties are sufficiently separated from each other that energy transfer between them is substantially precluded. Under that condition, the quencher moiety is unable to quench the fluorescence from the fluorophore moiety. If the fluorophore is stimulated by light energy of an appropriate wavelength, a fluorescent signal of a second level, higher than the first level, will be generated. The difference between the two levels of fluorescence is detectable and measurable. Using fluorophore and quencher moieties in this manner, the molecular beacon is only "on" in the "open" conformation and indicates that the probe is bound to the target by emanating an easily detectable signal. The conformational state of the probe alters the signal generated from the probe by regulating the interaction between the label moieties.

Examples of donor/acceptor label pairs that may be used in connection with the invention, making no attempt to distinguish FRET from non-FRET pairs, include fluorescein/tetramethylrhodamine, IAEDANS/fluororescein, EDANS/DABCYL, coumarin/DABCYL, fluorescein/fluorescein, BODIPY FL/BODIPY FL, fluorescein/DABCYL, lucifer yellow/DABCYL, BODIPY/DABCYL, eosine/DABCYL, erythrosine/DABCYL, tetramethylrhodamine/DABCYL, Texas Red/DABCYL, CY5/BH1, CY5/BH2, CY3/BH1, CY3/BH2 and fluorescein/QSY7 dye. Those having an ordinary level of skill in the art will understand that when donor and acceptor dyes are different, energy transfer can be detected by the appearance of sensitized fluorescence of the acceptor or by quenching of donor fluorescence. When the donor and acceptor species are the same, energy can be detected by the resulting fluorescence depolarization. Non-fluorescent acceptors such as DABCYL and the QSY 7 dyes advantageously eliminate the potential problem of background fluorescence resulting from direct (i.e., non-sensitized) acceptor excitation. Preferred fluorophore moieties that can be used as one member of a donor-acceptor pair include fluorescein, ROX, and the CY dyes (such as CY5). Highly preferred quencher moieties that can be used as another member of a donor-acceptor pair include DABCYL and the BLACK HOLE QUENCHER moieties which are available from Biosearch Technologies, Inc., (Novato, Calif.).

Synthetic techniques and methods of bonding labels to nucleic acids and detecting labels are well known in the art (e.g., see Sambrook et al., *Molecular Cloning, A Laboratory Manual*, 2nd ed. (Cold Spring Harbor Laboratory Press, Cold Spring Harbor, N.Y., 1989), Chapter 10; Nelson et al., U.S. Pat. No. 5,658,737; Woodhead et al., U.S. Pat. No. 5,656,207; Hogan et al., U.S. Pat. No. 5,547,842; Arnold et al., U.S. Pat. No. 5,283,174; Kourilsky et al., U.S. Pat. No. 4,581,333), and Becker et al., European Patent App. No. 0 747 706.

Chemical Composition of Probes

Probes in accordance with the invention comprise polynucleotides or polynucleotide analogs and may carry a detectable label covalently bonded thereto. Nucleosides or nucleoside analogs of the probe comprise nitrogenous heterocyclic bases, or base analogs, where the nucleosides are linked together, for example by phosphohdiester bonds to form a polynucleotide. Accordingly, a probe may comprise conventional ribonucleic acid (RNA) and/or deoxyribonucleic acid (DNA), but also may comprise chemical analogs of these molecules. The "backbone" of a probe may be made up of a variety of linkages known in the art, including one or more sugar-phosphodiester linkages, peptide-nucleic acid bonds (sometimes referred to as "peptide nucleic acids" as described by Hyldig-Nielsen et al., PCT Intl Pub. No. WO 95/32305), phosphorothioate linkages, methylphosphonate linkages or combinations thereof. Sugar moieties of the probe may be either ribose or deoxyribose, or similar compounds having known substitutions, such as, for example, 2'-O-methyl ribose and 2' halide substitutions (e.g., 2'-F). The nitrogenous bases may be conventional bases (A, G, C, T, U), known analogs thereof (e.g., inosine or "I"; see *The Biochemistry of the Nucleic Acids* 5-36, Adams et al., ed., 11$^{th}$ ed., 1992), known derivatives of purine or pyrimidine bases (e.g., N$^4$-methyl deoxygaunosine, deaza- or aza-purines and deaza- or aza-pyrimidines, pyrimidine bases having substituent groups at the 5 or 6 position, purine bases having an altered or a replacement substituent at the 2, 6 or 8 positions, 2-amino-6-methylaminopurine, O$^6$-methylguanine, 4-thio-pyrimidines, 4-amino-pyrimidines, 4-dimethylhydrazine-pyrimidines, and O$^4$-alkyl-pyrimidines (see, Cook, PCT Intl Pub. No. WO 93/13121) and "abasic" residues where the backbone includes no nitrogenous base for one or more residues of the polymer (see Arnold et al., U.S. Pat. No. 5,585,481). A nucleic acid may comprise only conventional sugars, bases and linkages found in RNA and DNA, or may include both conventional components and substitutions (e.g., conventional bases linked via a methoxy backbone, or a nucleic acid including conventional bases and one or more base analogs).

Selection of Amplification Primers and Detection Probes Specific for HBV

Useful guidelines for designing amplification primers and probes with desired characteristics are described herein. The optimal sites for amplifying and probing HBV nucleic acids contain two, and preferably three, conserved regions greater than about 15 bases in length, within about 200 bases, and preferably within 110 bases, of contiguous sequence. The degree of amplification observed with a set of primers or promoter-primers depends on several factors, including the ability of the oligonucleotides to hybridize to their complementary sequences and their ability to be extended enzymatically. Because the extent and specificity of hybridization reactions are affected by a number of factors, manipulation of those factors will determine the exact sensitivity and specificity of a particular oligonucleotide, whether perfectly complementary to its target or not. The effects of varying assay conditions are known to those skilled in the art, and are described by Hogan et al., in U.S. Pat. No. 5,840,488, the disclosure of which is hereby incorporated by reference.

The length of the target nucleic acid sequence and, accordingly, the length of the primer sequence or probe sequence can be important. In some cases, there may be several sequences from a particular target region, varying in location and length, which will yield primers or probes having the desired hybridization characteristics. While it is possible for nucleic acids that are not perfectly complementary to hybridize, the longest stretch of perfectly homologous base sequence will normally primarily determine hybrid stability.

Amplification primers and probes should be positioned to minimize the stability of the oligonucleotide:nontarget (i.e., nucleic acid with similar sequence to target nucleic acid) nucleic acid hybrid. It is preferred that the amplification primers and detection probes are able to distinguish between target and non-target sequences. In designing primers and probes, the differences in these Tm values should be as large as possible (e.g., at least 2° C. and preferably 5° C.).

Regions of the nucleic acid which are known to form strong internal structures inhibitory to hybridization are less preferred as primers or probes. Examples of such structures include hairpin loops. Likewise, oligonucleotides with extensive self-complementarity should be avoided.

The degree of non-specific extension (primer-dimer or non-target copying) can also affect amplification efficiency. For this reason, primers are selected to have low self- or cross-complementarity, particularly at the 3' ends of the sequence. Long homopolymer tracts and high GC content are avoided to reduce spurious primer extension. Commercially available computer software can aid in this aspect of the design. Available computer programs include MacDNA-SIS™ 2.0 (Hitachi Software Engineering American Ltd.) and OLIGO ver. 4.1 (National Bioscience).

Those having an ordinary level of skill in the art will appreciate that hybridization involves the association of two single strands of complementary nucleic acid to form a hydrogen bonded double strand. It is implicit that if one of the two strands is wholly or partially involved in a hybrid, then that strand will be less able to participate in formation of a new hybrid. By designing primers and probes so that substantial portions of the sequences of interest are single stranded, the rate and extent of hybridization may be greatly increased. If the target is an integrated genomic sequence, then it will naturally occur in a double stranded form (as is the case with the product of the polymerase chain reaction). These double-stranded targets are naturally inhibitory to hybridization with a probe and require denaturation prior to the hybridization step.

The rate at which a polynucleotide hybridizes to its target is a measure of the thermal stability of the target secondary structure in the target binding region. The standard measurement of hybridization rate is the $C_0t_{1/2}$ which is measured as moles of nucleotide per liter multiplied by seconds. Thus, it is the concentration of probe multiplied by the time at which 50% of maximal hybridization occurs at that concentration. This value is determined by hybridizing various amounts of polynucleotide to a constant amount of target for a fixed time. The $C_0t_{1/2}$ is found graphically by standard procedures familiar to those having an ordinary level of skill in the art.

Preferred Amplification Primers

Many of the oligonucleotides, including primers and probes, disclosed herein were derived from the sequence of the HBV, subtype ADW. The entire nucleotide sequence of the cloned hepatitis B virus DNA, subtype ADW can be accessed through GENBANK Accession No. V00866.

Generally speaking, primers useful for conducting amplification reactions in accordance with the invention have a downstream HBV-complementary sequence, and optionally an upstream sequence that is not complementary to the HBV target. The HBV-complementary sequences of certain primers which are complementary to one strand of the HBV target nucleic acid (i.e., "first strand" primers) preferably are 20-50 bases in length and have 20-50 contiguous bases of SEQ ID NO:2, allowing for RNA and DNA equivalents and for substitution of nucleotide analogs. The HBV-complementary sequences of certain primers which are complementary to the second, or opposite strand of the HBV target nucleic acid (i.e., "second strand" primers) preferably are 20-54 bases in length and have 20-54 contiguous bases of SEQ ID NO:4, allowing for RNA and DNA equivalents and for substitution of nucleotide analogs. Of course, the optional upstream sequences which are not complementary to the HBV target will add to the overall lengths of the primers. An example of an optional upstream sequence would be a promoter for an RNA polymerase.

Primers useful for conducting amplification reactions can have different lengths. For example, amplification oligonucleotides complementary to one strand of the HBV target nucleic acid sequence (i.e., first strand primers) preferably have lengths of up to 100 bases, more preferably from 18-60 bases, and have HBV-complementary sequences ranging in length from 18-27 bases, or more preferably from 20-23 bases and include at least 18 contiguous bases, allowing for substitution of one or more nitrogenous base analogs, substantially corresponding to the sequence given by GTGTCTTGGC-CAAAATTCGCAGTCCCCAACCTCCAATCACTCACC-AACCTCCTGTCCTCCAATTTGTCCTGGTTATCGCTG-GATGTGTCTGCGGCGTTTTATCATATTCCTCTTCAT-CCTGCTGCTAT (SEQ ID NO:1). Examples of primers, including promoter-primers, falling within this group include SEQ ID NOs:16-49. Even more highly preferred primers for amplifying HBV nucleic acids have lengths of up to 100 bases, more preferably from 20-60 bases, and have HBV-complementary sequences that include at least 20 contiguous bases, more preferably 20-24 contiguous bases, allowing for substitution of one or more nitrogenous base analogs, contained within a sequence substantially corresponding to CTGGATGTGTCTGCGGCGTTTTATCATTCCTCTTCA-TCCTGCTGCTAT (SEQ ID NO:2). Examples of primers falling within this group include SEQ ID NOs:22-28, and the respective T7 promoter-primers of SEQ ID NOs:39-45. Another highly preferred collection of primers for amplifying HBV nucleic acids have lengths of up to 100 bases, more preferably from 20-60 bases, and have HEV-complementary sequences that include at least 23 contiguous bases, more preferably 23-24 contiguous bases, allowing for substitution of one or more nitrogenous base analogs, contained within a sequence substantially corresponding to ATCATATTC-CTCTTCATCCTGCTGCTAT (SEQ ID NO:3). Examples of primers falling within this group include SEQ ID NOs:24-28, and the respective T7 promoter-primers of SEQ ID NOs:41-45. When using a TMA reaction to amplify HBV sequences, primers having these characteristics are highly preferred for use as promoter-primers, such as T7 promoter-primers. Of course, if the primer is a T7 promoter-primer there will be included at the 5' end a T7 promoter sequence which typically adds about 27-33 bases to the length of the primer. Examples of promoter-primers include oligonucleotides having the sequences given by SEQ ID NOs:33-49. The promoter-primers disclosed herein are particularly desirable for performing nucleic acid amplification reactions using the above-referenced TMA procedure.

Other primers (i.e., second strand primers) that can be used with the above-described primers in any combination for carrying out amplification reactions are complementary to the opposite strand of the HBV target nucleic acid sequence. Amplification primers complementary to this opposite strand of the HBV target nucleic acid sequence preferably have lengths of up to 100 bases, or more preferably 20-31 bases, or still more preferably 20-21 bases. These primers are particularly preferred for use as non-promoter primers (i.e., primers that are complementary to the opposite strand of the HBV template when compared with the promoter-primers). As disclosed herein, these primers have at least 20 contiguous bases, allowing for substitution of nitrogenous base analogs, from a sequence substantially corresponding to GGAATTAGAG-GACAAACGGGCAACATACCTTGATAATCCAGAAGA-ACCAATAAG (SEQ ID NO:4). Examples of particular amplification primers fulfilling these criteria include oligonucleotides having the sequences given by SEQ ID NOs:5-15. Even more preferred are primers having at least 20 contiguous bases, allowing for substitution of nitrogenous base analogs, from a sequence substantially corresponding to AGGACAAACGGGCAACATACCTTGATAATCCAGAA-GAACCAATAAG (SEQ ID NO:142). Examples of particular amplification primers fulfilling these criteria include oligonucleotides having the sequences given by SEQ ID NOs: 5-9, 11 and 15.

It should be understood that the above-specified variable lengths of the amplification primers accommodate the presence of extraneous sequences that do not participate in target binding, and that may not substantially affect amplification or detection procedures. For example, promoter-primers useful for performing amplification reactions in accordance with the invention have at least a minimal sequence that hybridizes to the HBV target nucleic acid, and a promoter sequence positioned upstream of that minimal sequence. However, insertion of sequences between the target binding sequence and the promoter sequence could change the length of the primer without compromising its utility in the amplification reaction. Additionally, the lengths of the amplification primers and detection probes are matters of choice as long as the sequences of these oligonucleotides conform to the minimal essential requirements for hybridizing the desired complementary sequence.

Tables 1 and 2 present specific examples of oligonucleotide sequences that were used as primers for amplifying HBV nucleic acids. Table 1 presents the sequences of primers that were complementary to HBV sequences on one strand of nucleic acid. Table 2 presents the sequences of both the HBV target-complementary sequences and the full sequences for promoter-primers that were used during development of the invention. Compared with the oligonucleotide sequences in Table 1, the oligonucleotide sequences in Table 2 are complementary to the opposite nucleic acid strand of the HBV genome.

TABLE 1

| Polynucleotide Sequences of Amplification Primers | |
|---|---|
| Sequence (5' to 3') | Identifier |
| TTGATAATCCAGAAGAACCAA | SEQ ID NO: 5 |
| CTTGATAATCCAGAAGAACCA | SEQ ID NO: 6 |
| TACCTTGATAATCCAGAAGAACCA | SEQ ID NO: 7 |
| GATAATCCAGAAGAACCAATAA | SEQ ID NO: 8 |
| ATAATCCAGAAGAACCAATAAG | SEQ ID NO: 9 |
| AGAGGACAAACGGGCAACAT | SEQ ID NO: 10 |
| AGGACAAACGGGCAACATAC | SEQ ID NO: 11 |
| GGAATTAGAGGACAAACGGGCAACATACCTT | SEQ ID NO: 12 |
| TTAGAGGACAAACGGGCAACATACCTT | SEQ ID NO: 13 |
| GAGGACAAACGGGCAACATACCTT | SEQ ID NO: 14 |
| GACAAACGGGCAACATACCTT | SEQ ID NO: 15 |

Table 2 presents HBV target-complementary oligonucleotide sequences (SEQ ID NOs:16-32) and the corresponding promoter-primer sequences (SEQ ID NOs:33-49). As indicated above, all promoter-primers included sequences complementary to an HBV target sequence at their 3' ends, and a T7 promoter sequence at their 5' ends.

TABLE 2

| Polynucleotide Sequences of Amplification Primers | |
|---|---|
| Sequence (5' to 3') | Identifier |
| GTGTCTTGGCCAAAATTCGCAGTC | SEQ ID NO: 16 (HBV complementary primer) |
| GTCCCCAACCTCCAATCACTCACCAA | SEQ ID NO: 17 (HBV complementary primer) |
| CCCAACCTCCAATCACTCACCAAC | SEQ ID NO: 18 (HBV complementary primer) |

TABLE 2-continued

Polynucleotide Sequences of Amplification Primers

| Sequence (5' to 3') | Identifier |
| --- | --- |
| CTGTCCTCCAATTTGTCCTGGTTATC | SEQ ID NO: 19 (HBV complementary primer) |
| CCAACCTCCTGTCCTCCAATTTGTCCT | SEQ ID NO: 20 (HBV complementary primer) |
| CAACCTCCTGTCCTCCAATTTGTCCTG | SEQ ID NO: 21 (HBV complementary primer) |
| CTGGATGTGTCTGCGGCGTT | SEQ ID NO: 22 (HBV complementary primer) |
| GATGTGTCTGCGGCGTTTTATC | SEQ ID NO: 23 (HBV complementary primer) |
| ATCATATTCCTCTTCATCCTGCT | SEQ ID NO: 24 (HBV complementary primer) |
| ATATTCCTCTTCATCCTGCTGCT | SEQ ID NO: 25 (HBV complementary primer) |
| ATATTCCTCTICATCCTGCTGCT | SEQ ID NO: 26 (HBV complementary primer) |
| ATATTCCTCTTCATCCTGCTGCTA | SEQ ID NO: 27 (HBV complementary primer) |
| ATTCCTCTTCATCCTGCTGCTAT | SEQ ID NO: 28 (HBV complementary primer) |
| AATTTGTCCTGGTTATCGCTG | SEQ ID NO: 29 (HBV complementary primer) |
| CCTGGTTATCGCTGGATG | SEQ ID NO: 30 (HBV complementary primer) |
| CTGGTTATCGCTGGATGT | SEQ ID NO: 31 (HBV complementary primer) |
| TGGTTATCGCTGGATGTG | SEQ ID NO: 32 (HBV complementary primer) |
| AATTTAATACGACTCACTATAGGGAGAGTGTCTTGGCCAAAATTCGCAGTC | SEQ ID NO: 33 (T7 promoter-primer) |
| AATTTAATACGACTCACTATAGGGAGAGTCCCCAACCTCCAATCACTCACCAA | SEQ ID NO: 34 (T7 promoter-primer) |
| AATTTAATACGACTCACTATAGGGAGACCCAACCTCCAATCACTCACCAAC | SEQ ID NO: 35 (T7 promoter-primer) |
| AATTTAATACGACTCACTATAGGGAGACTGTCCTCCAATTTGTCCTGGTTATC | SEQ ID NO: 36 (T7 promoter-primer) |
| AATTTAATACGACTCACTATAGGGAGACCAACCTCCTGTCCTCCAATTTGTCCT | SEQ ID NO: 37 (T7 promoter-primer) |
| AATTTAATACGACTCACTATAGGGAGACAACCTCCTGTCCTCCAATTTGTCCTG | SEQ ID NO: 38 (T7 promoter-primer) |
| AATTTAATACGACTCACTATAGGGAGACTGGATGTGTCTGCGGCGTT | SEQ ID NO: 39 (T7 promoter-primer) |
| AATTTAATACGACTCACTATAGGGAGAGATGTGTCTGCGGCGTTTTATC | SEQ ID NO: 40 (T7 promoter-primer) |
| AATTTAATACGACTCACTATAGGGAGAATCATATTCCTCTTCATCCTGCT | SEQ ID NO: 41 (T7 promoter-primer) |
| AATTTAATACGACTCACTATAGGGAGAATATTCCTCTTCATCCTGCTGCT | SEQ ID NO: 42 (T7 promoter-primer) |
| AATTTAATACGACTCACTATAGGGAGAATATTCCTCTICATCCTGCTGCT | SEQ ID NO: 43 (T7 promoter-primer) |

TABLE 2-continued

Polynucleotide Sequences of Amplification Primers

| Sequence (5' to 3') | Identifier |
| --- | --- |
| AATTTAATACGACTCACTATAGGGAGA ATATTCCTCTTCATCCTGCTGCTA | SEQ ID NO: 44 (T7 promoter-primer) |
| AATTTAATACGACTCACTATAGGGAGA ATTCCTCTTCATCCTGCTGCTAT | SEQ ID NO: 45 (T7 promoter-primer) |
| AATTTAATACGACTCACTATAGGGAGA AATTTGTCCTGGTTATCGCTG | SEQ ID NO: 46 (T7 promoter-primer) |
| AATTTAATACGACTCACTATAGGGAGA CCTGGTTATCGCTGGATG | SEQ ID NO: 47 (T7 promoter-primer) |
| AATTTAATACGACTCACTATAGGGAGA CTGGTTATCGCTGGATGT | SEQ ID NO: 48 (T7 promoter-primer) |
| AATTTAATACGACTCACTATAGGGAGA TGGTTATCGCTGGATGTG | SEQ ID NO: 49 (T7 promoter-primer) |

Preferred sets of primers for amplifying HBV sequences in a TMA reaction include a first primer that hybridizes an HBV target sequence (such as one of the primers listed in Table 2) and a second primer that is complementary to the sequence of an extension product of the first primer (such as one of the primer sequences listed in Table 1). In a highly preferred embodiment, the first primer is a promoter-primer that includes a T7 promoter sequence at its 5' end.

Preferred Detection Probes

Another aspect of the invention relates to oligonucleotides that can be used as hybridization probes for detecting HBV nucleic acids. Methods for amplifying a target nucleic acid sequence present in the nucleic acid of HBV can include an optional further step for detecting amplicons. This procedure for detecting HBV nucleic acids includes a step for contacting a test sample with a hybridization assay probe that preferentially hybridizes to the target nucleic acid sequence, or the complement thereof, under stringent hybridization conditions, thereby forming a probe:target duplex that is stable for detection. Next there is a step for determining whether the hybrid is present in the test sample as an indication of the presence or absence of HBV nucleic acids in the test sample. This may involve detecting the probe:target duplex.

Hybridization assay probes useful for detecting HEY nucleic acid sequences include a sequence of bases substantially complementary to an HBV target nucleic acid sequence. Thus, probes of the invention hybridize one strand of an HBV target nucleic acid sequence, or the complement thereof. These probes may optionally have additional bases outside of the targeted nucleic acid region which may or may not be complementary to HBV nucleic acid.

Preferred probes are sufficiently homologous to the target nucleic acid to hybridize under stringent hybridization conditions corresponding to about 60° C. when the salt concentration is in the range of 0.6-0.9 M. Preferred salts include lithium chloride, but other salts such as sodium chloride and sodium citrate also can be used in the hybridization solution. Example high stringency hybridization conditions are alternatively provided by 0.48 M sodium phosphate buffer, 0.1% sodium dodecyl sulfate, and 1 mM each of EDTA and EGTA, or by 0.6 M LiCl, 1% lithium lauryl sulfate, 60 mM lithium succinate and 10 mM each of EDTA and EGTA.

Certain probes that are preferred for detecting HBV nucleic acid sequences have target-complementary sequences in the length range of from 17-23 nucleotides.

Highly preferred probes that may be used for detecting HBV nucleic acids have target-complementary sequences 23 nucleotides, more preferably 22, more preferably 20, more preferably 19, more preferably 18, or more preferably 17 nucleotides in length. Of course, these target-complementary sequences may be linear sequences, or may be contained in the structure of a molecular beacon or other construct having one or more optional nucleic acid sequences that are non-complementary to the HBV target sequence that is to be detected. As indicated above, probes may be made of DNA, RNA, a combination DNA and RNA, a nucleic acid analog, or contain one or more modified nucleosides (e.g., a ribonucleoside having a 2'-O-methyl substitution to the ribofuranosyl moiety).

Examples of probes that can be used to carry out the assay disclosed herein include at least 17, more preferably 17-23 or still more preferably 17-19 contiguous nucleotides contained within the sequence given by ACGGGCAACATACCT-TGATAGTCCAGAAGAACCAACAAGAAGATGAGGC-ATAGCAGCAGGATGCAGAGGAA (SEQ ID NO:67), or the complement thereof, allowing for the presence of RNA and DNA equivalents and the substitution of nucleotide analogs. Certain preferred probes in accordance with the present invention include a detectable label. In one embodiment this label is an acridinium ester that is joined to the probe by means of a non-nucleotide linker. For example, detection probes can be labeled with chemiluminescent acridinium ester compounds that are attached via a linker substantially as described in U.S. Pat. No. 5,585,481; and in U.S. Pat. No. 5,639,604, particularly as described at column 10, line 6 to column 11, line 3, and in Example 8. The disclosures contained in these patent documents are hereby incorporated by reference. When the hybridization probe is labeled with an acridinium ester moiety via an internally disposed linker, the probe is preferably stored in the presence of a "protection probe" in accordance with U.S. Pat. No. 6,245,519, the disclosure of which is hereby incorporated by reference. For example, if the probe is 19 bases long and has an acridinium ester joined between positions 6 and 7, the corresponding protection probe can be 16 bases long to provide the necessary differential Tm. In this instance we used a protection probe that had 3 complementary bases on one side, and 13 complementary bases on the other side of an acridinium ester label that was linked to the probe. Of course, other sequence variations may be envisioned.

Table 3 presents the sequences of hybridization probes that were used for detecting HBV amplicons. Since alternative probes for detecting HBV nucleic acid sequences can hybridize to the opposite-sense strand of HBV, the present invention also includes oligonucleotides that are complementary to the sequences presented in the table.

TABLE 3

Polynucleotide Sequences of HBV Detection Probes

| Sequence (5' to 3') | Identifier |
| --- | --- |
| AGCAGGAUGAAGAGGAA | SEQ ID NO: 50 |
| GCAGCAGGAUGAAGAGGA | SEQ ID NO: 51 |
| GCAGCAGGATGAAGAGG | SEQ ID NO: 52 |
| UGAGGCAUAGCAGCAGGA | SEQ ID NO: 53 |
| GAAGATGAGGCATAGCAGC | SEQ ID NO: 54 |
| ACAAGAAGAUGAGGCAUAGCAGC | SEQ ID NO: 55 |
| AGAAGAUGAGGCAUAGCAG | SEQ ID NO: 56 |
| AAGAAGAUGAGGCAUAGC | SEQ ID NO: 57 |
| ACAAGAAGATGAGGCATA | SEQ ID NO: 58 |
| CCAACAAGAAGAUGAGGC | SEQ ID NO: 59 |
| AIUCCAGAAGAACCAACAAGAAG | SEQ ID NO: 60 |
| AIUCCAGAAGAACCAACAAGAAG | SEQ ID NO: 61 |
| CCAGAAGAACCAACAAGAAG | SEQ ID NO: 62 |
| CCUUGAUAGUCCAGAAGAACCA | SEQ ID NO: 63 |
| CCUUGAUAGUCCAGAAGAACCAA | SEQ ID NO: 64 |
| ACGGGCAACAUACCUUG | SEQ ID NO: 65 |
| CGGGCAACAUACCUUG | SEQ ID NO: 66 |

In some embodiments of the invention, the probe sequence used for detecting HBV amplicons includes a methoxy backbone, or at least one methoxy linkage in the nucleic acid backbone.

Selection and Use of Capture Oligonucleotides

Preferred capture oligonucleotides include a first sequence that is complementary to an HBV sequence (i.e., an "HBV target sequence") covalently attached to a second sequence (i.e., a "tail" sequence) that serves as a target for immobilization on a solid support. Any backbone to link the base sequence of a capture oligonucleotide may be used. In certain preferred embodiments the capture oligonucleotide includes at least one methoxy linkage in the backbone. The tail sequence, which is preferably at the 3' end of a capture oligonucleotide, is used to hybridize to a complementary base sequence to provide a means for capturing the hybridized target HBV nucleic acid in preference to other components in the biological sample.

Although any base sequence that hybridizes to a complementary base sequence may be used in the tail sequence, it is preferred that the hybridizing sequence span a length of about 5-50 nucleotide residues. Particularly preferred tail sequences are substantially homopolymeric, containing about 10 to about 40 nucleotide residues, or more preferably about 14 to about 30 residues. A capture oligonucleotide according to the present invention may include a first sequence that specifically binds an HBV target polynucleotide, and a second sequence that specifically binds an oligo(dT) stretch immobilized to a solid support.

Using the components illustrated in FIG. 1, one assay for detecting HBV sequences in a biological sample includes the steps of capturing the target nucleic acid using the capture oligonucleotide, amplifying the captured target region using at least two primers, and detecting the amplified nucleic acid by first hybridizing the labeled probe to a sequence contained in the amplified nucleic acid and then detecting a signal resulting from the bound labeled probe.

The capturing step preferably uses a capture oligonucleotide where, under hybridizing conditions, one portion of the capture oligonucleotide specifically hybridizes to a sequence in the target nucleic acid and a tail portion serves as one component of a binding pair, such as a ligand (e.g., a biotin-avidin binding pair) that allows the target region to be separated from other components of the sample. Preferably, the tail portion of the capture oligonucleotide is a sequence that hybridizes to a complementary sequence immobilized to a solid support particle. Preferably, first, the capture oligonucleotide and the target nucleic acid are in solution to take advantage of solution phase hybridization kinetics. Hybridization produces a capture oligonucleotide:target nucleic acid complex which can bind an immobilized probe through hybridization of the tail portion of the capture oligonucleotide with a complementary immobilized sequence. Thus, a complex comprising a target nucleic acid, capture oligonucleotide and immobilized probe is formed under hybridization conditions. Preferably, the immobilized probe is a repetitious sequence, and more preferably a homopolymeric sequence (e.g., poly-A, poly-T, poly-C or poly-G), which is complementary to the tail sequence and attached to a solid support. For example, if the tail portion of the capture oligonucleotide contains a poly-A sequence, then the immobilized probe would contain a poly-T sequence, although any combination of complementary sequences may be used. The capture oligonucleotide may also contain "spacer" residues, which are one or more bases located between the base sequence that hybridizes to the target and the base sequence of the tail that hybridizes to the immobilized probe. Any solid support may be used for binding the target nucleic acid:capture oligonucleotide complex. Useful supports may be either matrices or particles free in solution (e.g., nitrocellulose, nylon, glass, polyacrylate, mixed polymers, polystyrene, silane polypropylene and, preferably, magnetically attractable particles). Methods of attaching an immobilized probe to the solid support are well known. The support is preferably a particle which can be retrieved from solution using standard methods (e.g., centrifugation, magnetic attraction of magnetic particles, and the like). Preferred supports are paramagnetic monodisperse particles (i.e., uniform in size ±about 5%).

Retrieving the target nucleic acid:capture oligonucleotide:immobilized probe complex effectively concentrates the target nucleic acid (relative to its concentration in the biological sample) and purifies the target nucleic acid from amplification inhibitors which may be present in the biological sample. The captured target nucleic acid may be washed one or more times, further purifying the target, for example, by resuspending the particles with the attached target nucleic acid:capture oligonucleotide:immobilized probe complex in a washing solution and then retrieving the particles with the attached complex from the washing solution as described above. In a preferred embodiment, the capturing step takes place by sequentially hybridizing the capture oligonucleotide with the target nucleic acid and then adjusting the hybridization conditions to allow hybridization of the tail portion of the capture oligonucleotide with an immobilized complementary sequence (e.g., as described in PCT No. WO 98/50583). After the capturing step and any optional washing steps have been completed, the target nucleic acid can then be amplified. To limit the number of handling steps, the target nucleic acid optionally can be amplified without releasing it from the capture oligonucleotide.

Two different regions of the HBV nucleic acid sequence are described herein as targets for capture oligonucleotides, with each region being located outside one of the oppositely disposed boundaries that define the HBV nucleic acid sequence that may be amplified by the methods described herein. The sequences of capture oligonucleotides that hybridize one of these regions are contained within a sequence substantially corresponding to AGACTCGTG-GTGGACTTCTCTCAATTTTCTAGGGG-GATCACCCGTGTGTCTTGGCCAA AATTCGCAGTC-CCCAACCTCCAATCACTCACCAAC (SEQ ID NO:68). Preferred lengths for the HBV-complementary portions of the capture oligonucleotides fall in the range of from 20-40 nucleotides, more preferably 25-30 nucleotides. Examples of useful capture oligonucleotides falling in this category include oligonucleotides having sequences given by SEQ ID NOs:70-76. The sequences of capture oligonucleotides that hybridize the other region of the HBV nucleic acid sequence are contained within a sequence substantially corresponding to CGTTTCTCTTGGCTCAGTTTACTAGTGC-CATTTGTTCAGTGGTTCGTAGGGCTTTCCCC CACT-GTTTGGCTTT (SEQ ID NO:69). Preferred sizes for these capture oligonucleotides fall in the range of from 25-50 nucleotides, more preferably 25-32 nucleotides in length. Examples of useful capture oligonucleotides falling in this category include oligonucleotides having the HBV-complementary sequences of SEQ ID NOs:77-87. Useful capture oligonucleotides may contain mismatches to the above-indicated sequences, as long as the mismatched sequences hybridize to the HBV nucleic acid containing the sequence that is to be amplified. Each capture oligonucleotide described herein included one of the HBV-complementary sequences presented in Table 4 linked to a poly-(dA) tail at its 3' end. With the exception of the oligonucleotides identified by SEQ ID NO:71 and SEQ ID NO:80, all of the capture oligonucleotides also included three thymidine nucleotides interposed between the HBV-complementary sequence and the poly-(dA) tail. As indicated below, the presence of these thymidine nucleotides is not believed to be essential for success of the capture procedure. Notably, the presence of a "C" nucleobase, rather than the naturally occurring "G" nucleobase, at position 16 of capture oligonucleotide of SEQ ID NO:86 demonstrated that at least one base substitution is permitted in the capture oligonucleotides of the present invention.

TABLE 4

Polynucleotide Sequences of HBV-Complementary Portions of Capture Oligonucleotides

| Sequence (5' to 3') | Identifier |
|---|---|
| AGACTCGTGGTGGACTTCTCTCAATTTTCTAGGGGG | SEQ ID NO: 70 |
| GTGGTGGACTTCTCTCAATTTTCTAGGGGG | SEQ ID NO: 71 |
| GGATCACCCGTGTGTCTTGG | SEQ ID NO: 72 |
| GTGTCTTGGCCAAAATTCGCAGTCC | SEQ ID NO: 73 |

TABLE 4-continued

Polynucleotide Sequences of HBV-Complementary Portions of Capture Oligonucleotides

| Sequence (5' to 3') | Identifier |
|---|---|
| GCCAAAATTCGCAGTCCCCAACCTCCAATCACTCAC CAAC | SEQ ID NO: 74 |
| GCCAAAATTCGCAGTCCCCAACCTCCA | SEQ ID NO: 75 |
| TTCGCAGTCCCCAACCTCCAATCACTC | SEQ ID NO: 76 |
| CGTTTCTCCTGGCTCAGTTTACTAGTGCCATTTGTT CAGT | SEQ ID NO: 77 |
| CGTTTCTCCTGGCTCAGTTTACTAGTGCCATTTGTT CAGTGGTCG | SEQ ID NO: 78 |
| TGGCTCAGTTTACTAGTGCCATTTGTTCAGTG | SEQ ID NO: 79 |
| TGGCTCAGTTTACTAGTGCCATTTGTTCAGTG | SEQ ID NO: 80 |
| TGGCTCAGTTTACTAGTGCCATTTGTTCAGTGGT | SEQ ID NO: 81 |
| GGCTCAGTTTACTAGTGCCATTTGTTCAGTGGTTCG | SEQ ID NO: 82 |
| GGCTCAGTTTACTAGTGCCATTTGTTCAGTGGTTCG TAGGGC | SEQ ID NO: 83 |
| GGCTCAGTTTACTAGTGCCATTTGTTCAGTGGTTCG TAGGGCTTTCCCCC | SEQ ID NO: 84 |
| GTGCCATTTGTTCAGTGGTTCGTAGGGCTTTCC | SEQ ID NO: 85 |
| GGGCTTTCCCCCACTCTTTGGCTTT | SEQ ID NO: 86 |
| GGGCTTTCCCCCACTGTTTGGCTTT | SEQ ID NO: 87 |

Preferred Methods for Amplifying and Detecting HBV Polynucleotide Sequences

Preferred methods of the present invention are described and illustrated by the Examples presented below. FIG. 1 schematically illustrates one system that may be used for detecting a target region of the HBV genome (shown by a thick solid horizontal line). This system includes four oligonucleotides (shown by the shorter solid lines): one capture oligonucleotide that includes a sequence that hybridizes specifically to an HBV sequence in the target region and a tail ("T") that hybridizes to complementary sequence immobilized on a solid support to capture the target region present in a biological sample; one T7 promoter-primer which includes a sequence that hybridizes specifically to an HBV sequence in the target region and a T7 promoter sequence ("P") which, when double-stranded, serves as a functional promoter for T7 RNA polymerase; one non-T7 primer which includes a sequence that hybridizes specifically to a first strand cDNA made from the target region sequence using the T7 promoter-primer; and one labeled probe which includes a sequence that hybridizes specifically to a portion of the target region that is amplified using the two primers.

As indicated above, amplifying the captured target region using the two primers can be accomplished by any of a variety of known nucleic acid amplification reactions that will be familiar to those having an ordinary level of skill in the art. In a preferred embodiment, a transcription-associated amplification reaction, such as TMA, is employed. In such an embodiment, many strands of nucleic acid are produced from a single copy of target nucleic acid, thus permitting detection of the target by detecting probes that are bound to the amplified sequences. Preferably, transcription-associated amplification uses two types of primers (one being referred to as a promoter-primer because it contains a promoter sequence, labeled "P" in FIG. 1, for an RNA polymerase) two enzymes (a reverse transcriptase and an RNA polymerase), and substrates (deoxyribonucleoside triphosphates, ribonucleoside triphosphates) with appropriate salts and buffers in solution to produce multiple RNA transcripts from a nucleic acid template.

Referring to FIG. 1, during transcription-mediated amplification, the captured target nucleic acid is hybridized to a first primer shown as a T7 promoter-primer. Using reverse transcriptase, a complementary DNA strand is synthesized from the T7 promoter-primer using the target DNA as a template. A second primer, shown as a non-T7 primer, hybridizes to the newly synthesized DNA strand and is extended by the action of a reverse transcriptase to form a DNA duplex, thereby forming a double-stranded T7 promoter region. T7 RNA polymerase then generates multiple RNA transcripts by using this functional T7 promoter. The autocatalytic mechanism of TMA employs repetitive hybridization and polymerization steps following a cDNA synthesis step using the RNA transcripts as templates to produce additional transcripts, thereby amplifying target region-specific nucleic acid sequences.

The detecting step uses at least one detection probe that binds specifically to the amplified RNA transcripts or amplicons described above. Preferably, the detection probe is labeled with a label that can be detected using a homogeneous detection system. For example, the labeled probe can be labeled with an acridinium ester compound from which a chemiluminescent signal may be produced and detected, as described above. Alternatively, the labeled probe may comprise fluorophore and quencher moieties. A molecular beacon is one embodiment of such a labeled probe that may be used in a homogeneous detection system.

Multiplex Amplification Reactions

A convenient testing format for detecting multiple analyte polynucleotides involves conducting simultaneous amplification reactions using different primer sets, wherein amplicons synthesized in the reaction are detected by hybridization. In this regard, Gen-Probe Incorporated (San Diego, Calif.) has developed an HIV-1/HCV test that detects HIV-1 and/or HCV (Hepatitis C Virus) nucleic acids in a single-tube multiplex format using three key steps. In an initial sample preparation procedure plasma is treated with detergent to release viral genomic RNA, target-specific oligonucleotides are hybridized to the target and captured onto magnetic microparticles which are separated from plasma in a magnetic field. Next, a transcription-based polynucleotide amplification system is employed to amplify HIV-1 and/or HCV target RNA in a single reaction. Finally, detection is accomplished using nucleic acid hybridization of chemiluminescent probes that are complementary to the HIV-1 or HCV amplicons. If the assay gives a positive result, discriminatory tests are performed to differentiate between the two viruses.

Oligonucleotides that were particularly used for amplifying and detecting HIV-1 nucleic acids in the procedures described below had the following sequences. Amplification primers specific for one strand of the HIV-1 nucleic acid included the sequences of CGGGCGCCACTGCTAGAGATTTT (SEQ ID NO:98) and GTTTGTATGTCTGTTGCTATTATGTCTA (SEQ ID NO:99), with each primer further including an optional upstream promoter sequence to give the corresponding promoter-primers of AATTTAATACGACTCACTATAGGGAGACGGGCGCCACTGCTAGAGATTTT (SEQ ID NO:100) and AATTTAATACGACTCACTATAGGGAGAGTTTGTATGTCTGTTGCTATTATGTCTA (SEQ ID NO:101). Opposite strand primers that were used during the development of the invention had the sequences of GCCTCAATAAAGCTTGCC (SEQ ID NO:102) and ACAGCAGTACAAATGGCAG (SEQ ID NO:103). Although not used for obtaining the multiplex data presented herein, preferred alternative opposite strand primers include GACAGCAGTACAAATGGCAG (SEQ ID NO:104) and AGACAGCAGTACAAATGGCAG (SEQ ID NO:105). Probes for detecting HIV amplicons had the sequences given by CCACAATTTTAAAAGAAAAGGG (SEQ ID NO:106) (labeled with AE between nucleotide positions 7 and 8), CUGGUAICUAGAGAUCCCUC (SEQ ID NO:107) (labeled with AE between nucleotide positions 9 and 10), and GGATTGGIIIGTACAGTGC (SEQ ID NO:108) (labeled with AE between nucleotide positions 5 and 6). A probe having the sequence of CCACAAGCUUAGAAGAUAGAGAGG (SEQ ID NO:109) (labeled with AE between nucleotide positions 10 and 11) was used for detecting an internal control amplicon. All of these probes were prepared using 2'-OMe analogs, except for the final position which was occupied by a DNA nucleotide, thereby confirming that the probes can be flexibly prepared using a combination of RNA and DNA equivalent bases, base analogs and nucleotide backbone analogs. Probe protection oligonucleotides had the sequences of GGATCTCTAGCTACC (SEQ ID NO:110), CCCTTTTCTTTTAAAATTGTGG (SEQ ID NO:111), and CTATCTTCTAAGCTTG (SEQ ID NO:112). Capture oligonucleotides included the HIV-complementary sequences of ACUGACGCUCUCGCACCCAUC (SEQ ID NO:113) and UCUGCUGUCCCUGUAAUAAACCCG (SEQ ID NO:114), and were prepared using 2'-OMe analogs and joined at their 3'-ends to a tail sequence of $A_{30}$ with three T residues interposed therebetween.

Preferred oligonucleotides used for amplifying and detecting HCV nucleic acids had the following sequences. An amplification primer specific for one strand of the HCV nucleic acid included the sequence of AGTACCACAAGGCCTTTCGCIACCCAAC (SEQ ID NO:115), and further included an optional upstream promoter sequence to give the corresponding promoter-primer of AATTTAATACGACTCACTATAGGGAGAAGTACCACAAGGCCTTTCGCIACCCAAC (SEQ ID NO:116). Opposite strand primers that were used during the development of the present invention had the sequences of CTAGCCATGGCGTTAGTA (SEQ ID NO:117) and CTACTGTCTTCACGCAGAAAGCG (SEQ ID NO:118). Probes for detecting HCV amplicons had the sequences given by CCCGGGAGAGCCAUAGUGGUCT (SEQ ID NO:119) (labeled with AE between nucleotide positions 14 and 15), and CTGCGGAACCGGTGAGTAC (SEQ ID NO:120) (labeled with AE between nucleotide positions 13 and 14). Detection of HCV amplicons was facilitated by the use of a helper probe having the sequence of AGCCUCCAGGACCCCCCCT (SEQ ID NO:121). As above, these probes were prepared using 2'-OMe analogs, except for the final position which was occupied by a DNA nucleotide, thereby confirming that the probes can be flexibly prepared using a combination of RNA and DNA equivalent bases, base analogs and nucleotide backbone analogs. Probe protection oligonucleotides had the sequences of GACCACTATGGCTC (SEQ ID NO:122) and GTACTCACCGGTTC (SEQ ID NO:123). Capture oligonucleotides included the HCV-complementary sequences of GGGCACUCGCAAGCACCCU (SEQ ID NO:124) and CAUGGUGCACGGUCUACG (SEQ ID NO:125), and were prepared using 2'-OMe analogs and joined at their 3'-ends to a tail sequence of $A_{30}$ with three T residues interposed therebetween.

Notably, the above-described oligonucleotides can be used under the conditions described herein for single-analyte detection. Indeed, the oligonucleotides that were used for amplifying and detecting HIV-1 can be used in a stand-alone assay for detecting HIV-1, and the oligonucleotides that were used for amplifying and detecting HCV can be used in a stand-alone assay for detecting HCV. Each of these alternative stand-alone assays represents a preferred embodiment of the present invention. Moreover, the oligonucleotides that were used for amplifying and detecting HIV-1 have been used in combination with the oligonucleotides that were used for amplifying and detecting HCV in a multiplex reaction. Again, this combination represents another preferred embodiment of the present invention. Finally, as disclosed in numerous examples herein, the HIV-1 and HCV amplifying and detecting oligonucleotides have been used in combination to prepare an assay capable of amplifying and detecting any or all of the HIV-1, HCV and HBV analytes.

As the number of different primer sets in a multiplex amplification reaction increases, with each set of primers being specific for a different analyte polynucleotide, there is an increased opportunity for undesired interaction among primers, and between primers and irrelevant amplicons. The most highly preferred primer sequences disclosed herein can be used in reactions that specifically amplify only HBV nucleic acids, and also can be used as reagents in a single polynucleotide amplification reaction that is additionally capable of amplifying virus-specific sequences from HIV-1 and HCV.

Kits for Detecting HBV Nucleic Acids

The present invention also embraces kits for performing polynucleotide amplification reactions using viral nucleic acid templates. Certain preferred kits contain a pair of oligonucleotide primers that may be used for amplifying HBV nucleic acids in an in vitro amplification reaction. Exemplary kits include first and second amplification oligonucleotides that are complementary to opposite strands of the HBV nucleic acid sequence that is to be amplified. The first amplification oligonucleotide, which is also referred to as the "first strand" primer, includes a downstream sequence complementary to one strand of the HBV nucleic acid, and optionally an upstream sequence that is not complementary to that HBV nucleic acid. Preferably, the first amplification oligonucleotide has a length of up to 100 bases, more preferably a length of from 20-60 bases, and has an HBV-complementary sequences that includes at least 20 contiguous bases, more preferably 20-50 contiguous bases, still more preferably 20-24 contiguous bases, allowing for substitution of one or more nucleotides or nitrogenous base analogs, contained within a sequence substantially corresponding to SEQ ID NO:2. Primers falling within this group include SEQ ID NOs: 22-28, and the corresponding T7 promoter-primers of SEQ ID NOs:39-45. The second amplification oligonucleotide preferably has a length of up to 100 bases, or more preferably 20-31 bases, or still more preferably 20-21 bases. This second primer, which is also referred to as the "second strand" primer, has at least 20 contiguous bases, more preferably 20-54 contiguous bases, more preferably 20-21 contiguous bases, allowing for substitution of nucleotides or nitrogenous base analogs, contained within a sequence substantially corresponding to SEQ ID NO:4. Amplification primers fulfilling these criteria include oligonucleotides having the sequences given by SEQ ID NOs:5-15. The kits may further contain one or more oligonucleotide detection probes. These probes may include at least 17 contiguous nucleotides, more preferably 17-23 contiguous nucleotides or still more preferably 17-19 contiguous nucleotides that are contained within the sequence given by SEQ ID NO:67, or the complement thereof, allowing for the presence of RNA and DNA equivalents and the substitution of nucleotide analogs. Particularly preferred probes include those having the sequences of SEQ ID NO:50, SEQ ID NO:57 and SEQ ID NO:54, although other probes disclosed herein can be used, and are intended to fall within the scope of the invention. Of course, the complements of these sequences also can be used as probes for detecting HBV sequences. Other probes that may be included in the kit are molecular beacon hybridization probes of the type described under Example 10. Still other kits in accordance with the invention may additionally include capture oligonucleotides for purifying HBV template nucleic acids away from other species prior to amplification. Example capture oligonucleotides have lengths of up to 100 nucleotides, and HBV-complementary portions that fall in the range of from at least 20 contiguous nucleotides, more preferably 20-40 contiguous nucleotides, or still more preferably 25-30 contiguous nucleotides of SEQ ID NO:68. Examples of useful capture oligonucleotides falling in this category include oligonucleotides having sequences given by SEQ ID NOs: 70-76. Alternative capture oligonucleotides have lengths of up to 100 nucleotides, and HBV-complementary portions that fall in the range of from at least 25 contiguous nucleotides, more preferably 25-50 contiguous nucleotides, or still more preferably 25-32 contiguous nucleotides of SEQ ID NO:69. Examples of useful capture oligonucleotides falling in this category include oligonucleotides having sequences given by SEQ ID NOs:77-87. Indeed, kits useful for practicing the invented method of detecting HBV nucleic acids may include, in packaged combination with one another, essentially any of the amplification oligonucleotide compositions and/or detection probe compositions and/or capture oligonucleotide compositions disclosed herein.

Other preferred kits in accordance with the invention include primers for amplifying nucleic acids of viral targets other than HBV, but that can be used in combination with the primers for amplifying HBV target nucleic acids. For example, the primers for amplifying HBV target nucleic acids may be in packaged combination with primers that can be used for amplifying HIV-1 and/or HCV target nucleic acids. Exemplary primers for amplifying HIV-1 and HCV are disclosed herein. In a particularly preferred embodiment, the kit includes primers for amplifying HBV, HIV-1 and HCV. Still other kits include primers that can be used for amplifying only one of either HIV-1 or HCV target nucleic acids. Yet other kits include the primers for amplifying both HIV-1 and HCV, but do not include primers for amplifying HBV nucleic acids. Thus, it should be clear that many different kit configurations are embraced by the present invention. Probes, primers and capture oligonucleotide sequences for amplifying and detecting HIV-1 and HCV nucleic acids are disclosed herein.

The general principles of the present invention may be more fully appreciated by reference to the following non-limiting Examples.

Example 1 describes procedures that identified hybridization probes which subsequently were used in assays for detecting HBV nucleic acids. One of seven related synthetic oligonucleotides served as a target for binding of candidate probes in this procedure.

EXAMPLE 1

Oligonucleotide Probes for Detecting HBV

Synthetic HBV target oligonucleotides were prepared according to standard laboratory procedures using RNA or 2'-0Me backbones. These targets had the following sequences: UUCCUCUUCAUCCUGCU (SEQ ID NO:88); UUCCUCUUCAUCCUGCUGCUAUGCCUCAUCUUC-UU (SEQ ID NO:89); UUCCUCUGCAUCCUGCUGC-UAUGCCUCAUCUUCUUGUUG (SEQ ID NO:90); GC- CUCAUCUUCUUGUUGG (SEQ ID NO:91); CUCAUCU-UCUUGUUGGUUCUUCUGGACUAUCAAGG (SEQ ID NO:92); UUGGUUCUUCUGGACUAUCAAGG (SEQ ID NO:93); and CAAGGUAUGUUGCCCGU (SEQ ID NO:94). Candidate probes for hybridizing the synthetic HBV targets were prepared using 2'-OMe nucleotides and had the sequences given in Table 3. Notably, position 8 of the target sequence identified by SEQ ID NO:90 was occupied by a G moiety which is characteristic of the HBV genotype B sequence.

Hybridization reactions consisted of 100 µl volumes of hybridization buffer containing amounts of AE-labeled probe corresponding to 5×10$^5$ RLUs and 10 µl containing 100 fmoles of the synthetic HBV target oligonucleotide. Negative control reactions omitted the HBV target oligonucleotide. The probes listed in Table 5 were each labeled with an AE moiety joined to the oligonucleotide structure by an internally disposed non-nucleotide linker according to procedures described in U.S. Pat. Nos. 5,585,481 and 5,639,604, the disclosures of these patents having been incorporated by reference hereinabove. Use of the different linker positions confirmed the versatility of this labeling technique. More particularly, the linker on the probe of SEQ ID NO:50 was located between positions 8 and 9, the linker on the probe of SEQ ID NO:51 was located between positions 5 and 6, the linker on the probe of SEQ ID NO:52 was located between positions 5 and 6, the linker on the probe of SEQ ID NO:53 was located between positions 11 and 12, the linker on the probe of SEQ ID NO:54 was located between positions 6 and 7 or between positions 13 and 14, the linker on the probe of SEQ ID NO:55 was located between positions 17 and 18 or between positions 8 and 9, the linker on the probe of SEQ ID NO:56 was located between positions 14 and 15, the linker on the probe of SEQ ID NO:57 was located between positions 8 and 9, the linker on the probe of SEQ ID NO:58 was located between positions 10 and 11, the linker on the probe of SEQ ID NO:59 was located between positions 13 and 14, the linker on the probe of SEQ ID NO:60 was located between positions 8 and 9, the linker on the probe of SEQ ID NO:61 was located between positions 9 and 10, the linker on the probe of SEQ ID NO:62 was located between positions 6 and 7, the linker on the probe of SEQ ID NO:63 was located between positions 14 and 15, the linker on the probe of SEQ ID NO:64 was located between positions 17 and 18, the linker on the probe of SEQ ID NO:65 was located between positions 5 and 6, and the linker on the probe of SEQ ID NO:66 was located between positions 8 and 9. Probe hybridizations were performed in 200 µl of a solution containing 0.05M lithium succinate (pH 5), 0.6M LiCl, 1% (w/v) lithium lauryl sulfate, 10 mM EDTA, 10 mM EGTA, at 60° C. for 15 minutes. Hybridization reactions were followed by addition of 300 µl of 0.15 M sodium tetraborate (pH 8.5), and 1% TRITON X-100 (Union Carbide Corporation; Danbury, Conn.). These mixtures were first incubated at 60° C. for 10 minutes to inactivate unhybridized probe, and cooled to room temperature thereafter. Chemiluminescence due to hybridized probe in each sample was assayed using a LEADER I luminometer (Gen-Probe Incorporated) configured for automatic injection of 1 mM nitric acid and 0.1% (v/v) hydrogen peroxide, followed by injection of a solution containing 1 N sodium hydroxide. Results for the chemiluminescent reactions were measured in relative light units (RLU). Sample results from this procedure are presented in Table 5.

TABLE 5

Probe Hybridization Results

| Probe | Synthetic HBV Target | Negative Control (RLU) | Hybridization Signal (RLU) |
|---|---|---|---|
| SEQ ID NO: 50 | SEQ ID NO: 88 | 825 | 480,563 |
| SEQ ID NO: 51 | SEQ ID NO: 90 | 1004 | 443,434 |
| SEQ ID NO: 52 | SEQ ID NO: 89 | 785 | 423,935 |
| SEQ ID NO: 53 | SEQ ID NO: 90 | 945 | 447,499 |
| SEQ ID NO: 54 | SEQ ID NO: 90 | 623 | 501,532 |
| SEQ ID NO: 55 | SEQ ID NO: 90 | 427 | 458,790 |
| SEQ ID NO: 56 | SEQ ID NO: 90 | 447 | 392,360 |
| SEQ ID NO: 57 | SEQ ID NO: 90 | 394 | 659,028 |
| SEQ ID NO: 58 | SEQ ID NO: 90 | 516 | 497,271 |
| SEQ ID NO: 59 | SEQ ID NO: 91 | 698 | 476,324 |
| SEQ ID NO: 60 | SEQ ID NO: 92 | 407 | 242,711 |
| SEQ ID NO: 61 | SEQ ID NO: 92 | 472 | 220,587 |
| SEQ ID NO: 62 | SEQ ID NO: 92 | 447 | 206,988 |
| SEQ ID NO: 63 | SEQ ID NO: 93 | 371 | 99,625 |
| SEQ ID NO: 64 | SEQ ID NO: 93 | 386 | 79,736 |
| SEQ ID NO: 65 | SEQ ID NO: 94 | 415 | 14,415 |
| SEQ ID NO: 66 | SEQ ID NO: 94 | 432 | 41,528 |

The results presented in Table 5 showed that each probe gave a low background signal and at least a moderate level of positive reaction with the HBV target oligonucleotide. However, some of the probes gave results that were substantially better than others, thereby defining a preferred target region for probe binding in the HBV sequence. More particularly, with the exception of the probes of SEQ ID NOs:65-66, all of the probes gave negative control values that were less than 0.5% of the corresponding probe hybridization signals. Based on this pattern, preferred probes for hybridizing and detecting HBV amplicons include 17-23 contiguous nucleotides contained within the sequence given by CCTTGATAGTCCA-GAAGAACCAACAAGAAGATGAGGCATAGCAGCAG-GATGCAGAGGAA (SEQ ID NO:95), or the complement thereof, allowing for RNA and DNA equivalents and the presence of nucleotide analogs. Notably, while the result presented for the probe of SEQ ID NO:54 was for the oligonucleotide having a linker located between positions 6 and 7, substantially identical results were obtained for a probe having an identical nucleobase sequence with a linker located between positions 13 and 14. Each of these alternatives represents a preferred embodiment of the invented probe. Further, while the result presented in the table for the probe of SEQ ID NO:55 was for the oligonucleotide having a linker located between positions 17 and 18, good, but somewhat lower values were obtained for a probe having an identical nucleobase sequence with a linker located between positions 8 and 9. Each of these alternatives also represents a preferred embodiment of the invented probe. Indeed, the positioning of any detectable label joined to any of the above-described probes can be varied and still fall within the scope of the invention.

Hybridization assay probes having the sequences of SEQ ID NO:50, SEQ ID NO:52, SEQ ID NO:54 (using a combination of separate oligonucleotides having the two above-described label positions), SEQ ID NO:57, and SEQ ID NO:58 were subsequently used for demonstrating that a range of amplification primers and capture oligonucleotides could detect HBV nucleic acids in biological samples. Probes having these sequences or their complements, allowing for the presence of RNA and DNA equivalents and nucleotide analog substitutions, each represent particularly preferred embodiments of the invention.

Preferred primer combinations for amplifying HBV nucleic acids were identified in a series of procedures that employed HBV virions as the source of nucleic acid templates. Promoter-primers and opposite strand primers were screened in combination using the method described below. Although these procedures were particularly carried out using a Transcription Mediated Amplification (TMA) protocol, the primers disclosed herein may be used to produce amplicons by alternative in vitro nucleic acid amplification methods that will be familiar to those having an ordinary level of skill in the art.

Example 2 describes the methods that identified useful amplification primers. In addition to the HBV-specific target capture oligonucleotides, amplification primers and probes described in this procedure, the reactions also included the above-described oligonucleotides specific for the HIV-1 and HCV analytes. The HIV-1 and HCV oligonucleotides did not substantially contribute to detection of the HBV analyte.

EXAMPLE 2

Identification of Amplification Primers

HBV genotype A virions served as the source of HBV template sequences in amplification reactions that employed paired sets of primers. TMA reactions were carried out essentially as described by Kacian et al., in U.S. Pat. No. 5,399,491, the disclosure of this U.S. patent having been incorporated by reference hereinabove. Each promoter-primer included a T7 promoter sequence AATTTAATACGACTCACTATAGG-GAGA (SEQ ID NO:96) upstream of an HBV-complementary sequence. Amplification reactions were conducted for various primer combinations using between about 7 and 33 copies of the HBV template, and 1-20 pmoles of each primer in 100 µl of reaction buffer. Nucleic acids underwent specimen processing and target capture prior to amplification essentially according to the procedures disclosed in published International Patent Application No. PCT/US2000/18685, except that the template was captured using HBV-specific oligonucleotides rather than HIV-specific oligonucleotides. Significantly, all of the capture oligonucleotides used in the procedure were known to be capable of capturing HBV templates that could be amplified. Accordingly, this procedure focused on the ability of the different primer and probe combinations to cooperate in a multiplex amplification assay. All procedures were conducted using 500 µl aliquots of stock samples of infected serum containing 5-25 international units/ml (IU/ml) of HBV. Notably, there are approximately 3 copies of the HBV genome in one IU of the virion preparation used in this procedure. Target nucleic acids and primers were heated to 60° C. for 10 minutes and then cooled to 42° C. to facilitate primer annealing. Moloney Murine Leukemia Virus (MMLV) reverse transcriptase (5,600 units/reaction) and T7 RNA polymerase (3,500 units/reaction) were then added to the mixtures. The final amplification reactions contained 50 mM Tris HCl (pH 8.5), 35 mM KCl, 4 mM GTP, 4 mM ATP, 4 mM UTP, 4 mM CTP, 1 mM dATP, 1 mM dTTP, 1 mM dCTP, 1 mM dGTP, 20 mM $MgCl_2$, 20 mM N-Acetyl-L-Cysteine, and 5% (w/v) glycerol. After a one hour incubation at 42° C., the entire 100 µl amplification reaction was subjected to a hybridization assay essentially as described in Example 1. More particularly, one or more of six different probes listed in Table 3 were labeled with acridinium ester to a specific activity of about $1-1.2 \times 10^8$ RLU/pmol and then used in an amount equivalent to $7.5 \times 10^5$ RLU for each probe used in the hybridization reaction. To be judged as a positive result, the chemiluminescent signal indicating probe hybridization must have exceeded 50,000 RLU in an assay.

Table 6 presents results from amplification procedures that were conducted using different combinations of primers, probes and input levels of the HBV template. Results in the last column of the table are shown as % positive detection, and additionally indicate the number of replicate trials used in the procedure. These results were collected from a number of procedures that were not necessarily carried out contemporaneously.

TABLE 6

Amplification of HBV Polynucleotide Sequences Using Various Primer Combinations

| HBV-Complementary Sequence(s) of the Promoter-Primer(s) | Opposite Strand Primer(s) | Probe(s) | HBV genotype A (copies) | % Positive (# Tested) |
|---|---|---|---|---|
| SEQ ID NO: 24 | SEQ ID NO: 5 SEQ ID NO: 15 | SEQ ID NO: 58 | 20 | 100% (20) |
| SEQ ID NO: 24 SEQ ID NO: 17 | SEQ ID NO: 5 SEQ ID NO: 15 | SEQ ID NO: 58 | 20 | 100% (20) |
| SEQ ID NO: 20 | SEQ ID NO: 5 SEQ ID NO: 15 | SEQ ID NO: 52 SEQ ID NO: 58 | 20 | 95% (20) |
| SEQ ID NO: 20 SEQ ID NO: 24 | SEQ ID NO: 5 SEQ ID NO: 15 | SEQ ID NO: 52 SEQ ID NO: 58 | 20 | 100% (20) |
| SEQ ID NO: 25 | SEQ ID NO: 5 SEQ ID NO: 15 | SEQ ID NO: 58 | 13 | 75% (20) |
| SEQ ID NO: 25 SEQ ID NO: 20 | SEQ ID NO: 5 SEQ ID NO: 15 | SEQ ID NO: 58 | 13 | 90% (20) |
| SEQ ID NO: 25 | SEQ ID NO: 6 SEQ ID NO: 15 | SEQ ID NO: 58 | 13 | 60% (20) |
| SEQ ID NO: 25 SEQ ID NO: 20 | SEQ ID NO: 6 SEQ ID NO: 15 | SEQ ID NO: 58 | 13 | 80% (20) |
| SEQ ID NO: 25 | SEQ ID NO: 7 SEQ ID NO: 15 | SEQ ID NO: 58 | 13 | 35% (20) |
| SEQ ID NO: 25 SEQ ID NO: 20 | SEQ ID NO: 7 SEQ ID NO: 15 | SEQ ID NO: 58 | 13 | 95% (20) |

TABLE 6-continued

Amplification of HBV Polynucleotide Sequences Using Various Primer Combinations

| HBV-Complementary Sequence(s) of the Promoter-Primer(s) | Opposite Strand Primer(s) | Probe(s) | HBV genotype A (copies) | % Positive (# Tested) |
|---|---|---|---|---|
| SEQ ID NO: 24 | SEQ ID NO: 8 SEQ ID NO: 15 | SEQ ID NO: 58 | 20 | 90% (20) |
| SEQ ID NO: 24 SEQ ID NO: 17 | SEQ ID NO: 8 SEQ ID NO: 15 | SEQ ID NO: 58 | 20 | 100% (20) |
| SEQ ID NO: 20 | SEQ ID NO: 8 SEQ ID NO: 15 | SEQ ID NO: 52 SEQ ID NO: 58 | 20 | 95% (20) |
| SEQ ID NO: 20 SEQ ID NO: 24 | SEQ ID NO: 8 SEQ ID NO: 15 | SEQ ID NO: 58 | 20 | 100% (20) |
| SEQ ID NO: 25 | SEQ ID NO: 8 SEQ ID NO: 15 | SEQ ID NO: 58 | 13 | 50% (20) |
| SEQ ID NO: 25 SEQ ID NO: 20 | SEQ ID NO: 8 SEQ ID NO: 15 | SEQ ID NO: 58 | 13 | 85% (20) |
| SEQ ID NO: 25 SEQ ID NO: 17 | SEQ ID NO: 8 SEQ ID NO: 15 | SEQ ID NO: 58 | 13 | 85% (20) |
| SEQ ID NO: 24 | SEQ ID NO: 9 SEQ ID NO: 15 | SEQ ID NO: 58 | 20 | 95% (20) |
| SEQ ID NO: 24 SEQ ID NO: 17 | SEQ ID NO: 9 SEQ ID NO: 15 | SEQ ID NO: 58 | 20 | 100% (20) |
| SEQ ID NO: 20 | SEQ ID NO: 9 SEQ ID NO: 15 | SEQ ID NO: 52 SEQ ID NO: 58 | 20 | 85% (20) |
| SEQ ID NO: 20 SEQ ID NO: 24 | SEQ ID NO: 9 SEQ ID NO: 15 | SEQ ID NO: 58 | 20 | 100% (20) |
| SEQ ID NO: 24 | SEQ ID NO: 10 SEQ ID NO: 15 | SEQ ID NO: 58 | 20 | 85% (20) |
| SEQ ID NO: 24 SEQ ID NO: 17 | SEQ ID NO: 10 SEQ ID NO: 15 | SEQ ID NO: 58 | 20 | 95% (20) |
| SEQ ID NO: 20 | SEQ ID NO: 10 SEQ ID NO: 15 | SEQ ID NO: 52 SEQ ID NO: 58 | 20 | 80% (20) |
| SEQ ID NO: 20 SEQ ID NO: 24 | SEQ ID NO: 10 SEQ ID NO: 15 | SEQ ID NO: 58 | 20 | 95% (20) |
| SEQ ID NO: 20 SEQ ID NO: 25 | SEQ ID NO: 11 | SEQ ID NO: 58 | 13 | 95% (20) |
| SEQ ID NO: 22 | SEQ ID NO: 11 | SEQ ID NO: 50 SEQ ID NO: 57 | 33 | 70% (10) |
| SEQ ID NO: 23 | SEQ ID NO: 11 | SEQ ID NO: 52 SEQ ID NO: 58 | 33 | 85% (20) |
| SEQ ID NO: 22 SEQ ID NO: 23 | SEQ ID NO: 11 | SEQ ID NO: 50 SEQ ID NO: 57 | 33 | 70% (10) |
| SEQ ID NO: 23 | SEQ ID NO: 12 | SEQ ID NO: 50 SEQ ID NO: 57 | 20 | 70% (10) |
| SEQ ID NO: 20 | SEQ ID NO: 12 | SEQ ID NO: 50 SEQ ID NO: 57 | 20 | 0% (10) |
| SEQ ID NO: 17 | SEQ ID NO: 12 | SEQ ID NO: 50 SEQ ID NO: 57 | 20 | 60% (10) |
| SEQ ID NO: 23 SEQ ID NO: 20 | SEQ ID NO: 12 | SEQ ID NO: 50 SEQ ID NO: 57 | 20 | 0% (20) |
| SEQ ID NO: 23 SEQ ID NO: 17 | SEQ ID NO: 12 | SEQ ID NO: 50 SEQ ID NO: 57 | 20 | 95% (20) |
| SEQ ID NO: 20 SEQ ID NO: 17 | SEQ ID NO: 12 | SEQ ID NO: 50 SEQ ID NO: 57 | 20 | 0% (20) |
| SEQ ID NO: 23 | SEQ ID NO: 13 | SEQ ID NO: 50 SEQ ID NO: 57 | 20 | 90% (10) |
| SEQ ID NO: 20 | SEQ ID NO: 13 | SEQ ID NO: 50 SEQ ID NO: 57 | 20 | 20% (10) |
| SEQ ID NO: 17 | SEQ ID NO: 13 | SEQ ID NO: 50 SEQ ID NO: 57 | 20 | 50% (10) |
| SEQ ID NO: 23 SEQ ID NO: 20 | SEQ ID NO: 13 | SEQ ID NO: 50 SEQ ID NO: 57 | 20 | 0% (20) |
| SEQ ID NO: 23 SEQ ID NO: 17 | SEQ ID NO: 13 | SEQ ID NO: 50 SEQ ID NO: 57 | 20 | 10% (20) |
| SEQ ID NO: 20 SEQ ID NO: 17 | SEQ ID NO: 13 | SEQ ID NO: 50 SEQ ID NO: 57 | 20 | 0% (20) |
| SEQ ID NO: 23 | SEQ ID NO: 14 | SEQ ID NO: 50 SEQ ID NO: 57 | 20 | 80% (10) |
| SEQ ID NO: 20 | SEQ ID NO: 14 | SEQ ID NO: 50 SEQ ID NO: 57 | 20 | 70% (10) |
| SEQ ID NO: 17 | SEQ ID NO: 14 | SEQ ID NO: 50 SEQ ID NO: 57 | 20 | 70% (10) |
| SEQ ID NO: 23 SEQ ID NO: 20 | SEQ ID NO: 14 | SEQ ID NO: 50 SEQ ID NO: 57 | 20 | 95% (20) |
| SEQ ID NO: 23 SEQ ID NO: 17 | SEQ ID NO: 14 | SEQ ID NO: 50 SEQ ID NO: 57 | 20 | 10% (20) |

TABLE 6-continued

Amplification of HBV Polynucleotide Sequences Using Various Primer Combinations

| HBV-Complementary Sequence(s) of the Promoter-Primer(s) | Opposite Strand Primer(s) | Probe(s) | HBV genotype A (copies) | % Positive (# Tested) |
|---|---|---|---|---|
| SEQ ID NO: 20<br>SEQ ID NO: 17 | SEQ ID NO: 14 | SEQ ID NO: 50<br>SEQ ID NO: 57 | 20 | 0%<br>(20) |
| SEQ ID NO: 23 | SEQ ID NO: 15 | SEQ ID NO: 50<br>SEQ ID NO: 57 | 20 | 90%<br>(10) |
| SEQ ID NO: 20 | SEQ ID NO: 15 | SEQ ID NO: 50<br>SEQ ID NO: 57 | 20 | 80%<br>(10) |
| SEQ ID NO: 17 | SEQ ID NO: 15 | SEQ ID NO: 50<br>SEQ ID NO: 57 | 20 | 40%<br>(10) |
| SEQ ID NO: 23<br>SEQ ID NO: 20 | SEQ ID NO: 15 | SEQ ID NO: 50<br>SEQ ID NO: 57 | 20 | 45%<br>(20) |
| SEQ ID NO: 23<br>SEQ ID NO: 17 | SEQ ID NO: 15 | SEQ ID NO: 50<br>SEQ ID NO: 57 | 20 | 80%<br>(20) |
| SEQ ID NO: 20<br>SEQ ID NO: 17 | SEQ ID NO: 15 | SEQ ID NO: 50<br>SEQ ID NO: 57 | 20 | 0%<br>(20) |
| SEQ ID NO: 24 | SEQ ID NO: 15 | SEQ ID NO: 52<br>SEQ ID NO: 58 | 20 | 100%<br>(10) |
| SEQ ID NO: 25 | SEQ ID NO: 15 | SEQ ID NO: 52<br>SEQ ID NO: 58 | 20 | 100%<br>(10) |
| SEQ ID NO: 27 | SEQ ID NO: 15 | SEQ ID NO: 52<br>SEQ ID NO: 58 | 20 | 100%<br>(10) |
| SEQ ID NO: 28 | SEQ ID NO: 15 | SEQ ID NO: 52<br>SEQ ID NO: 58 | 20 | 100%<br>(10) |
| SEQ ID NO: 24 | SEQ ID NO: 15 | SEQ ID NO: 52<br>SEQ ID NO: 58 | 13 | 80%<br>(10) |
| SEQ ID NO: 25 | SEQ ID NO: 15 | SEQ ID NO: 52<br>SEQ ID NO: 58 | 13 | 100%<br>(10) |
| SEQ ID NO: 27 | SEQ ID NO: 15 | SEQ ID NO: 52<br>SEQ ID NO: 58 | 13 | 100%<br>(10) |
| SEQ ID NO: 28 | SEQ ID NO: 15 | SEQ ID NO: 52<br>SEQ ID NO: 58 | 13 | 100%<br>(10) |
| SEQ ID NO: 22 | SEQ ID NO: 15 | SEQ ID NO: 50<br>SEQ ID NO: 57 | 33 | 90%<br>(10) |
| SEQ ID NO: 22<br>SEQ ID NO: 23 | SEQ ID NO: 15 | SEQ ID NO: 50<br>SEQ ID NO: 57 | 33 | 100%<br>(10) |
| SEQ ID NO: 23<br>SEQ ID NO: 26 | SEQ ID NO: 15<br>SEQ ID NO: 11 | SEQ ID NO: 54 | 20 | 100%<br>(30) |
| SEQ ID NO: 23<br>SEQ ID NO: 26 | SEQ ID NO: 15<br>SEQ ID NO: 11 | SEQ ID NO: 54 | 7 | 85%<br>(20) |
| SEQ ID NO: 21 | SEQ ID NO: 15<br>SEQ ID NO: 11 | SEQ ID NO: 50<br>SEQ ID NO: 57 | 33 | 100%<br>(20) |
| SEQ ID NO: 29 | SEQ ID NO: 15 | SEQ ID NO: 54 | 20 | 90%<br>(20) |
| SEQ ID NO: 29 | SEQ ID NO: 11 | SEQ ID NO: 54 | 20 | 90%<br>(20) |
| SEQ ID NO: 30 | SEQ ID NO: 15 | SEQ ID NO: 54 | 20 | 100%<br>(20) |
| SEQ ID NO: 30 | SEQ ID NO: 11 | SEQ ID NO: 54 | 20 | 100%<br>(20) |
| SEQ ID NO: 31 | SEQ ID NO: 15 | SEQ ID NO: 54 | 20 | 95%<br>(20) |
| SEQ ID NO: 31 | SEQ ID NO: 11 | SEQ ID NO: 54 | 20 | 95%<br>(20) |
| SEQ ID NO: 32 | SEQ ID NO: 15 | SEQ ID NO: 54 | 20 | 95%<br>(20) |
| SEQ ID NO: 32 | SEQ ID NO: 11 | SEQ ID NO: 54 | 20 | 95%<br>(20) |
| SEQ ID NO: 16 | SEQ ID NO: 15 | SEQ ID NO: 52<br>SEQ ID NO: 58 | 50<br>M13 Template | 60%<br>(10) |
| SEQ ID NO: 18 | SEQ ID NO: 15 | SEQ ID NO: 52<br>SEQ ID NO: 58 | 50<br>M13 Template | 70%<br>(10) |
| SEQ ID NO: 19 | SEQ ID NO: 15 | SEQ ID NO: 52<br>SEQ ID NO: 58 | 50<br>M13 Template | 90%<br>(10) |

The results presented in Table 6 showed that many of the primer combinations gave very high levels of HBV detectability, even at template levels as low as 7 copies/reaction. Significantly, results indicating that HBV templates could be detected in these assays, demonstrated that the relevant primer combinations could cooperate to amplify HBV nucleic acid sequences, and further demonstrated that other constituents of the HIV/HCV multiplex reaction did not interfere with the ability of the HBV primer combinations to function in the complex reaction mixture. Positive results, meaning that a non-zero level of HBV detectability was observed in a trial, indicated that a combination of primers was useful in an assay that amplified HBV only, as well as in a multiplex assay that was capable of amplifying HIV-1 and HCV templates. Negative results that indicated amplification and detection of HBV sequences did not take place were relevant only to the multiplex assay. Negative results may have been due, for example, to an undesirable interaction between the HBV primers and the primers used for amplifying one of the other viral targets in the multiplex reaction. As supported by the sensitivity data appearing below, primer combinations that gave low, but measurable levels of HBV detectability in the results presented herein indicated successful amplification of HBV templates and established the combination as a useful component of an HBV nucleic acid amplification assay. Other primers contained within the upstream and downstream domains defined by these useful primers also can be used for amplifying HBV sequences.

The results presented in Table 6 further indicated that promoter-primers which included the HBV-complementary sequences of SEQ ID NO:16, SEQ ID NO:18, or SEQ ID NO:19 participated in amplification reactions that gave good levels of detectability, even when the reactions included only a single promoter-primer and when a single-stranded M13 clone was the source of HBV genotype A templates. This result differed somewhat from the apparent requirement for two promoter-primers when a single-stranded M13 clone served as the source of HBV genotype G templates, as indicated by the results appearing in Table 9. While not wishing to be bound by any particular theory, the comparatively good results observed in only some instances when single promoter-primers were used in conjunction with single-stranded M13 templates may have reflected different levels of assay sensitivity.

In certain preferred embodiments, a set of at least two primers for amplifying HBV nucleic acid is provided which includes: (i) a first amplification primer comprising an oligonucleotide having or substantially corresponding to the base sequence of SEQ ID NO:22 or SEQ ID NO:23; and (ii) a second amplification primer comprising an oligonucleotide having or substantially corresponding to the base sequence of SEQ ID NO:15 or SEQ ID NO:11. Optional sequences that are non-complementary to the HBV target sequence, such as a promoter sequence that is not present in the HBV genome, may be appended to the primers at positions located upstream of the target-complementary sequences. In a particularly preferred combination, the first amplification primer is a promoter-primer that comprises an oligonucleotide having or substantially corresponding to the base sequence of SEQ ID NO:23 (e.g., SEQ ID NO:40), and the second amplification primer comprises an oligonucleotide having or substantially corresponding to the base sequence of SEQ ID NO:11.

As in the previous Example, procedures that identified useful capture oligonucleotides also employed stocks of HBV genotype A-positive plasma as the source of HBV nucleic acid. Each oligonucleotide that underwent testing included an HBV-specific sequence linked to an oligo-(dA) tail sequence. When combined with the HBV target and magnetic particles that displayed oligo-(dT), functional capture oligonucleotides bridged the HBV DNA and the particle, thereby immobilizing the HBV target. Removing the particulate complexes from solution represented a means for enriching the HBV template. In the procedure described below, capture oligonucleotides were contacted with the HBV DNA and magnetic particles modified with oligo-(dT). Collected particles were washed, the bound HBV sequences amplified in an in vitro nucleic acid amplification reaction, and the resulting amplification products detected in homogenous protection assays. Positive results indicated that the capture oligonucleotide had immobilized the HBV DNA target onto the magnetic particle during the target capture step, and that the amplification and detection steps were successful.

The following Example describes the methods used for testing candidate HBV capture oligonucleotides. In addition to the HBV-specific target capture, amplification primer, and probes described in this procedure, the reactions also included the above-described oligonucleotides specific for the HIV-1 and HCV analytes. The HIV-1 and HCV oligonucleotides did not substantially contribute to detection of the HBV analyte.

EXAMPLE 3

Detection of HBV Target Sequences Using Different Capture Oligonucleotides

HBV-infected plasma samples having volumes of 500 µl and containing 6-20 copies of the HBV genome were dispersed in 400 µl of lysis/capture reagent containing a total of 1.6 pmoles of capture oligonucleotide (either 1.6 pmoles of a single capture oligonucleotide, 0.8 pmoles of each of two capture oligonucleotides, or 0.53 pmoles of each of three capture oligonucleotides) and about 40 µg of 0.7-1.05 p paramagnetic particles (Seradyn, Indianapolis, Ind.) covalently linked to poly-($dT_{14}$). Capture oligonucleotides used in the procedure had the sequences given in Table 4. The lysis/capture reagent further included an HIV-1 internal amplification control template, HIV-1 and HCV-specific capture oligonucleotides, and a 100 mM HEPES-buffered solution containing 294 mM lithium lauryl sulfate, 730 mM lithium chloride, and 50 mM lithium hydroxide. As stated above, a 5'-TTT-3' spacer sequence was interposed between the HBV-complementary sequence and the oligo-(dA) tail region for each of the capture oligonucleotides shown in Table 4, except for those that included the sequences of SEQ ID NO:71 and SEQ ID NO:80. Notably, testing of some capture oligonucleotides having identical sequences except for the presence or absence of the 5'-TTT-3' sequence gave substantially similar results, thereby indicating that the spacer sequence was optional. The mixtures were heated to 55-60° C. for about 15-30 minutes, and then cooled to room temperature to allow hybridization. A magnetic field was applied to collect the particle complexes containing the immobilized capture oligonucleotide and HBV DNA using procedures such as those described by Wang in U.S. Pat. No. 4,895,650. The particles were washed twice with 1 ml of a washing buffer (10 mM HEPES, 6.5 mM NaOH, 1 mM EDTA, 0.3% (v/v) ethanol, 0.02% (w/v) methyl-paraben, 0.01% (w/v) propyl-paraben, 150 mM NaCl, 0.1% (w/v) sodium lauryl sulfate). Washed particles were then resuspended in 75 p. 1 of the amplification reagent described under Example 2. This reagent included salts, nucleotides, ribonucleotides, HBV-specific primers, as well as primers capable of amplifying HIV-1 and HCV target sequences. The HBV target nucleic acid was then amplified, and the amplification products detected using a homogenous protection assay, essentially as described under Example 1. Reactions that gave positive signals when hybridized with a probe specific for the internal control amplicon, or with a probe specific for the HBV amplicon, were scored as valid runs. In order for a valid run to be considered positive for the presence of HBV amplicons, the chemiluminescent signal indicating probe hybridization must have exceeded 50,000 RLU in an assay.

Table 7 presents sample results correlating the identity of the HBV-specific capture oligonucleotide(s) and the ability of the system to amplify and detect HBV sequences efficiently. To achieve a positive result in the amplification reactions, the HBV capture oligonucleotide must have been able to act cooperatively with the amplification primers and probe(s) to capture HBV template nucleic acids, amplify the HBV template nucleic acids, and then detect the amplified nucleic acids. However, the experimental design also required that primers used for amplifying HIV-1 and HCV target nucleic acids would not substantially interfere with the capture, amplification and detection of HBV template nucleic acids. Thus, positive results identified combinations of capture oligonucleotides, amplification primers and detection probes that were functional not only in an HBV-specific assay, but also in the context of a multiplex reaction capable of amplifying HIV-1 and HCV target nucleic acids.

Notably, promoter-primers used in this procedure and listed in Table 7 are identified by the complete sequence that included the T7 promoter. It is to be understood however, that the HBV-complementary portions of the promoter-primers represent essential sequences for performing amplification reactions by alternative protocols, such as the polymerase chain reaction, with the promoter sequence being optional. Thus, it is to be understood that SEQ ID NOs:33-49 possess optional promoter sequences, and that the corresponding SEQ ID NOs:16-32 represent the respective essential HBV-complementary sequences. These latter HBV-complementary sequences are useful in conjunction with opposite strand primers for amplifying HBV nucleic acids.

TABLE 7

Efficiency of HBV Detection Using Different Combinations of Capture Oligonucleotides, Amplification Primers and Detection Probes

| Capture Oligonucleotide(s) | Amplification Primers | Detection Probe(s) | Template Copy No. | % Positive (# Valid Runs) |
|---|---|---|---|---|
| SEQ ID NO: 70<br>SEQ ID NO: 80 | SEQ ID NO: 39<br>SEQ ID NO: 40<br>SEQ ID NO: 15<br>SEQ ID NO: 11 | SEQ ID NO: 50<br>SEQ ID NO: 57 | 6.7 | 53%<br>(40) |
| SEQ ID NO: 70<br>SEQ ID NO: 86 | SEQ ID NO: 40<br>SEQ ID NO: 15 | SEQ ID NO: 52<br>SEQ ID NO: 58 | 20 | 85%<br>(80) |
| SEQ ID NO: 71 | SEQ ID NO: 40<br>SEQ ID NO: 15 | SEQ ID NO: 50<br>SEQ ID NO: 57 | 20 | 30%<br>(20) |
| SEQ ID NO: 71<br>SEQ ID NO: 78 | SEQ ID NO: 39<br>SEQ ID NO: 40<br>SEQ ID NO: 15<br>SEQ ID NO: 11 | SEQ ID NO: 50<br>SEQ ID NO: 57 | 6 | 33%<br>(18) |
| SEQ ID NO: 71<br>SEQ ID NO: 80 | SEQ ID NO: 40<br>SEQ ID NO: 15 | SEQ ID NO: 50<br>SEQ ID NO: 57 | 20 | 95%<br>(20) |
| SEQ ID NO: 71<br>SEQ ID NO: 80 | SEQ ID NO: 39<br>SEQ ID NO: 40<br>SEQ ID NO: 15<br>SEQ ID NO: 11 | SEQ ID NO: 50<br>SEQ ID NO: 57 | 12 | 60%<br>(20) |
| SEQ ID NO: 71<br>SEQ ID NO: 80 | SEQ ID NO: 40<br>SEQ ID NO: 15 | SEQ ID NO: 50<br>SEQ ID NO: 57 | 6.7 | 32%<br>(19) |
| SEQ ID NO: 71<br>SEQ ID NO: 82 | SEQ ID NO: 40<br>SEQ ID NO: 15 | SEQ ID NO: 50<br>SEQ ID NO: 57 | 6.7 | 31%<br>(45) |
| SEQ ID NO: 71<br>SEQ ID NO: 86 | SEQ ID NO: 40<br>SEQ ID NO: 15 | SEQ ID NO: 52<br>SEQ ID NO: 58 | 20 | 84%<br>(80) |
| SEQ ID NO: 71<br>SEQ ID NO: 86 | SEQ ID NO: 39<br>SEQ ID NO: 40<br>SEQ ID NO: 15<br>SEQ ID NO: 11 | SEQ ID NO: 50<br>SEQ ID NO: 57 | 12 | 90%<br>(20) |
| SEQ ID NO: 72 | SEQ ID NO: 40<br>SEQ ID NO: 15<br>SEQ ID NO: 43<br>SEQ ID NO: 11 | SEQ ID NO: 54 | 20 | 62%<br>(60) |
| SEQ ID NO: 72<br>SEQ ID NO: 80<br>SEQ ID NO: 87 | SEQ ID NO: 40<br>SEQ ID NO: 15<br>SEQ ID NO: 43<br>SEQ ID NO: 11 | SEQ ID NO: 54 | 20 | 98%<br>(60) |
| SEQ ID NO: 73 | SEQ ID NO: 40<br>SEQ ID NO: 15 | SEQ ID NO: 52<br>SEQ ID NO: 58 | 20 | 36%<br>(45) |
| SEQ ID NO: 73<br>SEQ ID NO: 80 | SEQ ID NO: 40<br>SEQ ID NO: 15 | SEQ ID NO: 52<br>SEQ ID NO: 58 | 20 | 84%<br>(45) |
| SEQ ID NO: 73<br>SEQ ID NO: 80<br>SEQ ID NO: 87 | SEQ ID NO: 40<br>SEQ ID NO: 15<br>SEQ ID NO: 43<br>SEQ ID NO: 11 | SEQ ID NO: 54 | 20 | 100%<br>(60) |
| SEQ ID NO: 73<br>SEQ ID NO: 80<br>SEQ ID NO: 87 | SEQ ID NO: 40<br>SEQ ID NO: 15<br>SEQ ID NO: 43<br>SEQ ID NO: 11 | SEQ ID NO: 54 | 6.7 | 70%<br>(60) |
| SEQ ID NO: 74 | SEQ ID NO: 40<br>SEQ ID NO: 15 | SEQ ID NO: 50<br>SEQ ID NO: 57 | 20 | 50%<br>(20) |
| SEQ ID NO: 74 | SEQ ID NO: 40<br>SEQ ID NO: 15 | SEQ ID NO: 50<br>SEQ ID NO: 57 | 6.7 | 5%<br>(20) |
| SEQ ID NO: 74<br>SEQ ID NO: 85 | SEQ ID NO: 40<br>SEQ ID NO: 15 | SEQ ID NO: 52<br>SEQ ID NO: 58 | 20 | 88%<br>(80) |
| SEQ ID NO: 74<br>SEQ ID NO: 86 | SEQ ID NO: 40<br>SEQ ID NO: 15 | SEQ ID NO: 50<br>SEQ ID NO: 57 | 20 | 100%<br>(20) |

TABLE 7-continued

Efficiency of HBV Detection Using Different Combinations of Capture Oligonucleotides, Amplification Primers and Detection Probes

| Capture Oligonucleotide(s) | Amplification Primers | Detection Probe(s) | Template Copy No. | % Positive (# Valid Runs) |
|---|---|---|---|---|
| SEQ ID NO: 76 | SEQ ID NO: 40<br>SEQ ID NO: 15 | SEQ ID NO: 52<br>SEQ ID NO: 58 | 20 | 60%<br>(45) |
| SEQ ID NO: 77 | SEQ ID NO: 40<br>SEQ ID NO: 15 | SEQ ID NO: 50<br>SEQ ID NO: 57 | 20 | 35%<br>(20) |
| SEQ ID NO: 78<br>SEQ ID NO: 86 | SEQ ID NO: 40<br>SEQ ID NO: 15 | SEQ ID NO: 52<br>SEQ ID NO: 58 | 20 | 88%<br>(77) |
| SEQ ID NO: 80 | SEQ ID NO: 40<br>SEQ ID NO: 15 | SEQ ID NO: 50<br>SEQ ID NO: 57 | 20 | 26%<br>(19) |
| SEQ ID NO: 80<br>SEQ ID NO: 87 | SEQ ID NO: 40<br>SEQ ID NO: 15 | SEQ ID NO: 52<br>SEQ ID NO: 58 | 20 | 74%<br>(90) |
| SEQ ID NO: 81<br>SEQ ID NO: 86 | SEQ ID NO: 40<br>SEQ ID NO: 15 | SEQ ID NO: 52<br>SEQ ID NO: 58 | 20 | 79%<br>(80) |
| SEQ ID NO: 82 | SEQ ID NO: 40<br>SEQ ID NO: 15 | SEQ ID NO: 50<br>SEQ ID NO: 57 | 20 | 60%<br>(20) |
| SEQ ID NO: 84 | SEQ ID NO: 40<br>SEQ ID NO: 15 | SEQ ID NO: 50<br>SEQ ID NO: 57 | 20 | 40%<br>(20) |
| SEQ ID NO: 75 | SEQ ID NO: 40<br>SEQ ID NO: 15 | SEQ ID NO: 52<br>SEQ ID NO: 58 | 20 | 58%<br>(45) |
| SEQ ID NO: 79<br>SEQ ID NO: 86 | SEQ ID NO: 40<br>SEQ ID NO: 15 | SEQ ID NO: 52<br>SEQ ID NO: 58 | 20 | 81%<br>(80) |
| SEQ ID NO: 83<br>SEQ ID NO: 86 | SEQ ID NO: 40<br>SEQ ID NO: 15 | SEQ ID NO: 52<br>SEQ ID NO: 58 | 20 | 74%<br>(77) |

The results presented in Table 7 confirmed that certain combinations of capture oligonucleotides, amplification primers and detection probes gave results that were substantially better than others. For example, the promoter-primer containing the HBV-complementary sequence of SEQ ID NO:23 (i.e., SEQ ID NO:40) and opposite strand primer of SEQ ID NO:15 were capable of producing positive results in 100% of amplification reactions containing only 20 copies of the HBV template. These primers represent a particularly preferred combination for amplifying HBV nucleic acids. Similarly, the above-described probes of SEQ ID NO:54, and the combination of the probes of SEQ ID NO:50 and SEQ ID NO:57 were capable of detecting the HBV amplicons in a highly efficient manner. Probes having these sequences, or probes having sequences complementary thereto, are preferred for detecting HBV nucleic acids.

The results presented in Table 7 further showed that certain combinations of capture oligonucleotides, amplification primers and detection probes worked synergistically in the multiplex amplification system. For example, the results shown for the trial conducted using capture oligonucleotides of SEQ ID NO:74 and SEQ ID NO:86, the amplification primer of SEQ ID NO:15 and the promoter-primer containing the HEY-complementary sequence of SEQ ID NO:23 (i.e., SEQ ID NO:40), together with the probes of SEQ ID NO:50 and SEQ ID NO:57 using 20 copies of the HBV template nucleic acid demonstrated that each of these primers and probes was capable of amplifying and detecting HBV template nucleic acids in 100% of the valid runs. When the same primers and probes were used in combination with only one of the capture oligonucleotides identified by SEQ ID NO:71 and SEQ ID NO:80 in reactions containing 20 copies of the HBV template nucleic acid, positive results were achieved in only about 30% of the valid runs. However, when the capture oligonucleotides that included the sequences of SEQ ID NO:71 and SEQ ID NO:80 were used in combination with each other, with each oligonucleotide being present in half of the total amount used in the trials having only a single capture oligonucleotide, dramatically higher results approaching 100% were achieved. This demonstrated how certain combinations of the assay reagents gave unexpectedly good results, even at very low levels of input target.

Example 4 describes a procedure that used a particular set of the invented oligonucleotides to illustrate how the different amplification assays described herein were characterized by different sensitivity ranges. The findings from this procedure established that 100% positive HBV detection results could be obtained in an amplified assay when the level of template used in the amplification reaction exceeded a certain threshold value. As will be apparent from comparing the below-presented results with those from the other Examples herein, this threshold value depended on the particular combination of oligonucleotides used in the amplification reaction. Notably, the assay described in this Example detected HBV genotypes A-G, even when the probe of SEQ ID NO:57 was the only probe used in the detection step.

EXAMPLE 4

Detection of HBV Nucleic Acids

Nucleic acid amplification reactions were conducted essentially as described in the preceding Examples, except that primers necessary for amplifying HIV-1 and HCV sequences were omitted. Capture oligonucleotides used in the procedure included the HBV-complementary sequences of SEQ ID NO:71 and SEQ ID NO:80. Amplification primers included the sequences of SEQ ID NO:22 and SEQ ID NO:23, each of these sequences having a T7 promoter sequence appended at its 5'-end. The complete sequences of the promoter primers were given by SEQ ID NO:39, and SEQ ID NO:40. Opposite strand primers had sequences given by SEQ ID NO:15 and SEQ ID NO:11. Acridinium ester-labeled probes used in the procedure had sequences given by SEQ ID NO:50 and SEQ ID NO:57, as described above. 500 μl aliquots of virion-containing plasma were subjected to the above-described detergent lysis and target capture procedure. Amplification reactions were carried out, and the amplification products detected, also using the above-described procedures. Virion concentrations of samples processed in this procedure ranged from 0-100 EU/ml, where 1 EU corresponds to approximately 3 copies of the HBV genome. Positive detection of HBV target sequences in the amplification reactions was assessed essentially as described in the preceding Examples.

The results presented in Table 8 indicated that 100% of the reactions conducted using 300 copies of the HBV template gave positive results, and that 95% positively was achieved at some level between 75 and 150 copies per reaction. Significantly, substantially similar results were obtained when the amplification reactions were conducted in the absence of the primer identified as SEQ ID NO:15. Thus, a preferred combination of primers for amplifying HBV nucleic acids has HBV-complementary sequences given by SEQ ID NO:22, SEQ ID NO:23, and SEQ ID NO:11, with the primer of SEQ ID NO:15 being optional. A preferred probe composition for detecting HBV amplification products includes the probe of SEQ ID NO:57, with further inclusion of the probe of SEQ ID NO:50 being optional.

TABLE 8

Sensitivity Testing Establishes a Range for the Level of Templates Detected in an Assay

| HBV Genotype A (copies) | % Positive |
| --- | --- |
| 300 | 100.0 |
| 150 | 99.0 |
| 75 | 91.7 |
| 36 | 71.0 |
| 18 | 43.9 |
| 0 | 0.3 |

The results in Table 8 further confirmed that even primer combinations listed in Tables 6 and 7 that did not result in high levels of HBV detection at the specified level of input template were capable of identifying HBV-containing samples at levels approaching 100% detectability when the amount of template was sufficiently high. Based on these findings, it was concluded that primer combinations that gave at least some measure of HBV detection when the amount of input template ranged from 6-20 copies per reaction were deemed useful in procedures for amplifying HBV nucleic acids in vitro. While it may be desirable in some circumstances to use combinations of primers that result in highly sensitive assays, other circumstances may benefit from using assays characterized by somewhat lower sensitivities. Thus, any of the primer combinations disclosed herein that gave measurable results in Tables 6 and 7 can be used as components of HBV nucleic acid amplification assays, and fall within the scope of the invention.

Example 5 illustrates how the qualitative assay from the preceding Example can be adapted to a quantitative format. Spike recovery of three HBV genotype A positive controls provided a quantitative assessment of assay performance. The assay relied on the use of a pseudo target in accordance with U.S. Pat. No. 6,294,338, the disclosure of which is hereby incorporated by reference. Although either RNA or DNA pseudo targets can be used in quantitative assays, the following procedure was conducted using an RNA pseudo target.

EXAMPLE 5

Quantitative Assay for Measuring HBV

The oligonucleotide components used in the quantitative assay were identical to the reagents used in the preceding Example, except that the probe of SEQ ID NO:50 was omitted. Each amplification reaction additionally included an RNA pseudo target having the sequence of SEQ ID NO:97 in an amount corresponding to about $80 \times 10^6$ copies. HBV genotype A calibrators having concentrations ranging from 380-12,000 HBV IU/ml were used as the source of HBV templates in separate reactions to produce standard curves. TMA reactions were conducted for a period of 60 minutes, substantially as described above. Detection of amplified HBV sequences was carried out using a standard homogeneous protection assay that employed the above-described probe of SEQ ID NO:57 as a combination of acridinium ester-labeled and unlabeled species in a ratio of 1:6.25. Use of the unlabeled probe allowed all chemiluminescent signals to fall within the reliable response range of the luminometer that measured specifically hybridized probe. Pseudo target amplicons were not detected by the probe that was used in this procedure.

Figure 2:
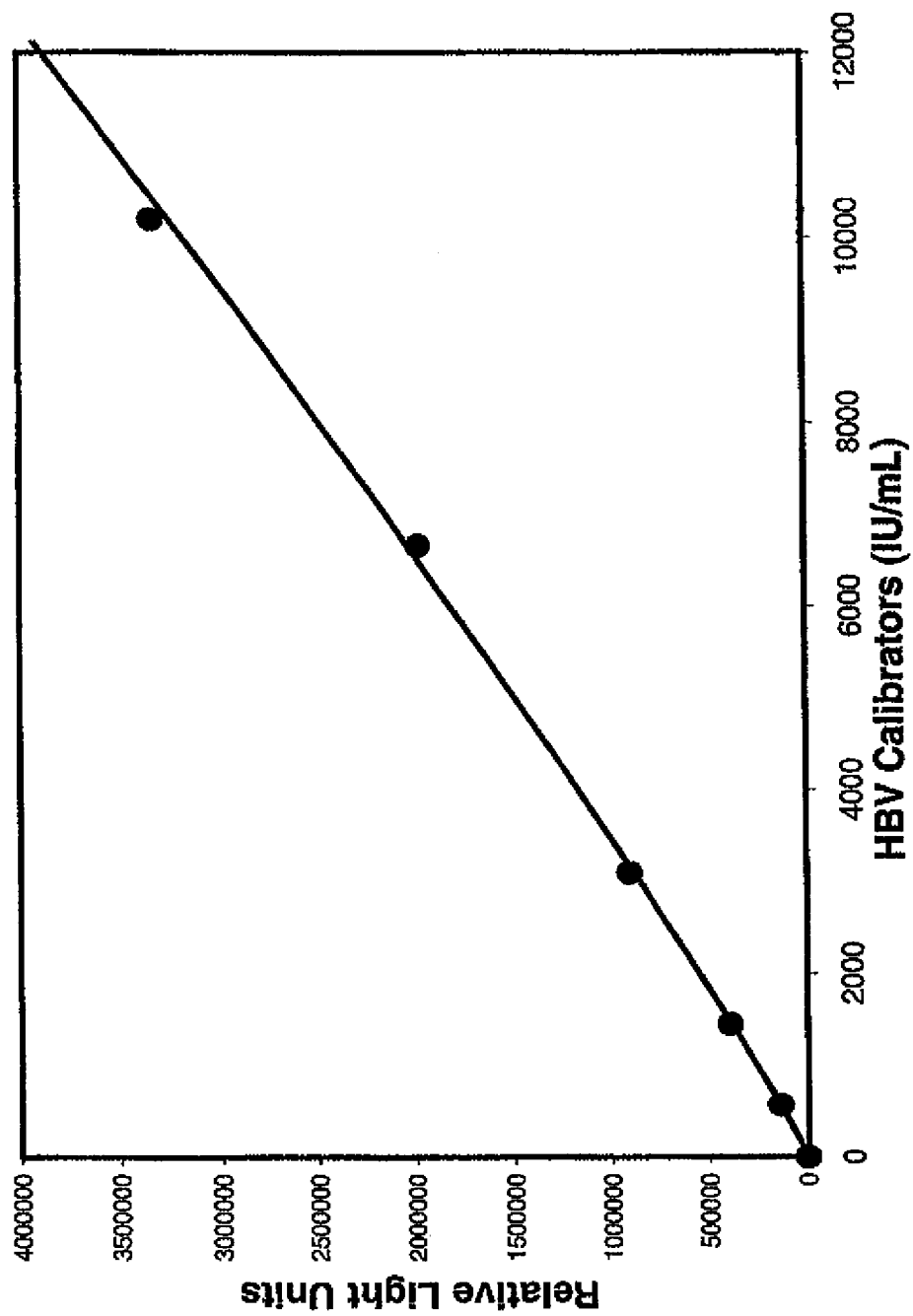
FIG. 2 is a line graph showing a quantitative HBV calibrator curve that emphasizes the linear relationship between input template amount and hybridization signal strength over a broad range of calibrator amounts.

The results presented in FIG. 2 showed how the quantitative assay gave a substantially linear relationship between the amount of input HBV template and the hybridization signal strength over a broad range of HBV concentrations that extended from 0-12,000 IU/ml. The lower limit of detection in this assay was about 1 IU/ml, or between 1 and 2 copies of the HBV nucleic acid in a single amplification reaction. Thus, this quantitative assay was highly sensitive and had the ability to measure HBV concentrations, or template copy numbers, over a very broad range in a precise manner.

Example 6 describes a procedure which demonstrated how the use of a second promoter-primer in a TMA reaction could positively influence detectability of different HBV genotypes. In addition to the HBV-specific target capture oligonucleotides, amplification primer, and probes described in this procedure, the reactions also included the above-described oligonucleotides specific for the HIV-1 and HCV analytes. The HIV-1 and HCV oligonucleotides did not substantially contribute to detection of the HBV analyte.

EXAMPLE 6

Improved Detectability of HBV Genotypes

Genotyped HBV-containing samples (genotypes A-F) were obtained from Millenium Biotech, Inc., (Ft. Lauderdale, Fla.) or Boston Biomedica (West Bridgewater, Mass.). Quantitation values were supplied by the vendor's certificate of analysis and were based on results from the AMPLICOR HBV MONITOR assay (Roche Diagnostics Corp.). In the absence of plasma samples containing HBV genotype G virions, a single-stranded M13 clone that included HBV genotype G nucleic acid sequences corresponding to all of the relevant oligonucleotides, except for capture oligonucleotide that included SEQ ID NO:87, served as the template for procedures that amplified sequences of this genotype. Panel members were made by serial dilution of patient plasma samples using negative human plasma. 400 µl of target capture reagent (HEPES-buffered detergent solution containing the above-described capture oligonucleotides having the HBV-complementary sequences of SEQ ID NO:73, SEQ ID NO:80 and SEQ ID NO:87, together with magnetic particles) containing internal control and 500 µl of each specimen or panel member were pipetted manually into Ten Tube Units (TTUs). After addition of the target capture reagent and specimen, the TTUs were vortexed and incubated in a 60° C. water bath for 20 minutes, followed by room temperature incubation (15-30° C.) for 14-20 minutes. The rack of TTUs was then placed in a magnetic separation bay for 9-20 minutes. Liquid was aspirated from each tube and then replaced with 1 ml of wash solution. The rack was vortexed and again placed on the separation bay for 4-10 minutes. The wash solution was aspirated from each tube and wash and separation steps were repeated, finishing with a final aspiration. After the final aspiration step, 75 μl of amplification reagent (including one of two different primer formulations, dNTPs, NTPs and cofactors in Tris-buffered solution) was added to each tube. Primer formulation A included a promoter-primer having the HBV-complementary sequence of SEQ ID NO:23 (i.e., SEQ ID NO:40), as well as opposite strand primers identified by SEQ ID NO:15 and SEQ ID NO:11. Primer formulation B additionally included a promoter-primer having the HBV-complementary sequence of SEQ ID NO:26 (i.e., SEQ ID NO:43). Each mixture was overlaid with 200 μl of inert oil to prevent evaporation during the amplification step, and the rack of TTUs vortexed to resuspend the microparticles. Prior to the addition of 25 μl of enzyme reagent, (MMLV reverse transcriptase and T7 RNA polymerase in HEPES/Tris-buffered solution), the rack was incubated in a water bath at 60° C. for 10 minutes, followed by equilibration at 41.5° C. for 9-20 minutes. Immediately after adding the enzyme reagent, the rack of TTUs was removed from the incubator and shaken to mix. The rack was then incubated in the water bath at 41.5° C. for 60 minutes. After amplification, 100 μl of probe reagent, which included the above-described acridinium ester labeled probes of SEQ ID NO:54 in succinate buffered detergent solution, was added to each tube, vortexed, and incubated in a water bath at 60° C. for 15 minutes. Following the completion of the probe hybridization step, 250 μl of selection reagent (borate-buffered solution with surfactant) was added to each tube. Tubes were vortexed, and then incubated at for 10 minutes. After removal from the 60° C. water bath, the rack of TTUs was cooled in a water bath at 19-27° C. for 10-75 minutes and then placed in a LEADER HC+ luminometer (Gen-Probe Incorporated; San Diego, Calif.) configured for automatic injection of 200 μl of a solution of 0.1% hydrogen peroxide and 1 mM nitric acid; and 200 μl of 1 N NaOH. To determine reactivity, the resulting chemiluminescence was compared to a cutoff value generated from the positive and negative calibrators that had been included in each 100 tube run. To monitor assay performance for each specimen reaction, an internal control contained in the target capture reagent was added to each test specimen. The internal control consisted of an in vitro synthesized transcript containing a portion of HIV-1 and a unique sequence targeted by the internal control probe. The internal control signal in each reaction was discriminated from the HBV signal by the differential kinetics of light emission from probes with different labels. The internal control amplification product was detected using a probe with rapid emission of light while the amplicon specific to HBV was detected using probes with slower kinetics of light emission. Software receiving inputs from the luminometer differentiated between the two signals. Results of these procedures are shown in Table 9.

TABLE 9

Improved Detectability of HBV Genotypes

| HBV Genotype | Copies/ Reaction | Primer Formulation A (% Positive) | Primer Formulation B (% Positive) |
|---|---|---|---|
| A | 50 | 100 | 100 |
|   | 15 | 100 | 100 |
| A | 50 | 100 | 100 |
|   | 15 | 100 | 100 |
| B | 50 | 85 | 100 |
|   | 15 | 60 | 80 |
| C | 50 | 95 | 100 |
|   | 15 | 83 | 100 |
| D | 50 | 95 | 100 |
|   | 15 | 60 | 95 |
| E | 50 | 100 | 100 |
|   | 15 | 70 | 100 |
| F | 50 | 100 | 100 |
|   | 15 | 100 | 100 |
| G | 50 | 0 | 100 |
|   | 15 | 0 | 85 |

As indicated by the results presented in Table 9, the primer formulation that included two promoter-primers advantageously detected HBV in 100% of the samples containing each of the different HBV genotypes at the 50 copy level. This was not true when the HBV genotype B, C, D, E or G templates were used at the same template copy level in the amplification reactions that included only one promoter-primer. The negative results obtained for TMA reactions conducted using a single promoter-primer and the cloned HBV genotype G template were artifacts due to the use of a template that was entirely single-stranded. Separate testing performed using HBV genotype G virions as the source of templates, and primer formulation B as the source of primers, gave 100% detectability at both 15 and 50 copies/reaction. When it is desirable to amplify the nucleic acids of HBV genotypes A-G in a highly sensitive manner, it is preferred to use two first strand primers and at least one second strand primer in the reaction. In a particular instance, when it is desirable to amplify the nucleic acids of HBV genotypes A-G in a highly sensitive TMA reaction, it is preferred to use two promoter primers and at least one non-promoter primer in the reaction. Of course, in vitro nucleic acid amplification reactions based on thermal cycling protocols, or procedures that involve a step for physically separating newly synthesized strands of nucleic acid from their templates, can be conducted using only one upstream primer and one downstream primer.

The following Examples present evidence showing that combinations of the oligonucleotides disclosed herein could be used in multiplex reactions that were also capable of detecting each of HIV-1 and HCV nucleic acids in a highly sensitive manner.

Example 7 describes a procedure wherein HIV-1 target nucleic acids were detected using the oligonucleotides specific for HIV-1 and the amplification and detection protocols disclosed herein.

EXAMPLE 7

Detection of HIV-1 in a Multiplex Amplification Reaction

Samples of the HIV-1 WHO Standard, Subtype B (97/656) were diluted into negative human plasma to give viral titers ranging from 0-300 IU/ml. 500 μA samples of this dilution panel were then subjected to specimen processing, target capture, amplification and detection according to the procedures described under Example 2 using the HIV-1 specific oligonucleotides of SEQ ID NOs:100-114 together with the HCV specific oligonucleotides of SEQ ID NOs:115-125 and HBV specific oligonucleotides. The HIV-1 specific capture oligonucleotides had the sequences of SEQ ID NOs:113-114.

The HIV-1 specific promoter-primers of SEQ ID NOs:100-101 had the essential HIV-complementary sequences of SEQ ID NOs:98-99 respectively appended to an upstream promoter sequence. Opposite strand primers had the sequences of SEQ ID NOs:102-103. Probes had the sequences of SEQ ID NOs:106-108. The HCV specific capture oligonucleotides had the sequences of SEQ ID NOs:124-125. The HCV specific promoter-primer of SEQ ID NO:116 had the essential HCV-complementary sequence of SEQ ID NO:115 appended to an upstream promoter sequence. Opposite strand primers had the sequences of SEQ ID NOs:117-118. Probes had the sequences of SEQ ID NOs:120 and 122. HBV specific oligonucleotides in this procedure included the capture oligonucleotides having the HBV-complementary sequences of SEQ ID NO:73, SEQ ID NO:80 and SEQ ID NO:87; amplification primers of SEQ ID NO:40, SEQ ID NO:43, SEQ ID NO:15 and SEQ ID NO:11; and the above-described hybridization detection probes of SEQ ID NO:54. The HBV specific promoter-primers of SEQ ID NO:40 and 43 respectively had the essential HBV-complementary sequences of SEQ ID NO:23 and 26 appended to an upstream promoter sequence. Twenty replicates were carried out, and the 95% detection probability at the 95% confidence interval determined. Results of the procedure are presented in Table 10.

TABLE 10

Detection of HIV-1 Nucleic Acids in Multiplex Amplification Reaction

| Titer (IU/ml) | % Positive | 95% Detection Probability |
|---|---|---|
| 300 | 100 | 13.0 |
| 100 | 100 | (10.1 to 19.5) |
| 33.3 | 100 | |
| 11.1 | 84 | |
| 3.7 | 53 | |
| 1.23 | 21 | |
| 0 | 0 | |

The results shown in Table 10 clearly indicated that HIV-1 nucleic acids were detected in the multiplex reaction that was also capable of detecting HCV and HBV nucleic acids. Moreover, additional testing indicated that HIV-1 type/group detectability in this assay included A, B, C, D, E, F, G, Group N and Group O at levels approaching 100% positively when reactions contained 100 copies/ml or more of HIV-1. As indicated hereinabove, the collection of HIV-1 specific oligonucleotides used in this procedure can be used in stand-alone assays for detecting HIV-1, or in combination with the oligonucleotides specific for HCV, or alternatively HBV, to create duplex assays.

Example 8 describes a procedure wherein HCV target nucleic acids were detected using the oligonucleotides specific for HCV and the amplification and detection protocols disclosed herein.

EXAMPLE 8

Detection of HCV in a Multiplex Amplification Reaction

Samples of the HCV WHO Standard, genotype 1 (96/790) were diluted into negative human plasma to give viral titers ranging from 0-100 IU/ml. 500 µl samples of this dilution panel were then subjected to specimen processing, target capture, amplification and detection using the oligonucleotides and procedures described under the previous Example. Twenty replicates were carried out, and the 95% detection probability at the 95% confidence interval determined. Results of the procedure are presented in Table 11.

TABLE 11

Detection of HCV Nucleic Acids in Multiplex Amplification Reaction

| Titer (IU/ml) | % Positive | 95% Detection Probability |
|---|---|---|
| 100 | 100 | 1.6 |
| 33.3 | 100 | (1.2 to 2.3) |
| 11.1 | 100 | |
| 3.7 | 100 | |
| 1.23 | 80 | |
| 0.41 | 47 | |
| 0 | 0 | |

The results shown in Table 11 clearly indicated that HCV nucleic acids were detected in the multiplex reaction that was also capable of detecting HIV-1 and HBV nucleic acids. Moreover, additional testing indicated that HCV genotypes 1, 1b, 2b, 2a/c, 3, 3e, 4, 4a, 4b/c, 5, 5a, 6, 6a were all detected with 100% positively when reactions contained 100 copies/ml or more of HCV. As indicated hereinabove, the collection of HCV specific oligonucleotides used in this procedure can be used in stand-alone assays for detecting HCV, or in combination with the oligonucleotides specific for HIV, or alternatively HBV, to create duplex assays.

Example 9 describes a procedure wherein HBV target nucleic acids were detected using the oligonucleotides specific for HBV and the amplification and detection protocols disclosed herein. The experimental results presented below quantitatively illustrate the sensitivity of this assay.

EXAMPLE 9

Detection of HBV in a Multiplex Amplification Reaction

Samples of the HBV WHO Standard, genotype A (97/746) were diluted into negative human plasma to give viral titers ranging from 0-45 IU/ml. 500 µl samples of this dilution panel were then subjected to specimen processing, target capture, amplification and detection using the oligonucleotides and procedures described under Example 7. Eighty replicates were carried out, and the 95% detection probability at the 95% confidence interval determined. Results of the procedure are presented in Table 12.

TABLE 12

Detection of HBV Nucleic Acids in Multiplex Amplification Reaction

| Titer (IU/ml) | % Positive | 95% Detection Probability |
|---|---|---|
| 45 | 100 | 5.7 |
| 15 | 100 | (4.8 to 7) |
| 5 | 90 | |
| 1.67 | 45 | |
| 0.56 | 15 | |
| 0 | 0 | |

The results shown in Table 12 clearly indicated that HBV nucleic acids were detected in the multiplex reaction that was also capable of detecting HIV-1 and HCV nucleic acids. Moreover, the nucleic acids of HBV genotypes A-G were all detectable in this assay. As indicated hereinabove, the collection of HBV specific oligonucleotides used in this procedure can be used in stand-alone assays for detecting HBV, or in combination with the oligonucleotides specific for HIV, or alternatively HCV, to create duplex assays.

To further illustrate the versatility of the above-described analyte detection systems, amplicon production was monitored as a function of time in "real-time" amplification procedures. Amplicon-specific molecular beacons that were included in the amplification reactions provided a means for continuous monitoring of amplicon synthesis. Fluorescent emissions that increased with time indicated the production of amplicons that hybridized to the molecular beacon and caused a detectable transition to the "open" conformation of the probe.

Molecular beacons comprise nucleic acid molecules having a target-complementary loop sequence, an affinity pair (or nucleic acid "arms") that interact to form a "stem" structure by complementary base pairing in the absence of a target (i.e., the "closed" conformation), and a paired set of labels that interact when the probe is in the closed conformation. Hybridization of the target nucleic acid and the target-complementary sequence of the probe causes the members of the affinity pair to separate, thereby shifting the probe to the open confirmation. This shift is detectable by virtue of reduced interaction between the members of label pair, which may be, for example, a fluorophore and a quencher. Molecular beacons are fully described in U.S. Pat. No. 5,925,517, the disclosure of this patent document being incorporated by reference herein.

Commercially available software was used to analyze time-dependent results obtained using molecular beacons that were specific for HBV, HIV-1 or HCV amplicons. Results from these analyses indicated a strong linear relationship between the number of target copies included in an amplification reaction and the time at which the fluorescent signal exceeded a background threshold (i.e., "time-of-emergence" above background). As confirmed by the results presented below, these procedures were useful for quantifying analyte target amounts over a very broad range. More particularly, when known amounts of analyte polynucleotides are used as calibration standards, it is possible to determine the amount of analyte present in a test sample by comparing the measured time-of-emergence with the standard plot.

The fact that the amplification reaction used in the below-described procedures operated at constant temperature and without interruption for a separate detection step, so that amplification and detection took place simultaneously, imposed strict requirements on the molecular beacons. More specifically, success in the procedure required that the molecular beacon bind amplicon without inhibiting subsequent use of the amplicon as a template in the exponential amplification mechanism. Indeed, the finding that an amplification reaction could proceed efficiently in the presence of a molecular beacon indicated that interaction of the probe with its target did not irreversibly inhibit or poison the amplification reaction.

Example 10 describes procedures wherein molecular beacon probes, each labeled with an interactive fluorophore/quencher pair, were used for monitoring time-dependent amplicon production in TMA reactions. Although the molecular beacons described in this Example hybridized to only one strand of the amplified nucleic acid product, complementary probe sequences also would be expected to hybridize to the opposite nucleic acid strand, and so fall within the scope of the invention.

EXAMPLE 10

Real-Time Monitoring of Amplicon Production

Molecular beacons having binding specificity for HBV, HIV-1 or HCV amplicons were synthesized by standard solid-phase phosphite triester chemistry using 3' quencher-linked controlled pore glass (CPG) and 5' fluorophore-labeled phosphoramidite on a Perkin-Elmer (Foster City, Calif.) EXPEDITE model 8909 automated synthesizer. Fluorophores used for constructing the molecular beacons included fluorescein, ROX and CY5 dyes. BLACK HOLE QUENCHER 2 (Biosearch Technologies, Inc.; Novato, Calif.) and DABCYL were used as quenchers. All of the molecular beacons were constructed using 2'-methoxy nucleotide analogs. The CPG and phosphoramidite reagents were purchased from Glen Research Corporation (Sterling, Va.). Following synthesis, the probes were deprotected and cleaved from the solid support matrix by treatment with concentrated ammonium hydroxide (30%) for two hours at Wt. Next, the probes were purified using polyacrylamide gel electrophoresis followed by HPLC using standard procedures that will be familiar to those having an ordinary level of skill in the art.

The HBV, HIV-1 and HCV nucleic acid targets used in the procedure were artificial or synthetic targets of known concentration. The HBV target was a single-stranded M13 clone containing a portion of the HEY genome that included sequences corresponding to, or complementary to each of the primers. The HIV-1 target was a synthetic transcript. The HCV target was an ARMORED RNA (Ambion, Inc.; Austin, Tex.) that included HCV genomic sequences. ARMORED RNA® technology is used for producing ribonuclease-resistant RNA controls and standards by assembling specific RNA sequences and viral coat proteins into pseudo-viral particles. Molecular beacons were used at a level of about 1.5 pmoles/reaction. Reactions for amplifying HBV contained $5 \times 10^2 - 5 \times 10^9$ template copies/reaction. Reactions for amplifying HIV-1 contained $5 \times 10^1 - 5 \times 10^6$ template copies/reaction. Reactions for amplifying HCV contained $5 - 5 \times 10^8$ template copies/reaction.

Tubes containing 15 µl of a buffered solution that included salts and reagents essentially as described under Example 2, a target polynucleotide, and a molecular beacon were first overlaid with 15 µl of inert oil to prevent evaporation. The tubes were then incubated in a dry heat block for 10 minutes at 60° C. to facilitate primer annealing. Primers for amplifying the HBV target had the target-complementary sequences of SEQ ID NO:23, SEQ ID NO:26, SEQ ID NO:15 and SEQ ID NO:11. Primers for amplifying the HIV-1 target had the target-complementary sequences of SEQ ID NO:99, SEQ ID NO:100, SEQ ID NO:103 and SEQ ID NO:102. Primers for amplifying the HCV target had the target-complementary sequences of SEQ ID NO:115, SEQ ID NO:117 and SEQ ID NO:118. Notably, amplification reactions used for testing the HBV-specific molecular beacons included all of the primers for amplifying all three targets. Amplification reactions used for testing the HIV-1 and HCV-specific molecular beacons included all of the primers for amplifying both of these targets, but not primers for amplifying the HBV target. Of course, it is intended that any of the below-described molecular beacons could be used in amplification reactions that include any combination of primers. Following the 60° C. incubation step, tubes were transferred to a 42° C. heat block and then incubated for 10 minutes. Five microliter aliquots of an enzyme reagent that included both MMLV reverse transcriptase and T7 RNA polymerase enzymes were added to each of the tubes using a multichannel pipettor. Tubes were vortexed briefly and then transferred to a ROTORGENE-2000 (Corbett Research; Sydney, Australia) rotor that had been pre-warmed to 42° C. Amplification reactions were carried out at 42° C., fluorescence readings were taken every 30 seconds, and the results analyzed in real-time using standard software that was bundled with the ROTORGENE-2000 instrument.

Figure 3:
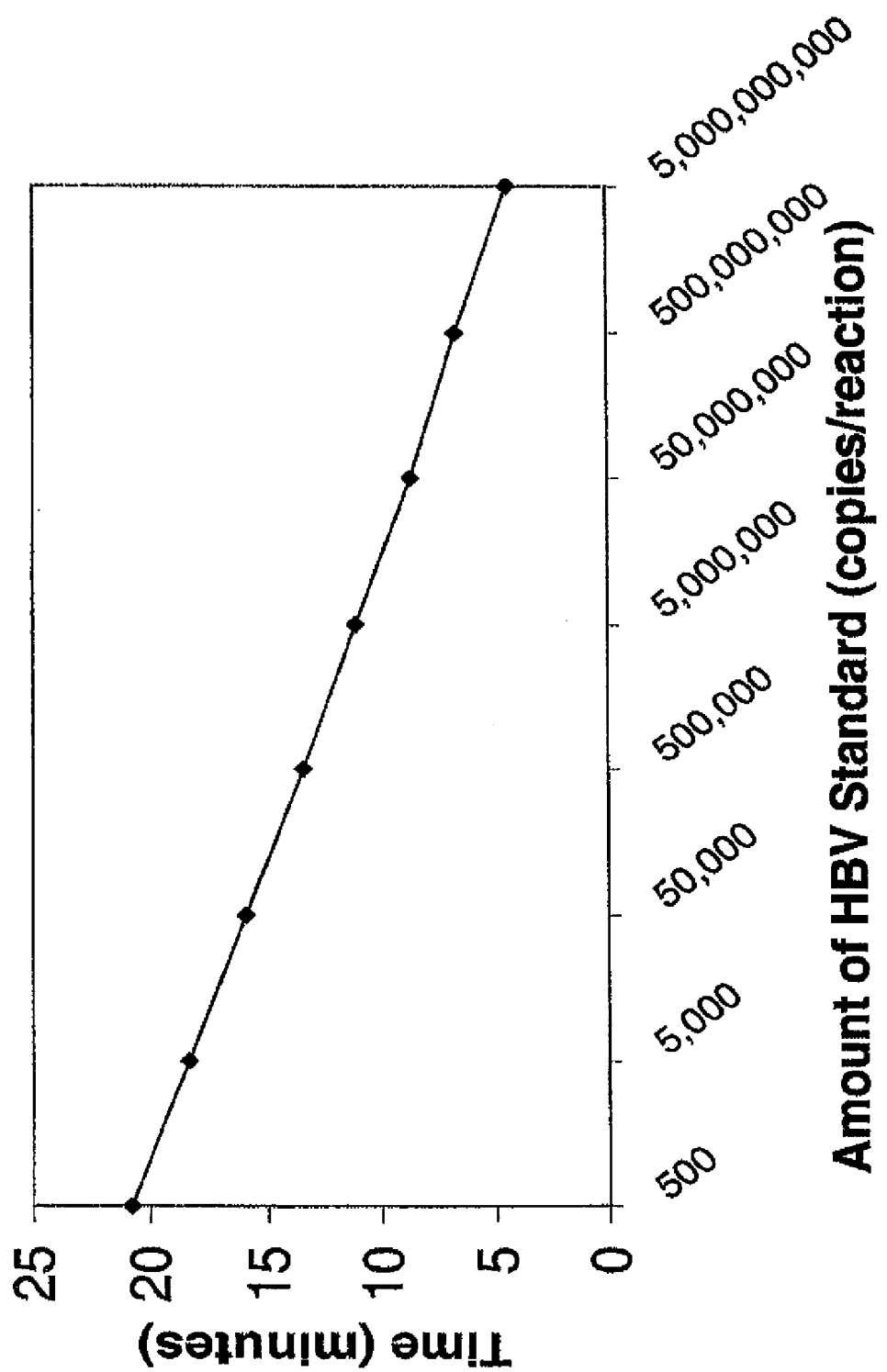
FIG. 3 is a line graph relating the amount of HBV standard input into a real-time nucleic acid amplification reaction (x-axis) and the time-of-emergence of the measured fluorescent signal above a background threshold (y-axis).

Table 13 presents the target-complementary loop sequences of HBV-specific molecular beacons that were used during the development of the invention. Each of the molecular beacons included an appended 5' CCGAG arm sequence, and an appended 3' CUCGG arm sequence. Each probe included a CY5 fluorophore at its 5'-end, and a BLACK HOLE QUENCHER 2 moiety at its 3'-end. All of the HBV-specific molecular beacons had target-complementary loop sequences that were 12-20 nucleotides in length and included 12-20 contiguous nucleotides contained within the sequence AAGAAGATGAGGCATAGCAGCAGGATGAAGAGG-AA SEQ ID NO:126, allowing for the presence of nucleotide analogs and RNA and DNA equivalents.

time assay format. For example, reactions that included the highly preferred molecular beacon having the target-complementary loop sequence of SEQ ID NO:127 gave rapid detection of high target numbers and a strong linear relationship between the fluorescent signal and target amount on a logarithmic plot over the full range of input target levels tested (see FIG. 3). Coefficients of variation (CVs) for the time-of-emergence readings obtained using this probe were 3.2% or less, thereby indicating very high levels of precision among the data points. Reactions that included the molecular beacon having the target-complementary loop sequence of SEQ ID NO:133 exhibited different response characteristics that were somewhat less linear over the range of target input levels tested due to the probe response at low target levels. This latter probe will be particularly useful for detecting and quantifying HBV target amounts greater than 5,000 copies of HBV.

TABLE 14

Measured Time-of-Emergence for Different Molecular Beacons

Time-of-Emergence for Different Molecular Beacons (minutes)

| HBV Target copies/rxn | SEQ ID NO: 127 | SEQ ID NO: 128 | SEQ ID NO: 129 | SEQ ID NO: 130 | SEQ ID NO: 131 | SEQ ID NO: 132 | SEQ ID NO: 133 |
|---|---|---|---|---|---|---|---|
| $5 \times 10^9$ | 4.4 | NT | NT | 3.3 | 8.9 | NT | NT |
| $5 \times 10^8$ | 6.7 | NT | NT | 5.4** | 14.9 | NT | NT |
| $5 \times 10^7$ | 8.7 | NT | NT | 6.2* | 23.4 | 10.1 | 10.0 |
| $5 \times 10^6$ | 11.1 | NT | NT | NT | NT | 12.3 | 12.2 |
| $5 \times 10^5$ | 13.4 | 16.3 | 20.9 | NT | NT | 14.5 | 13.9 |
| $5 \times 10^4$ | 15.9 | 18.6 | 33.5* | NT | NT | 17.2 | 17.6 |
| $5 \times 10^3$ | 18.3 | 29.7* | ND | NT | NT | 21.9* | 21.5* |
| $5 \times 10^2$ | 20.8** | NT | NT | NT | NT | ND | 49.7* |

"NT" = not tested
"ND" = not detected
*= only one out of three replicates reactive
**= only two out of three replicates reactive

TABLE 13

Target-Complementary Loop Sequences of HBV-Specific Molecular Beacons

| Sequence (5' to 3') | Identifier |
|---|---|
| GAAGAUGAGGCAUAGCAG | SEQ ID NO: 127 |
| AAGAAGAUGAGGCAUAGCAG | SEQ ID NO: 128 |
| CAGCAGGAUGAAGAGGAA | SEQ ID NO: 129 |
| CAGGAUGAAGAGGA | SEQ ID NO: 130 |
| AAGAAGAUGAGG | SEQ ID NO: 131 |
| GAAGAUGAGGCAUAGC | SEQ ID NO: 132 |
| GAAGAUGAGGCAUA | SEQ ID NO: 133 |

The results presented in Table 14 confirmed that amplification reactions which included one of the HBV-specific molecular beacons desirably produced a fluorescent signal that increased with time. All results were based on reactions that were conducted in triplicate. Significantly, the different molecular beacons behaved somewhat differently in the real- Table 15 presents the target-complementary loop sequences of HIV-specific molecular beacons that were used during the development of the invention. The molecular beacon having the target-complementary loop sequence of SEQ ID NO:134 included an appended 5' CCGAG arm sequence, and an appended 3' CUCGG arm sequence. This probe included a ROX fluorophore at its 5'-end, and a BLACK HOLE QUENCHER 2 quencher moiety at its 3'-end. A related molecular beacon had an identical target-complementary loop sequence, but had the overall sequence 5'-CCGAGAGGGUACAGUGCAGGGGUCUCGG-3' (SEQ ID NO:135). When compared with the above-described HIV-specific molecular beacon, the arms of this probe each included a single additional nucleotide immediately adjacent to the target-complementary loop sequence of the probe. This probe also included a fluorescein fluorophore (instead of ROX) at its 5'-end, and a DABCYL quencher moiety (instead of the BLACK HOLE 2 QUENCHER 2) at its 3'-end. The molecular beacon having the target-complementary loop sequence of SEQ ID NO:136 included an appended 5' CCGAGA arm sequence, and an appended 3' UCUCGG arm sequence. This probe also included a fluorescein fluorophore at its 5'-end, and DABCYL quencher moiety at its 3'-end. The molecular beacons used in these procedures had target-complementary loop sequences that were 16-17 nucleotides in length, and included 16-17 contiguous nucleotides contained within the sequence GGGGTACAGTGCAGGGG (SEQ ID NO:137), allowing for the presence of nucleotide analogs and RNA and DNA equivalents.

TABLE 15

Target-Complementary Loop Sequences of HIV-Specific Molecular Beacons

| Sequence (5' to 3') | Identifier |
|---|---|
| GGGUACAGUGCAGGGG | SEQ ID NO: 134 |
| AGGGGUACAGUGCAGGGGU | SEQ ID NO: 136 |

The results presented in Table 16 confirmed that amplification reactions which included one of the HIV-specific molecular beacons desirably produced a fluorescent signal that increased with time. The molecular beacon that included the target-complementary loop sequence of SEQ ID NO:134 allowed rapid detection of low target levels. Reactions that included this probe were conducted in triplicate and exhibited a strong linear relationship between input target level and fluorescent signal with at least four logs of useful dynamic range extending from $5 \times 10^1 - 5 \times 10^5$ copies/reaction of the HIV-1 target. Although the results are not presented in the table, additional testing showed that the dynamic range of reactions that included this molecular beacon extended up to $5 \times 10^7$ or $5 \times 10^8$ copies/reaction of the HIV-1 target. The molecular beacon having the sequence of SEQ ID NO:135 exhibited a biphasic plot on a logarithmic graph of input target amount against time-of-emergence. These reactions, which were conducted in replicates of five, exhibited a strong linear relationship between input target amount and time-of-emergence in the range of $5 \times 10^3 - 5 \times 10^6$, and a somewhat weaker linear relationship in the range of $5 \times 10^1 - 5 \times 10^3$ copies/reaction of the HIV-1 target. This molecular beacon is particularly useful for quantifying the higher range of target amounts in real-time assays, but exhibited a useful dynamic range of at least five logs that covered the range extending from $5 \times 10^1 - 5 \times 10^6$ copies/reaction of the HIV-1 template. Reactions that included the molecular beacon having the target-complementary loop sequence of SEQ ID NO:136 were conducted in triplicate and exhibited a strong linear relationship between input target level and fluorescent signal with at least three logs of useful dynamic range that extended from $5 \times 10^2 - 5 \times 10^5$ copies/reaction of the HIV-1 target. Interestingly, amplification reactions that included this molecular beacon required slightly more time for detecting low target amounts when compared with reactions that included either of the other two HIV-specific molecular beacons.

TABLE 16

Measured Time-of-Emergence for Different Molecular Beacons

| HBV Target | Time-of-Emergence for Different Molecular Beacons (minutes) | | |
|---|---|---|---|
| (copies/rxn) | SEQ ID NO: 134 | SEQ ID NO: 135 | SEQ ID NO: 136 |
| $5 \times 10^6$ | NT | 4.0 | NT |
| $5 \times 10^5$ | 7.2 | 5.8 | 6.1 |
| $5 \times 10^4$ | 8.8 | 8.0 | 9.3 |
| $5 \times 10^3$ | 10.6 | 9.7 | 11.2 |
| $5 \times 10^2$ | 12.7 | 12.7 | 14.2 |
| $5 \times 10^1$ | 14.8 | 17.0 | ND |

"NT" = not tested
"ND" = not detected

Table 17 presents the target-complementary loop sequences of HCV-specific molecular beacons that were used during the development of the invention. The molecular beacon that included the target-complementary loop sequence of SEQ ID NO:138 included an appended 5' CGAGG arm sequence, and an appended 3' CCUCG arm sequence. This molecular beacon additionally included a CY5 fluorophore at its 5'-end, and a BLACK HOLE QUENCHER 2 moiety at its 3'-end. The molecular beacon that included the target-complementary loop sequence of SEQ ID NO:139 included an appended 5' CCGAG arm sequence, and an appended 3' CUCGG arm sequence. This molecular beacon was labeled with a fluorescein fluorophore at its 5'-end, and with a DABCYL moiety at its 3'-end. The molecular beacon that included the target-complementary loop sequence of SEQ ID NO:140 included an appended 5' CGGAC arm sequence, and an appended 3' GUCCG arm sequence. This molecular beacon was labeled at its 5'-end with a CY5 fluorophore, and at its 3'-end with a BLACK HOLE QUENCHER 2 moiety. The molecular beacons harboring the target-complementary loop sequences of the probes that included the target-complementary loop sequences of SEQ ID NO:138, SEQ ID NO:139 and SEQ ID NO:140 were tested in replicates of five, three and four, respectively. All of the molecular beacons used in these procedures had target-complementary loop sequences that were 10-14 nucleotides in length and included 10-14 contiguous nucleotides contained within the sequence TAGTAT-GAGTGTCGTGCAGCCTCCAGGAC-CCCCCCTCCCGGGAGAGCCATAGTGGTC TGCGGAACCGGTGAGTACACCGGAATTGC (SEQ ID NO:141), allowing for the presence of nucleotide analogs and RNA and DNA equivalents.

TABLE 17

Target-Complementary Loop Sequences of HCV-Specific Molecular Beacons

| Sequence (5' to 3') | Identifier |
|---|---|
| AACCGGUGAG | SEQ ID NO: 138 |
| UACACCGGAAUUGC | SEQ ID NO: 139 |
| UAGUAUGAGUGUC | SEQ ID NO: 140 |

The results presented in Table 18 confirmed that amplification reactions which included one of the HCV-specific molecular beacons desirably produced a fluorescent signal that increased with time. Reactions that included the molecular beacon having the target-complementary loop sequence of SEQ ID NO:138 exhibited a useful dynamic range of about six logs, with good results being achieved in the range of target amounts extending from $5 \times 10^1 - 5 \times 10^1$ copies/reaction of the HCV template. Reactions that included the molecular beacon having the target-complementary loop sequence of SEQ ID NO:139 exhibited a useful dynamic range of about seven logs, with good results being achieved in the range of about $5 \times 10^1 - 5 \times 10^8$ copies/reaction of the HCV template. Reactions that included the molecular beacon having the target-complementary loop sequence of SEQ ID NO:140 exhibited a useful dynamic range of about eight logs, with excellent results being achieved over the full range of about $5 - 5 \times 10^8$ copies/reaction of the HCV template.

TABLE 18

Measured Time-of-Emergence for Different Molecular Beacons

| HCV Target | Time-of-Emergence for Different Molecular Beacons (minutes) | | |
|---|---|---|---|
| (copies/rxn) | SEQ ID NO: 138 | SEQ ID NO: 139 | SEQ ID NO: 140 |
| $5 \times 10^8$ | NT | 1.0 | 2.3 |
| $5 \times 10^7$ | 6.9 | 3.3 | 6.5 |

TABLE 18-continued

Measured Time-of-Emergence for Different Molecular Beacons

| HCV Target | Time-of-Emergence for Different Molecular Beacons (minutes) | | |
|---|---|---|---|
| (copies/rxn) | SEQ ID NO: 138 | SEQ ID NO: 139 | SEQ ID NO: 140 |
| $5 \times 10^6$ | 8.3 | 5.3 | 8.0 |
| $5 \times 10^5$ | 10.4 | 7.5 | 10.1 |
| $5 \times 10^4$ | 12.2 | 9.2 | 11.8 |
| $5 \times 10^3$ | 14.0 | 11.2 | 14.3 |
| $5 \times 10^2$ | 16.1 | 14.2 | 16.0 |
| $5 \times 10^1$ | 18.5 | 20.0 | 18.3 |
| 5 | NT | 27.4* | 21.0** |

"NT" = not tested
*= only one out of three replicates reactive
**= only three out of four replicates reactive This invention has been described with reference to a number of specific examples and embodiments thereof. Of course, a number of different embodiments of the present invention will suggest themselves to those having ordinary skill in the art upon review of the foregoing detailed description. Thus, the true scope of the present invention is to be determined upon reference to the appended claims.

What is claimed is:

1. A composition of oligonucleotides for amplifying and detecting an HBV nucleic acid wherein said composition comprises at least two amplification oligomers configured to generate an HBV amplicon from an HBV nucleic acid present in a test sample at a concentration as low as 200 copies/ml of reaction mixture, wherein:
   (a) the first amplification oligomer consists of a target hybridizing sequence, optionally, an upstream sequence that is not complementary to an HBV target sequence, and a 5' promoter sequence for an RNA polymerase, wherein the target hybridizing sequence consists of SEQ ID NO:25 or SEQ ID NO:28; and
   (b) the second amplification oligomer consists of a target hybridizing sequence consisting of SEQ ID NO:15.

2. The composition of claim 1, wherein the amplification oligomer at (a) is selected from the group consisting of: SEQ ID NOS:42, 45, and combinations thereof.

3. The composition of claim 1, wherein the composition is provided as a component of a kit for the detection of HBV nucleic acid.

4. The composition of claim 1, wherein the composition is provided as a component of a kit for screening donated blood samples or plasma samples for the presence of HBV.

5. The composition of claim 4, further comprising components for amplification and/or detection of HIV-1 nucleic acids, HCV nucleic acids or both.

6. The composition of claim 1, further comprising a detectably labeled probe complementary to an HBV amplicon.

7. The composition of claim 6, wherein the detectably labeled probe comprises a fluorescent label.

8. The composition of claim 6, wherein said detectably labeled probe is a molecular beacon.

9. A method for screening donated blood or blood products for the presence of HBV, comprising the steps of:
   a. contacting a test sample with
      (i) an amplification oligomer, consisting of a target hybridizing sequence, optionally, an upstream sequence that is not complementary to an HBV target sequence, and a 5' promoter sequence for an RNA polymerase, wherein the target hybridizing sequence consists of SEQ ID NO:25 or SEQ ID NO:28; and
      (ii) an amplification oligomer consisting of a target hybridizing sequence consisting of SEQ ID NO:15; and
   b. amplifying any HBV nucleic acid that is present in the test sample in an isothermal in vitro nucleic acid amplification reaction to generate an HBV amplicon; and
   c. detecting the HBV amplicon; wherein detecting the presence of HBV in the test sample indicates that the blood product or the donated blood contains HBV nucleic acids, and wherein said method is capable of detecting HBV nucleic acid at a concentration at least as low as 200 copies/ml of reaction mixture.

10. The method of claim 9, further comprising a separating step to separate HBV nucleic acids from one or more other components in a biological sample.

11. The method of claim 10, wherein the separating step is performed using a target capture oligomer that includes a first sequence complementary to an HBV sequence and includes a second sequence for immobilization to a solid support.

12. The method of claim 9, wherein the amplification oligomer at a.(i) consists of deoxyribonucleic acid residues, or the amplification oligomer at a.(ii) consists of deoxyribonucleic acid residues, or a combination thereof.

13. The method of claim 9, wherein the isothermal in vitro amplification is a real-time amplification.

14. The method of claim 9, wherein steps b. and c. are performed simultaneously.

15. The method of claim 9, wherein the amplification oligomer at a.(i) is selected from the group consisting of: SEQ ID NOS:42, 45, and combinations thereof.

16. The method of claim 9, wherein step c. is performed using a detection probe oligomer.

17. The method of claim 16, wherein the detection probe oligomer is labeled with a chemiluminescent compound, a fluorescent compound, a quencher compound or a combination thereof.

18. The method of claim 9, wherein the test sample is derived from a pool of blood donated by two or more blood donors.

19. The method of claim 9, wherein the isothermal in vitro nucleic acid amplification reaction is a multiplex nucleic acid amplification reaction that amplifies HIV-1 nucleic acid, HCV nucleic acid, or HIV-1 nucleic acid and HCV nucleic acid in addition to HBV nucleic acid.

20. The method of claim 9, wherein the detecting step comprises detecting HBV genotype G amplicons.

21. A method for screening plasma for the presence of HBV, comprising the steps of:
   a. contacting a test sample with
      (i) an amplification oligomer consisting of a target hybridizing sequence, optionally, an upstream sequence that is not complementary to an HBV target sequence, and a 5' promoter sequence for an RNA polymerase, wherein the target hybridizing sequence consists of SEQ ID NO:25 or SEQ ID NO:28; and
      (ii) an amplification oligomer consisting of a target hybridizing sequence consisting of SEQ ID NO:15; and
   b. amplifying any HBV nucleic acid that is present in the test sample in an isothermal in vitro nucleic acid amplification reaction to generate an HBV amplicon; and
   c. detecting the HBV amplicon;
   wherein detecting the presence of HBV in the test sample indicates that the plasma contains HBV nucleic acids, and wherein said method is capable of detecting HBV nucleic acid at a concentration at least as low as 200 copies/ml of reaction mixture.

22. The method of claim 21, further comprising a separating step to separate HBV nucleic acids from one or more other components in a biological sample.

23. The method of claim 22, wherein the separating step is performed using a target capture oligomer that includes a first sequence complementary to an HBV sequence and includes a second sequence for immobilization to a solid support.

24. The method of claim 21, wherein the amplification oligomer at a.(i) consists of deoxyribonucleic acid residues, or the amplification oligomer at a.(ii) consists of deoxyribonucleic acid residues, or a combination thereof.

25. The method of claim 21, wherein the isothermal in vitro amplification is a real-time amplification.

26. The method of claim 21, wherein steps b. and c. are performed simultaneously.

27. The method of claim 21, wherein the amplification oligomer at a.(i) is selected from the group consisting of: SEQ ID NOS: 42, 45, and combinations thereof.

28. The method of claim 21, wherein step c. is performed using a detection probe oligomer.

29. The method of claim 28, wherein the detection probe oligomer is labeled with a chemiluminescent compound, a fluorescent compound, a quencher compound or a combination thereof.

30. The method of claim 21, wherein the test sample is further tested for the presence of HIV-1 nucleic acid, HCV nucleic acid or both.

31. The method of claim 21, wherein the isothermal in vitro nucleic acid amplification reaction is a multiplex nucleic acid amplification reaction that amplifies HIV-1 nucleic acid, HCV nucleic acid, or HIV-1 nucleic acid and HCV nucleic acid in addition to HBV nucleic acid.

32. The method of claim 21, wherein the detecting step comprises detecting HBV genotype G amplicons.

33. The method of claim 21, wherein the test sample is derived from a pool of plasma donated by two or more donors.

* * * * *